United States Patent
Yang et al.

[11] Patent Number: 6,057,338
[45] Date of Patent: May 2, 2000

[54] SOMATOSTATIN AGONISTS

[75] Inventors: Lihu Yang, Edison; Arthur A. Patchett, Westfield; Alexander Pasternak, Princeton; Scott Berk, Maplewood, all of N.J.

[73] Assignee: Merck & Co., Inc., Rahway, N.J.

[21] Appl. No.: 09/053,244

[22] Filed: Apr. 1, 1998

Related U.S. Application Data

[60] Provisional application No. 60/042,633, Apr. 4, 1997, and provisional application No. 60/064,381, Nov. 6, 1997.

[51] Int. Cl.[7] .................. A61K 31/445; C07D 401/00
[52] U.S. Cl. .................. 514/321; 514/323; 546/199; 546/201
[58] Field of Search ................... 514/323, 321; 546/201, 199

[56] References Cited

U.S. PATENT DOCUMENTS

| | | | |
|---|---|---|---|
| 4,242,347 | 12/1980 | Huebner | 514/321 |
| 4,310,518 | 1/1982 | Freidinger et al. | 514/11 |
| 5,360,807 | 11/1994 | Janssens et al. | 514/318 |
| 5,710,155 | 1/1998 | Schnorrenberg et al. | 514/255 |
| 5,869,489 | 2/1999 | Shah et al. | 514/253 |

FOREIGN PATENT DOCUMENTS 2311523  1/1997  United Kingdom .

OTHER PUBLICATIONS

Chem. Abs., vol. 119, No. 23, p. 69, col. 1, 1993.
Chem. Abs., vol. 128, No. 2, p. 386, col. 1, 1998.
Chem. Abs., vol. 128, No. 19, p. 604, col. 2, 1998.
Betoin et al. "In vitro and in vivo evidence for a tachykinin NK1 receptor antagonist effect of vapreotide, an analgesic cyclic analog of somatostatin" CA 123:26282, 1995.

*Primary Examiner*—Ceila Chang
*Attorney, Agent, or Firm*—James L. McGinnis; David L. Rose

[57] ABSTRACT

This invention relates to somatostatin agonist compounds which are potent with high selectivity toward the receptor subtype 2. Compounds of the formula:

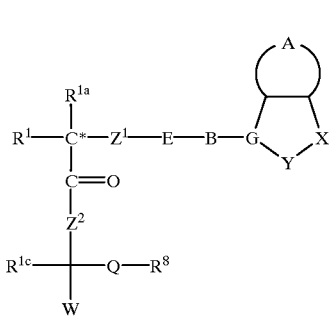

including pharmaceutically acceptable salts and hydrates thereof are disclosed. These compounds are useful in the treatment of diabetes, cancer, acromegaly, restenosis, depression, irritable bowel syndrome, pain and diabetic retinopathy. Many of the compounds are also orally active.

23 Claims, No Drawings

SOMATOSTATIN AGONISTS

This application claims benefit of provisional application Ser. No. 60/042,633 filed Apr. 4, 1997 and provisional application Ser. No. 60/064,381 filed Nov. 6, 1997.

BACKGROUND OF THE INVENTION

Somatostatin (SST) is a widely distributed peptide occurring in two forms SST-14 (with 14 amino acids) and SST-28 (with 28 amino acids). SST has multiple functions including modulation of secretion of growth hormone, insulin, glucagon, pancreatic enzymes and gastric acid, in addition to having potent anti-proliferative effects.

The mechanism of action of somatostatin is mediated via high affinity membrane associated receptors. Five somatostatin receptors (SSTR1–5) are known (Reisine, T.; Bell, G. I. *Endocrine Reviews* 1995, 16, 427–442). All five receptors are heterogeneously distributed and pharmacologically distinct. Structure-function studies with a large number of peptidal analogs have shown that the Trp-Lys dipeptide of somatostatin is important for high-affinity binding. The availability of these receptors now makes it possible to design selectively active ligands for the sub-types to determine their physiological functions and to guide potential clinical applications. For example, studies utilizing subtype selective peptides have provided evidence that somatostatin subtype 2 receptors (SSTR2) mediates the inhibition of growth hormone release from the anterior pituitary and glucagon release from the pancreas, whereas SSTR5 selective agonists inhibit insulin release. These results imply the usefulness of SSTR2 selective analogs in the treatment of diabetes and many of the compounds of this invention have that selectivity.

In addition, the novel compounds described herein are useful in the therapy of a variety of conditions which include acromegaly, retinal neovascularization, neuropathic and visceral pain, irritable bowel syndrome, chronic atrophic gastritis, Crohn's disease, rheumatoid arthritis and sarcoidosis. The instant compounds inhibit cell proliferation and cause the regression of certain tumors including breast cancer and pancreatic cancer. They are useful in preventing restenosis after angioplasty, they prevent non-steroid anti-inflammatory drug (NSAID) induced ulcers, they are useful in treating colitis and to inhibit cystoid macular edema. Their central activities include promotion of REM sleep and an increase in cognitive function. They also have analgesic activities and can be used, for example, to treat cancer pain, cluster headache and post operative pain and they are usefull in the prevention and treatment of migraine attacks and depression. The compounds described herein may be used in combination with other therapies, for example, with rapamycin to treat cancers, restenosis and atherosclerosis and with angiotensin converting enzyme inhibitors and insulin in the treatment of diabetes. The compounds of this invention are also remarkably reduced in size in comparison with the natural hormone and its peptide analogs such as octreotide and seglitide, which allows ease of formulation. Many of the instant compounds show activity following oral administration.

This invention relates to compounds which are agonists of somatostatin and selective toward somatostatin receptor subtype SSTR2. The compounds have a number of clinical uses including in the treatment and prevention of diabetes, cancer, acromegaly, depression, chronic atrophic gastritis, Crohn's disease, ulcerative colitis, retinopathy, arthritis, pain both viseral and neuropathic and to prevent restenosis.

Many of the compounds are orally active. Thus, it is an object of this invention to describe such compounds. It is a further object to describe the specific preferred stereoisomers of the somatostatin agonists. A still further object is to describe processes for the preparation of such compounds. Another object is to describe methods and compositions which use the compounds as the active ingredient thereof. Further objects will become apparent from reading the following description.

SUMMARY OF THE INVENTION

The present invention relates to compounds represented by formula I:

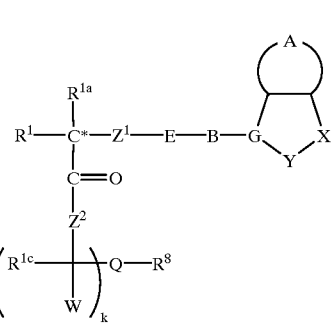

as well as pharmaceutically acceptable salts and hydrates thereof, wherein:

$R^1$ is selected from the group consisting of: $C_{1-10}$alkyl, aryl, aryl($C_{1-6}$alkyl)—, $C_{3-7}$cycloalkyl($C_{1-6}$alkyl)—, $C_{1-5}$alkyl-K-($C_1$–$C_5$ allyl)—, aryl($C_{0-5}$alkyl)-K-($C_{1-5}$alkyl)—, and $C_{3-7}$cycloalkyl($C_{0-5}$alkyl)-K-($C_{1-5}$alkyl)—, wherein K is —O—, —S(O)$_m$—, —N(R$^2$)C(O)—, —C(O)N(R$^2$)—, —CR$^2$=CR$^2$— or —C≡C—, the alkyl portions of which being optionally substituted with by 1 to 5 halogen groups, S(O)$_m$R$^{2a}$, 1 to 3 of OR$^{2a}$ groups or C(O)OR$^{2a}$, and wherein aryl is selected from the group consisting of: phenyl, naphthyl, biphenyl, quinolinyl, isoquinolinyl, indolyl, azaindolyl, pyridyl, benzothienyl, benzofuranyl, thiazolyl and benzimidazolyl, said aryl groups being unsubstituted or substituted with 1 to 3 $C_{1-6}$ alkyl or halo groups, 1 to 2 —OR$^2$ groups, methylenedioxy, —S(O)$_m$R$^2$, 1 to 2 —CF$_3$ groups, —OCF$_3$, —NO$_2$, —N(R$^2$)C(O)(R$^2$), —C(O)OR$^2$, —C(O)N(R$^2$)$_2$, 1H-tetrazol-5-yl, —SO$_2$N(R$^2$)(R$^2$), —N(R$^2$)SO$_2$ phenyl, or —N(R$^2$)SO$_2$R$^2$;

$R^2$ is selected from the group consisting of: H, $C_{1-8}$alkyl, —(CH$_2$)$_t$-aryl and $C_{3-7}$cycloalkyl, and where two $R^2$ groups are present, they optionally are joined to form a $C_3$–$C_8$ ring, optionally interrupted by O, S or NR$^{3a}$, in which R$^{3a}$ is H or $C_{1-6}$alkyl optionally substituted by OH;

t is an integer from 0 to 3;

and when $R^2$ is other than H, $R^2$ is optionally substituted with 1 to 5 halogen groups, S(O)$_m$R$^{2a}$, 1 to 3 of OR$^{2a}$ groups or C(O)OR$^{2a}$, $R^{2a}$ is H or $C_{1-3}$ alkyl optionally substituted by OH;

m is 0, 1 or 2;

$R^{1a}$ is H or $C_{1-3}$alkyl;

$Z^1$ is selected from the group consisting of —O—, —CH$_2$— and —NR$_{2a}$;

E is selected from the group consisting of —SO$_2$—, —C(O)—, —CO(C(R$^2$)$_2$)$_n$—, —C(=N—CN)—, —C(=N—NO$_2$)— and —C(=N—SO$_2$N(R$^2$)$_2$)—;

n is an integer from 0 to 3;

B is selected from the group consisting of:

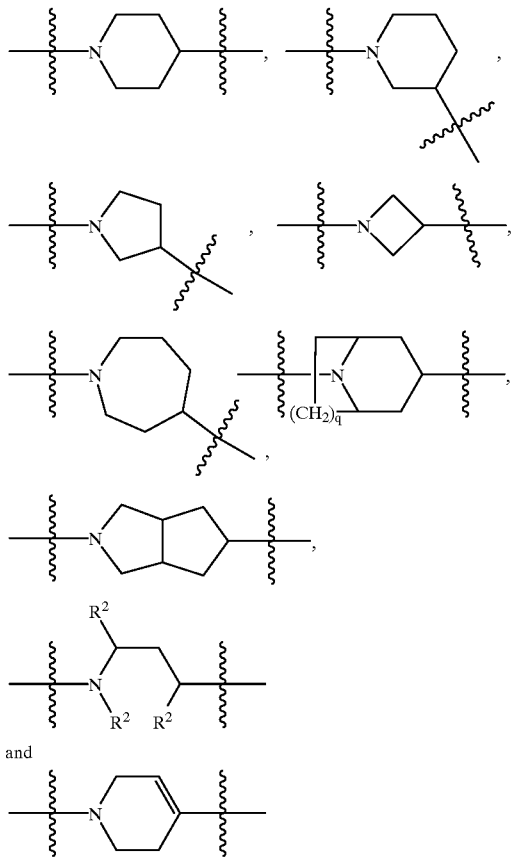

where attachment points are indicated by lines (⌇) and q is 0, 1, 2 or 3, said group being optionally substituted by $C_{1-6}$alkyl, and the $R^2$ and $(CH_2)_q$ groups are optionally substituted as described above;

represents an aromatic or non-aromatic 5–6 membered ring structure wherein:

G is N, CH or C;

Y is —C(O)—, —SO$_2$—, —C(OR$^{11}$)═, —C(SR$^{11}$)═, —C(NR$^{11}$)═, ═N—, —N(R$^{11}$)—, ═NC(O)— or —C(R$^{11}$)$_2$—;

and

X is —N(R$^{11}$l)—, ═N—, ═N—C(R$^{11}$)$_2$—, —N(R$^{11}$)C(R$^{11}$)$_2$—, —O—, —O—C(R$^{11}$)$_2$—, —S—, —S—C(R$^{11}$)$_2$— or C(R$^{11}$)$_2$;

$R^{11}$ is H, $C_{1-8}$alkyl, $CF_3$, $CH_2CF_3$, —(CH$_2$)$_p$OR$^2$, —(CH$_2$)$_p$N(R$^2$)$_2$, —(CH2)$_p$N(R$^2$)C(O)N(R$^2$)$_2$, —(CH$_2$)$_p$N(R$^2$)C(O)R$^2$, —(CH$_2$)$_2$-heteroaryl, —(CH$_2$)$_p$N(R$^2$)SO$_2$C$_{1-4}$alkyl, —(CH$_2$)$_p$C(O)N(R$^2$)$_2$ or —(CH$_2$)$_p$C(O)OR$^2$, wherein heteroaryl is selected from tetrazolyl, oxadiazolyl, imidazolyl and triazolyl, said heteroaryl being optionally substituted with $R^2$, $OR^2$, $CF_3$ or $N(R^2)_2$ and where p is 0–3;

is a 5–10 membered fused aryl or heteroaryl group having 1–4 heteroatoms selected from O, S and N, or a 5–10 membered cycloalkyl or heterocycloalkyl group having 1–3 heteroatoms selected from O, S and N, said aryl, heteroaryl, cycloalkyl or heterocycloalkyl group being optionally substituted with 1–3 $C_{1-6}$alkyl or halo groups, —OR$^2$, N(R$^2$)$_2$, methylenedioxy, —S(O)$_m$R$^2$, —CF$_3$, —OCF$_3$, —NO$_2$, —N(R$^2$)C(O)(R$^2$), —C(O)OR$^2$, —C(O)N(R$^2$)$_2$, 1H-tetrazol-5-yl, —SO$_2$N(R$^2$)$_2$, —N(R$^2$)SO$_2$ phenyl, —N(R$^2$)C(O)N(R$^2$)$_2$ or —N(R$^2$)SO$_2$R$^2$;

$Z^2$ is selected from the group consisting of —O—, —CH$_2$—, —CHR$^{2b}$— and —NR$^{2b}$—, wherein $R^{2b}$ is selected from the group consisting of: H, $C_{1-8}$alkyl, —(CH$_2$)$_t$-aryl, —(CH$_2$)$_n$CO$_2$R$^2$, —(CH$_2$)$_n$CON(R$^2$)$_2$ and —(CH$_2$)$_n$OR$^2$, and when $Z^2$ is NR$^{2b}$ it can optionally be linked to $R^{1c}$, Q or W to form a C5–8 ring, which is optionally interrupted by O, S(O)$_m$ or NR$^{2a}$;

$R^{1c}$ is selected from the group consisting of: H, —(CH$_2$)$_q$SR$^2$, —(CH$_2$)$_q$OR$^2$ and $C_{1-8}$alkyl;

W is selected from the group consisting of: H, $C_{1-8}$alkyl, (CH$_2$)$_t$-aryl, —(CH$_2$)$_q$C(O)OR$^2$, —(CH$_2$)$_q$OR$^2$, —(CH$_2$)$_q$OC(O)R$^2$, —(CH$_2$)$_q$C(O)R$^2$, —(CH$_2$)$_q$C(O)(CH$_2$)$_t$aryl, —(CH$_2$)$_q$C(O)N(R$^2$)$_2$, —(CH$_2$)$_q$N(R$^2$)C(O)R$^2$, —(CH$_2$)$_q$N(R$^2$)SO$_2$R$^2$, —(CH$_2$)$_q$N(R$^2$)C(O)N(R$^2$)$_2$, —(CH$_2$)$_q$OC(O)N(R$^2$)$_2$, —(CH$_2$)$_q$N(R$^2$)C(O)OR$^2$, —(CH$_2$)$_q$N(R$^2$)SO$_2$N(R$^2$)$_2$, —(CH$_2$)$_q$S(O)$_m$R$^2$ and —(CH$_2$)$_t$-heteroaryl, the heteroaryl portion of which is selected from: tetrazolyl, oxadiazolyl, thiadiazolyl, triazolyl and pyrazinyl, optionally substituted with $R^2$, $N(R^2)_2$ or $OR^2$, and when $R^2$ is other than H, said $R^2$, $(CH_2)_q$ and the $(CH_2)_t$ portions of W are optionally substituted with 1 to 2 $C_{1-4}$alkyl, OR$^{2a}$, C(O)OR$^{2a}$ or 1–3 halo groups, and the aryl portions of W are optionally substituted with 1 to 3 halo groups, —OR$^2$, —CON(R$^2$)$_2$, —C(O)OR$^2$, $C_{1-4}$alkyl, —S(O)$_m$R$^2$, N(R$^2$)$_2$, CF$_3$ or 1H-tetrazol-5-yl;

k is 0 or 1, such that when k is 0, Q is attached directly to $Z^2$;

Q represents a member selected from the group consisting of:

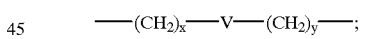
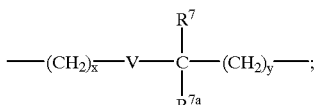
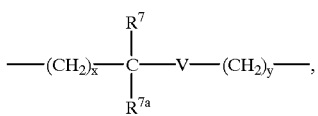
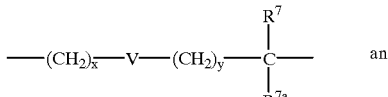
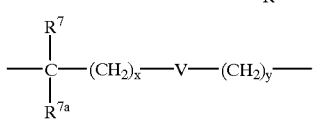

where x and y are independently 0, 1, 2, 3, 4, 5, 6;

V is an aromatic 6–12 membered mono- or bicyclic ring system or a non-aromatic 3–12 membered mono- or bicyclic ring system, optionally substituted with 1 to 2 $R^2$ groups, 1 to 3 halo groups, —$OR^2$, —$CON(R^2)_2$, —$C(O)OR^2$, —$C_{1-4}$alkyl, —$S(O)_mR^2$, $N(R^2)_2$, $CF_3$ or 1H-tetrazol-5-yl;

$R^7$ and $R^{7a}$ are independently $CF_3$ or $R^2$;

$R^8$ is selected from the group consisting of H,

—$NR^4R^5$, —$C(=NR^9)N(R^{10})_2$ and —$N^+(R^4)_3$;

$R^4$ and $R^5$ are independently selected from the group consisting of: $R^2$, —$C(=NR^2)N(R^2)_2$, —$C(=NCN)N(R^2)_2$, —$C(=NC(O)R^2)N(R^2)_2$, $C(=NSO_2R^2)N(R^2)_2$, —$C(=NNO_2)NR^2$, heteroaryl, —$C(O)N(R^2)_2$, —$C(=S)N(R^2)_2$, —$C(O)R^2$, 2,2,2-trifluoroethyl, 3,3,3-trifluoropropyl and —$(CH_2)_t$-cyclopropyl, or $R^4$ and $R^5$ are taken together and represent —$(CH_2)_d$—$L_a$—$(CH_2)_e$— wherein $L_a$ is —$C(R^2)_2$—, —O—, —S(O)m— or —$N(R^2)$—, and d and e are independently 0 to 3 such that d plus e equals 2–6, and said heteroaryl and $R^2$ other than H being optionally substituted with 1–3 $C_{1-6}$alkyl groups, 1–7 halo groups, $N(R^2)_2$, $OR^2$, $N(R^2)C(O)R^2$, $C(O)N(R^2)$, $OC(O)R^2$, $S(O)_mR^2$, $CF_3$, $OCF_3$, $NO_2$, $N(R^2)C(O)(R^2)$, $N(R^2)C(O)N(R^2)_2$, $C(O)OR^2$, $C(O)N(R^2)_2$, $SO_2N(R^2)_2$, $N(R^2)SO_2R^2$ or methylenedioxy;

and $R^9$ and $R^{10}$ are independently H or $C_{1-8}$alkyl or may be taken together and represent a $C_{5-8}$ ring, optionally substituted by 1–5 halo groups, $OR^2$ or $S(O)_mR^2$.

Pharmaceutical compositions and methods of treatment are also included.

DETAIL DESCRIPTION OF THE INVENTION

The compounds and their pharmaceutically acceptable salts and hydrates of the present invention are represented by structural formula I':

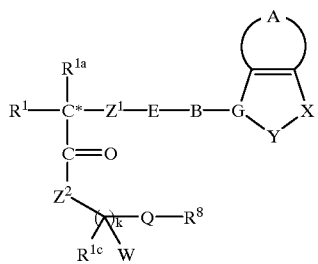

Formula I' wherein:

$R^1$ is selected from the group consisting of: $C_1$–$C_{10}$ alkyl, aryl, aryl ($C_1$–$C_6$ alkyl), ($C_3$–$C_7$ cycloallyl)($C_1$–$C_6$ alkyl)—, ($C_1$–$C_5$ alkyl)-K-($C_1$–$C_5$ alkyl)—, aryl($C_0$–$C_5$ alkyl)-K-($C_1$–$C_5$ alkyl)—, and ($C_3$–$C_7$ cycloalkyl)($C_0$–$C_5$ alkyl)-K-($C_1$–$C_5$ alkyl)—, where K is —O—, —$S(O)_m$—, —$N(R^2)$C(O)—, —$C(O)N(R^2)$—, —$CR^2=CR^2$—, or — C∫C—, where $R^2$ and alkyl may be further substituted by 1 to 5 halogen, $S(O)_mR^{2a}$, 1 to 3 of $OR^{2a}$ or $C(O)OR^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, —$SO_2N(R^2)(R^2)$, —$N(R^2)SO_2$ phenyl, or —$N(R^2)SO_2R^2$;

$R^2$ is selected from: hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclicring, optionally including oxygen, sulfur or $NR^{3a}$, where $R^{3a}$ is hydrogen, or $C_1$–$C_6$ alkyl, optionally substituted by hydroxyl; Aryl is defined in the body of the case.

$R^{1a}$ is selected from the group consisting of hydrogen, and $C_1$–$C_3$ alkyl;

$R^{2a}$ is selected from the group consisting of hydrogen and $C_1$–$C_3$ alkyl, said alkyl optionally substituted by hydroxyl;

$R^{2b}$ is selected from hydrogen, $C_1$–$C_8$ alkyl, $(CH_2)_t$ aryl, —$(CH_2)_nCO_2R^2$, —$(CH_2)_nCON(R^2)_2$, —$(CH_2)_nOH$, $(CH_2)_nCF_3$, $(CH_2)_t$ heteroaryl or —$(CH_2)_nOR^2$;

$R^{1c}$ is selected from the group consisting of hydrogen, —$(CH_2)_qSR^2$, —$(CH_2)_qOR^2$ and $C_1$–$C_8$ alkyl;

$Z_1$ is selected from the group consisting of —O—, —$CH_2$— and —$NR^{2a}$;

$Z^2$ is selected from the group consisting of —O—, —$CH_2$—, —$CHR^{2b}$— and —$NR^{2b}$, when $Z^2$ is $NR^{2b}$ it can optionally be linked to $R^{1c}$, Q and/or W to form a C5–8 cyclic ring, which can optionally be interrupted by oxygen, $S(O)_m$ or $NR^{2a}$;

W is selected from the group consisting of: hydrogen, $C_1$–$C_8$ alkyl, $(CH_2)_t$ aryl, —$(CH_2)_qC(O)OR^2$, —$(CH_2)_qOR^2$, —$(CH_2)_qOC(O)R^2$, —$(CH_2)_qC(O)R^2$, —$(CH_2)_qC(O)(CH_2)_t$aryl, —$(CH_2)_qC(O)N(R^2)_2$, —$(CH_2)_qN(R^2)C(O)R^2$, —$(CH_2)_qN(R^2)SO_2R^2$, —$(CH_2)_qN(R^2)C(O)N(R^2)_2$, —$(CH_2)_qOC(O)N(R^2)_2$, —$(CH_2)_qN(R^2)C(O)OR^2$, —$(CH_2)_qN(R^2)SO_2N(R^2)_2$, —$(CH_2)_qS(O)_mR^2$, and $(CH_2)_t$ heteroaryl where the heteroaryl is preferably tetrazole, oxadiazole, thiadiazole, triazole or pyrazine, which is optionally substituted with $R^2$, $N(R^2)_2$ and $OR^2$, where $R^2$, $(CH_2)_q$ and $(CH2)_t$ are optionally substituted with 1 to 2 $C_1$–$C_4$ alkyl, $OR^2$, $C(O)OR^2$, 1–3 halo and said aryl is optionally substituted with 1 to 3 halogen, —$OR^2$, —$CON(R^2)_2$, —$C(O)OR^2$, $C_1$–$C_4$ alkyl, —$S(O)_mR^2$, $N(R^2)_2$, $CF_3$ or 1H-tetrazol-5-yl;

Q is selected from the group consisting of:

——$(CH_2)_x$——V——$(CH_2)_y$——;

——$(CH_2)_x$——V——$\underset{R^{7a}}{\overset{R^7}{C}}$——$(CH_2)_y$——;

——$(CH_2)_x$——$\underset{R^{7a}}{\overset{R^7}{C}}$——V——$(CH_2)_y$—— and

——$(CH_2)_x$——V——$(CH_2)_y$——$\underset{R^{7a}}{\overset{R^7}{C}}$——

——$(CH_2)_x$——V——$(CH_2)_y$——$\underset{R^{7a}}{\overset{R^7}{C}}$——;

where x and y are independently 0, 1, 2, 3, 4, 5, 6;

V is a $C_{3-12}$ nonaromatic cyclic or bicyclic ring or an aromatic such as benzene, napthalene; said aromatic or non aromatic ring can be optionally substituted with 1 to 2 $R^2$, 1 to 3 halogen, —OR$^2$, —CON(R$^2$)$_2$, —C(O)OR$^2$, C$_1$–C$_4$ alkyl, —S(O)$_m$R$^2$, N(R$^2$)$_2$, CF$_3$ or 1H-tetrazol-5-yl; and in the case where diastereo- or regio- isomers are present, all are included;

R$^7$ and R$^{7a}$ are independently trifluoromethyl or R$^2$;

R8 is selected from the group consisting of

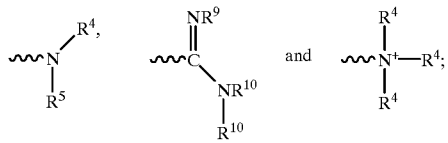

R$^4$ and R$^5$ are independently selected from the group consisting of R$^2$, —C(=NR$^2$)N(R$^2$)$_2$, —C(=NCN)N(R$^2$)$_2$, —C(=NC(O)R$^2$)N(R$^2$)$_2$, C(=NSO$_2$R$^2$)N(R$^2$)$_2$, —C(=NNO$_2$)NR$^2$, heteroaryl, (CH$_2$)$_n$CO$_2$R$^2$ —C(=O)N (R$^2$)$_2$, —C(=S)N(R$^2$)$_2$, —C(=O)R$^2$, 2,2,2-trifluoroethyl, 3,3,3-trifluoropropyl, (CH$_2$)$_t$ cyclopropyl, or R$^4$ and R$^5$ may be taken together to form —(CH$_2$)$_d$-L$_a$(CH$_2$)$_e$— where L$_a$ is —C(R$^2$)$_2$—, —O—, —S(O)$_m$— or —N(R$^2$)—, d and e are independently 1 to 3, said heteroaryl and R$^2$ optionally substituted with 1–3 groups of C$_{1-6}$ alkyl, 1–7 halo, N(R$^2$)$_2$, OR$^2$, N(R$^2$)C(O)R$^2$, C(O)N(R$^2$), OC(O)R$^2$, S(O)$_m$R$^2$, CF$_3$, OCF$_3$, NO$_2$, N(R$^2$)C(O)(R$^2$), N(R$^2$)C(O)N(R$^2$)$_2$, C(O)OR$^2$, C(O)N(R$^2$)$_2$, SO$_2$N(R$^2$)$_2$, N(R$^2$)SO$_2$R$^2$, or methylenedioxy, and the heteroaryl is pyridyl, imidazolyl, pyrimidinyl, thiazolyl or pyrazinyl;

E is selected from the group consisting of —SO$_2$—, —CO(C(R$^2$)$_2$)$_n$—, —C(=N—CN)—, —C(=N—NO$_2$)— and —C(=N—SO$_2$N(R$^2$)$_2$)—;

R$^9$ & R$^{10}$ are independently H, C$_{1-8}$ alkyl or may be taken together to form a C5–8 cyclic ring, which can optionally be substituted by 1–5 halogen, OR$^2$ or S(O)$_m$R$^2$;

B is selected from the group consisting of a noncyclic, heterocyclic or heterobicyclic ring selected from the group consisting of

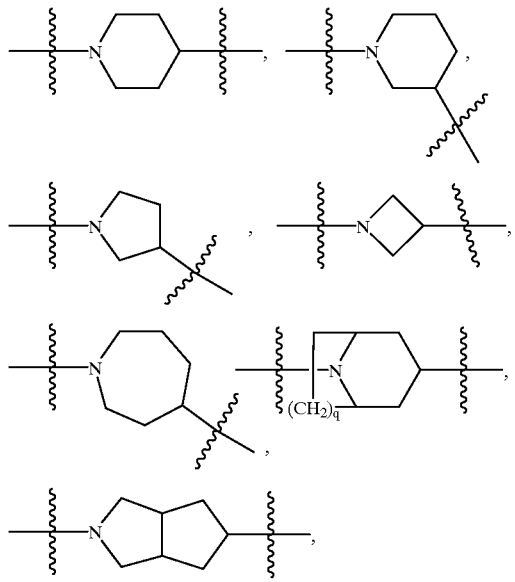

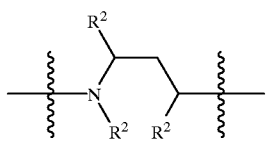

and

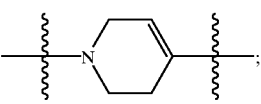

where attachment points are indicated by lines (ƒ) external to the rings and to the open ring which are optionally substituted by C$_1$–C$_6$ alkyl and where R$^2$ and (CH$_2$)$_q$ are described above;

G is N, CH or C=;

Y is —C(O)—, —SO$_2$—, —C(OR$^{11}$)=, —C(SR$^{11}$)=, —C(NR$^{11}$)=, =N—, N(R$^{11}$)—, =NC(O)—, or —C(R$^{11}$)$_2$—;

X is —N(R$^{11}$)—, =N—, =N—C(R$^{11}$)$_2$—, —N(R$^{11}$)C, (R$^{11}$)$_2$—, —O—, —O—C(R$^{11}$)$_2$—, —S—, —S—C(R$^{11}$)$_2$— or C(R$^{11}$)$_2$;

R$^{11}$ is H, C$_1$–C$_8$ alkyl, CF$_3$, CH$_2$CF$_3$, —(CH$_2$)$_p$OR$^2$, —(CH$_2$)$_p$N(R$^2$)$_2$, (CH$_2$)$_p$N(R$^2$)C(O)N(R$^2$)$_2$, —(CH$_2$)$_p$N(R$^2$) C(O)R$^2$, (CH$_2$)$_2$ heteroaryl, (CH$_2$)$_p$N(R$^2$)SO$_2$C$_1$–C$_4$ alkyl, —(CH$_2$)$_p$C(O)N(R$^2$)$_2$, or —(CH$_2$)$_p$C(O)OR$^2$ where heteroaryl is tetrazole, oxadiazole, imidazole or triazole which are optionally substituted with R$^2$, OR$^2$, CF$_3$ or N(R$^2$)$_2$ and where p is 0–3;

A is a fused aryl or heteroaryl group 1–4 atoms of which are heteroatoms of N, O and/or S; cycloalkyl; or heterocycloalkyl group, 1–3 atoms of which are heteroatoms N, O and/or S, said aryl, heteroaryl, cycloalkyl or heterocycloalkyl group containing from 5 to 10 atoms and being optionally substituted with 1–3 groups of C$_1$–C$_6$ alkyl, halogen, —OR$^2$, N(R$^2$)$^2$, methylenedioxy, —S(O)$_m$R$^2$, —CF$_3$, —OCF$_3$, nitro, —N(R$^2$)C(O)(R$^2$), —C(O)OR$^2$, —C(O)N(R$^2$)$_2$, —1H-tetrazol-5-yl, —SO$_2$N(R$^2$)$_2$, —N(R$^2$) SO$_2$ phenyl, N(R$^2$)C(O)N(R$^2$) or —N(R$^2$)SO$_2$R$^2$, and in the case where regioisomers are present, all are included;

k is an integer from 0 to 1, such that when k is 0, Q is attached directly to z$^2$;

m is an integer from 0 to 2;

n is an integer from 0 to 3;

q is an integer from 0 to 3; and t is an integer from 0 to 3.

Preferred compounds of the instant invention include those of Formula Ib:

Formula Ib

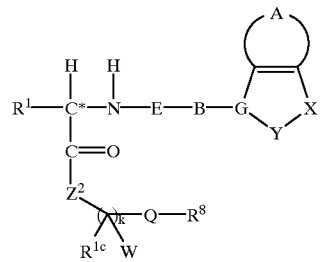

as well as pharmaceutically acceptable salts and hydrates thereof, wherein:

R$^1$ is selected from the group consisting of: C$_1$–C$_{10}$ alkyl, aryl, aryl (C$_1$–C$_6$ alkyl), (C$_3$–C$_7$ cycloalkyl)(C$_1$–C$_6$ alkyl)—, ($C_1$–$C_5$ alkyl)-K-($C_1$–$C_5$ alkyl)—, aryl($C_0$–$C_5$ alkyl)-K-($C_1$–$C_5$ alkyl)—, and ($C_3$–$C_7$ cycloalkyl)($C_0$–$C_5$ alkyl)-K-($C_1$–$C_5$ alkyl)—, where K is —O—, —S(O)$_m$—, —N($R^2$)C(O)—, —C(O)N($R^2$)—, —C$R^2$=C$R^2$—, or —C≡C—, where $R^2$ and alkyl may be further substituted by 1 to 5 halogen, S(O)$_m$$R^{2a}$, 1 to 3 of O$R^{2a}$ or C(O)O$R^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of $C_1$–$C_6$ alkyl, 1 to 3 of halogen, 1 to 2 of —O$R^2$, methylenedioxy, —S(O)$_m$$R^2$, 1 to 2 of —CF$_3$, —OCF$_3$, nitro, —N($R^2$)C(O)($R^2$), —C(O)O$R^2$, —C(O)N($R^2$)($R^2$), —1H-tetrazol-5-yl, —SO$_2$N($R^2$)($R^2$), —N($R^2$)SO$_2$phenyl, or —N($R^2$)SO$_2$$R^2$;

$R^2$ is selected from: hydrogen, $C_1$–$C_8$ alkyl, (CH$_2$)$_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or N$R^{3a}$, where $R^{3a}$ is hydrogen, or $C_1$–$C_6$ alkyl, optionally substituted by hydroxyl;

$R^{2a}$ is selected from the group consisting of hydrogen and $C_1$–$C_3$ alkyl, said alkyl optionally substituted by hydroxyl;

$Z^2$ is selected from the group consisting of —O—, —CH$_2$—, —CHR$_{2b}$— and —NR$^{2b}$, when $Z^2$ is NR$^{2b}$ it can optionally be linked to $R^{1c}$, Q and/or W to form a $C_{5-8}$ cyclic ring, which can optionally be interrupted by oxygen, S(O)m or NR$^{2a}$;

$R^{2b}$ is selected from hydrogen, $C_1$–$C_8$ alkyl, (CH$_2$)$_t$ aryl, —(CH$_2$)$_n$CO$_2$$R^2$, —(CH$_2$)$_n$CON($R^2$)$_2$, —(CH$_2$)$_n$OH, (CH$_2$)$_n$CF$_3$, (CH$_2$)$_t$ heteroaryl or —(CH$_2$)$_n$O$R^2$;

$R^{1c}$ is selected from the group consisting of hydrogen, and $C_1$–$C_8$ alkyl;

W is selected from the group consisting of: hydrogen, $C_1$–$C_8$ alkyl, (CH2)$_t$ aryl, —(CH$_2$)$_q$C(O)O$R^2$, —(CH$_2$)$_q$O$R^2$, —(CH$_2$)$_q$OC(O)$R^2$, —(CH$_2$)$_q$C(O)$R^2$, —(CH$_2$)$_q$C(O)(CH$_2$)$_t$aryl, —(CH$_2$)$_q$C(O)N($R^2$)$_2$, —(CH$_2$)$_q$N($R^2$)C(O)$R^2$, —(CH$_2$)$_q$N($R^2$)SO$_2$$R^2$, —(CH$_2$)$_q$N($R^2$)C(O)N($R^2$)$_2$, —(CH$_2$)$_q$OC(O)N($R^2$)$_2$, —(CH$_2$)$_q$N($R^2$)C(O)O$R^2$, —(CH$_2$)$_q$N($R^2$)SO$_2$N($R^2$)$_2$, —(CH$_2$)$_q$S(O)$_m$$R^2$, and (CH$_2$)$_t$ heteroaryl where the heteroaryl is preferably tetrazole, oxadiazole, thiadiazole, triazole or pyrazine, which is optionally substituted with $R^2$, N($R^2$)$_2$ and O$R^2$, where $R^2$, (CH$_2$)$_q$ and (CH2)$_t$ are optionally substituted with 1 to 2 $C_1$–$C_4$ alkyl, O$R^2$, C(O)O$R^2$, 1–3 halo and said aryl is optionally substituted with 1 to 3 halogen, —O$R^2$, —CON($R^2$)$_2$, —C(O)O$R^2$, $C_1$–$C_4$ alkyl, —S(O)$_m$$R^2$, N($R^2$)$_2$, CF$_3$ or 1H-tetrazol-5-yl;

Q is

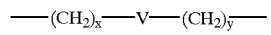
—(CH$_2$)$_x$—V—(CH$_2$)$_y$— or

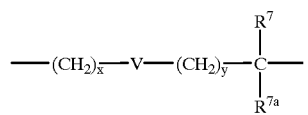
—(CH$_2$)$_x$—V—(CH$_2$)$_y$—C—
$\qquad\qquad\qquad\qquad$ | 
$\qquad\qquad\qquad\qquad$ $R^{7a}$ where x and y are independently 0, 1, 2, 3, 4;

V is a $C_{3-8}$ nonaromatic cyclic or bicyclic ring consisting of, cyclopropane, cyclobutane, cyclopentane, cyclohexane, cycloheptane, cyclooctane; or an aromatic such as benzene, napthalene; said aromatic or non aromatic ring can be optionally substituted with 1 to 2 $R^2$, 1 to 3 halogen, —O$R^2$, —CON($R^2$)$_2$, —C(O)O$R^2$, $C_1$–$C_4$ alkyl, —S(O)$_m$$R^2$, N($R^2$)$_2$, CF$_3$ or 1H-tetrazol-5-yl, or where Q and R8 can be lined to form a $C_{3-8}$ cyclic ring; and in the case where diastereo- or regio- isomers are present, all are included;

$R^7$ and $R^{7a}$ are independently trifluoromethyl or $R^2$;
R8 is selected from the group consisting of

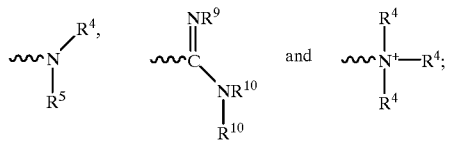

$R^4$ and $R^5$ are independently selected from the group consisting of $R^2$, —C(=N$R^2$)N($R^2$)$_2$, —C(=NCN)N($R^2$)$_2$, —C(=NC(O)$R^2$)N($R^2$)$_2$, C(=NSO$_2$$R^2$)N($R^2$)$_2$, —C(=NNO$_2$)N$R^2$, heteroaryl, (CH$_2$)$_n$CO$_2$$R^2$—C(=O)N($R^2$)$_2$, —C(=S)N($R^2$)$_2$, —C(=O)$R^2$, 2,2,2-trifluoroethyl, 3,3,3-trifluoropropyl, (CH$_2$)$_t$ cyclopropyl, or $R^4$ and $R^5$ may be taken together to form —(CH$_2$)$_d$-L$_a$(CH$_2$)$_e$— where L$_a$ is —C($R^2$)$_2$—, —O—, —S(O)$_m$— or —N($R^2$)—, d and e are independently 1 to 3, said heteroaryl and $R^2$ optionally substituted with 1–3 groups of $C_{1-6}$ alkyl, 1–7 halo, N($R^2$)$_2$, O$R^2$, N($R^2$)C(O)$R^2$, C(O)N($R^2$), OC(O)$R^2$, S(O)$_m$$R^2$, CF$_3$, OCF$_3$, NO$_2$, N($R^2$)C(O)($R^2$), N($R^2$)C(O)N($R^2$)$_2$, C(O)O$R^2$, C(O)N($R^2$)$_2$, SO$_2$N($R^2$)$_2$, N($R^2$)SO$_2$$R^2$, or methylenedioxy; and the heteroaryl is pyridyl, imidazolyl, pyrimidinyl, thiazolyl or pyrazinyl;

E is selected from the group consisting of —SO$_2$—, —CO(C($R^2$)$_2$)$_n$—, —C(=N—CN)—, —C(=N—NO$_2$)— and —C(=N—SO$_2$N($R^2$)$_2$)—;

$R^9$ & $R^{10}$ are independently H, $C_{1-8}$ alkyl or may be taken together to form a C5–8 cyclic ring, which can optionally be substituted by 1–5 halogen, O$R^2$ or S(O)$_m$$R^2$;

B is selected from the group consisting of a noncyclic or heterocyclic selected from the group consisting of

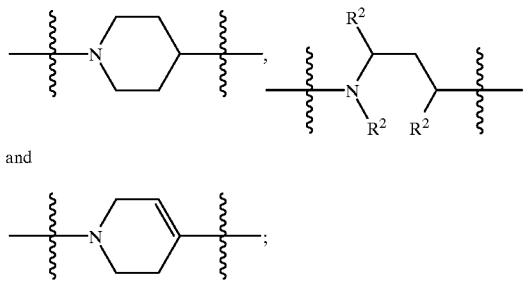

and where attachment points are indicated by lines (⸾) external to the rings and to the open ring which are optionally substituted by $C_1$–$C_6$ alkyl and where $R^2$ and (CH$_2$)$_q$ are described above;

G is N, CH or C=;

Y is —C(O)—, —SO$_2$—, —C(O$R^{11}$)=, —C(S$R^{11}$)=, —C(N$R^{11}$)=, =N—, N($R^{11}$)—, =NC(O)—, or —C($R^{11}$)$_2$—;

X is —N($R^{11}$)—, =N—, =N—C($R^{11}$)$_2$—, —N($R^{11}$)C($R^{11}$)$_2$—, —O—, —O—C($R^{11}$)$_2$—, —S—, —S—C($R^{11}$)$_2$— or C($R^{11}$)$_2$;

$R^{11}$ is H, $C_1$–$C_8$ alkyl, CF$_3$, CH$_2$CF$_3$, —(CH$_2$)$_p$O$R^2$, —(CH$_2$)$_p$N($R^2$)$_2$, (CH2)$_p$N($R^2$)C(O)N($R^2$)$_2$, —(CH$_2$)$_p$N($R^2$)C(O)$R^2$, (CH$_2$)$_2$ heteroaryl, (CH$_2$)$_p$N($R^2$)SO$_2$$C_1$–$C_4$ alkyl, —(CH$_2$)$_p$C(O)N($R^2$)$_2$, or —(CH$_2$)$_p$C(O)O$R^2$ where heteroaryl is tetrazole, oxadiazole, imidazole or triazole which are optionally substituted with $R^2$, O$R^2$, CF$_3$ or N($R^2$)$_2$ and where p is 0–3;

A is a fused aryl or heteroaryl group 1–4 atoms of which are heteroatoms of N, O and/or S; cycloalkyl; or heterocycloalkyl group, 1–3 atoms of which are heteroatoms N, O and/or S, said aryl, heteroaryl, cycloalkyl or heterocycloalkyl group containing from 5 to 10 atoms and being optionally substituted with 1–3 groups of $C_1$–$C_6$ alkyl, halogen, —$OR^2$, $N(R^2)2$ methylenedioxy, -$S(O)_mR^2$, —$CF_3$, -$OCF_3$, nitro, —$N(R^2)C(O)(R^2)$, —$C(O)OR^2$, —$C(O)N(R^2)_2$, —1H-tetrazol-5-yl, —$SO_2N(R^2)_2$, —$N(R^2)SO_2$ phenyl, $N(R^2)C(O)N(R^2)$ or $N(R^2)SO_2R^2$, and in the case where regioisomers are present, all are included;

k is an integer from 0 to 1, such that when k is 0, Q is attached directly to $Z^2$;

m is an integer from 0 to 2;

n is an integer from 0 to 3;

q is an integer from 0 to 3; and t is an integer from 0 to 3.

Even more preferred compounds of the instant invention include those of Formula Ic:

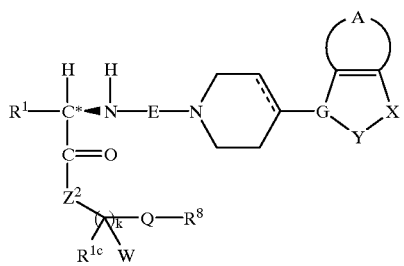

Formula Ic as well as pharmaceutically acceptable salts and hydrates thereof, wherein:

$R^1$ is selected from the group consisting of: $C_1$–$C_{10}$ alkyl, aryl, aryl ($C_1$–$C_6$ alkyl), ($C_3$–$C_7$ cycloalkyl)($C_1$–$C_6$ alkyl)—, ($C_1$–$C_5$ alkyl)-O-($C_1$–$C_5$ alkyl)—, and aryl($C_0$–$C_5$ alkyl)-O-($C_1$–$C_5$ alkyl)—, where $R^2$ and alkyl may be further substituted by 1 to 5 halogen, $S(O)_mR^{2a}$, 1 to 3 of $OR^{2a}$ or $C(O)OR^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, —$SO_2N(R^2)(R^2)$, —$N(R^2)SO_2$ phenyl, or —$N(R^2)SO_2R^2$;

$R^2$ is selected from: hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl;

$R^{2a}$ is selected from the group consisting of hydrogen and $C_1$–$C_3$ alkyl, said alkyl optionally substituted by hydroxyl;

$Z^2$ is selected from the group consisting of —O—, —CH2—,—$CHR^{2b}$— and —$NR^{2b}$, when $Z^2$ is $NR^{2b}$ it can optionally be linked to $R^{1c}$, Q and/or W to form a C5-8 cyclic ring;

$R^{2b}$ is selected from hydrogen, $C_1$–$C_8$ alkyl, $(CH_2)_t$ aryl, —$(CH_2)_nCO_2R^2$, —$(CH_2)_nCON(R^2)_2$, —$(CH_2)_nOH$, $(CH_2)_nCF_3$, $(CH_2)_t$ heteroaryl or —$(CH_2)_nOR^2$;

$R^{1c}$ is selected from the group consisting of hydrogen and $C_1$–$C_8$ alkyl;

W is selected from the group consisting of: hydrogen, $C_1$–$C_8$ alkyl, $(CH2)_t$ aryl, —$(CH_2)_qC(O)OR^2$, —$(CH_2)_qOR^2$, —$(CH_2)_qOC(O)R^2$, —$(CH_2)_qC(O)R^2$, —$(CH_2)_qC(O)(CH_2)_t$aryl, —$(CH_2)_qC(O)N(R^2)_2$, —$(CH_2)_qN(R^2)C(O)R^2$, —$(CH_2)_qN(R^2)SO_2R^2$, —$(CH_2)_qN(R^2)C$ (O)$N(R^2)_2$, —$(CH_2)_qOC(O)N(R^2)_2$, —$CH_2)_qN(R^2)C(O)$ $OR^2$, —$(CH_2)_qN(R^2)SO_2N(R^2)_2$, —$(CH_2)_qS(O)_mR^2$, and $(CH_2)_t$heteroaryl where the heteroaryl is preferably tetrazole, oxadiazole, thiadiazole, triazole or pyrazine, which is optionally substituted with $R^2$, $N(R^2)_2$ and $OR^2$, where $R^2$, $(CH_2)_q$ and (CH2)$_t$ are optionally substituted with 1 to 2 $C_1$–$C_4$ alkyl, $OR^2$, $C(O)OR^2$, 1–3 halo and said aryl is optionally substituted with 1 to 3 halogen, —$OR^2$, —CON $(R^2)_2$, —$C(O)OR^2$, $C_1$–$C_4$ alkyl, —$S(O)_mR^2$, $N(R^2)_2$, $CF_3$ or 1H-tetrazol-5-yl;

Q is

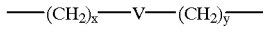

or

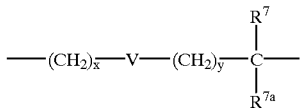

where x and y are independently 0, 1, 2, 3;

V is

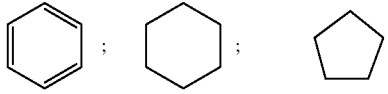

said the aromatic or non aromatic ring can be optionally substituted with 1 to 2 $R^2$, 1 to 3 halogen, —$OR^2$, —CON $(R^2)_2$, —$C(O)OR^2$, $C_1$–$C_4$ alkyl, —$S(O)_mR^2$, $N(R^2)_2$, $CF_3$ or 1H-tetrazol-5-yl, and in the case where diastereo- or regio- isomers are present, all are included;

$R^7$ and $R^{7a}$ are independently trifluoromethyl or $R^2$;

$R^8$ is

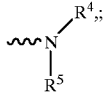

$R^4$ and $R^5$ are independently selected from the group consisting of $R^2$, 2,2,2-trifluoroethyl, 3,3,3-trifluoropropyl, $(CH_2)_t$ cyclopropyl or $(CH_2)_nCO_2R^2$;

E is selected from the group consisting of —$SO_2$—, —CO—, —C(=N—CN)—, —C(=N—$NO_2$)— and —C(=N—$SO_2NH_2$)—;

$R^9$ & $R^{10}$ are independently H or $C_{1-8}$ alkyl;

G is N, CH or C=;

Y is —C(O)—, —$SO_2$—, —$C(OR^{11})$=, —$C(SR^{11})$=, —$C(NR^{11})$=, =N—, $N(R^{11})$—, =NC(O)—, or —$C(R^{11})_2$—;

X is —$N(R^{11})$—, =N—, =N—$C(R^{11})_2$—, —$N(R^{11})C$ $(R^{11})_2$—, —O—, —O—$C(R^{11})_2$—, —S—, —S—$C(R^{11})_2$— or $C(R^{11})_2$;

$R^{11}$ is H, $C_1$–$C_8$ alkyl, $CF_3$, $CH_2CF_3$, —$(CH_2)_pOR^2$, —$(CH_2)_pN(R^2)_2$, (CH2)$_pN(R^2)C(O)N(R^2)_2$, —$(CH_2)_pN$ $(R^2)C(O)R^2$, $(CH_2)_2$ heteroaryl, $(CH_2)_pN(R^2)SO_2C_1$–$C_4$ alkyl, —$(CH_2)_pC(O)N(R^2)_2$, or —$(CH_2)_pC(O)OR^2$ where heteroaryl is tetrazole, oxadiazole, imidazole or triazole which are optionally substituted with $R^2$, $OR^2$, $CF_3$ or $N(R^2)_2$ and where p is 0–3;

A is a fused aryl or heteroaryl group 1–4 atoms of which are heteroatoms of N, O and/or S; cycloalkyl; or heterocycloalkyl group, 1–3 atoms of which are heteroatomseteroatoms N, O and/or S, said aryl, heteroaryl, cycloalkyl or heterocycloalkyl group containing from 5 to 10 atoms and being optionally substituted with 1–3 groups of $C_1$–$C_6$ alkyl, halogen, —$OR^2$, $N(R^2)_2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, — 1H-tetrazol-5-yl, —$SO_2N(R^2)_2$, —$N(R^2)SO_2$ phenyl, $N(R^2)C(O)N(R^2)$ or —$N(R^2)SO_2R^2$, and in the case where regioisomers are present, all are included;

k is an integer from 0 to 1, such that when k is 0, Q is attached directly to $Z^2$;

m is an integer from 0 to 2;

n is an integer from 0 to 3;

q is an integer from 0 to 3, and t is an integer from 0 to 3.

Still more preferred compounds of the instant invention include those of Formula Id:

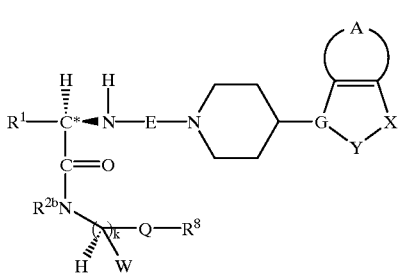

Formula Id as well as pharmaceutically acceptable salts and hydrates thereof, wherein:

$R^1$ is selected from the group consisting of:

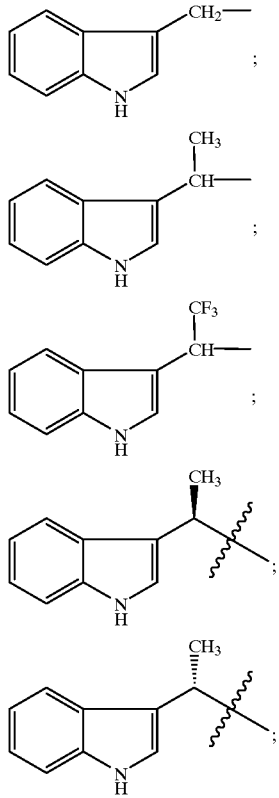

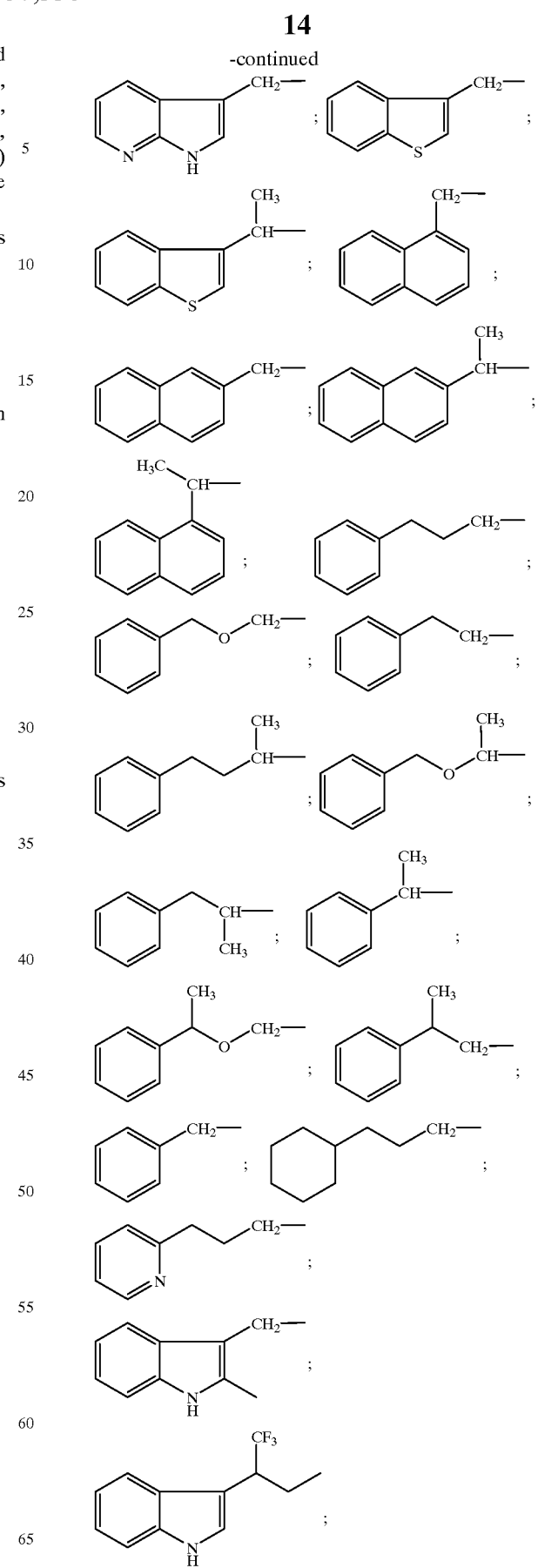

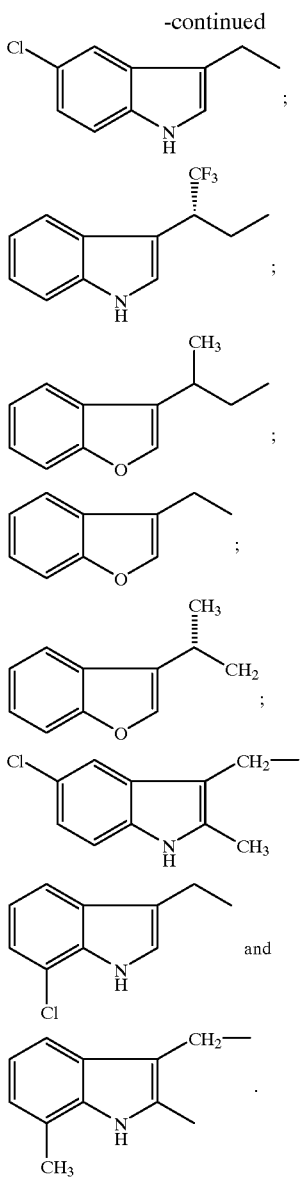

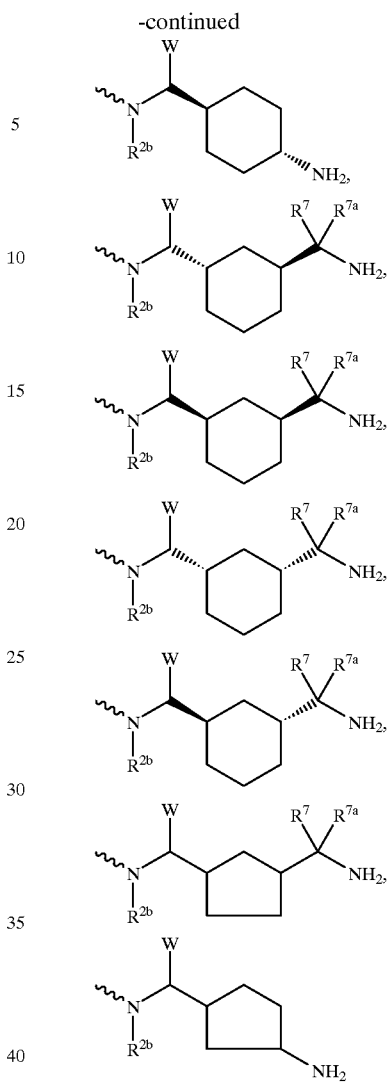

where the aryl or heteroaryl moiety is unsubstituted or substituted with a substitutent selected from: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, —$SO_2N(R^2)(R^2)$, —$N(R^2)SO_2$phenyl, or —$N(R^2)SO_2R^2$;

$R^2$ is selected from: hydrogen, methyl, ethyl, propyl, isopropyl, butyl, isobutyl, t-butyl;

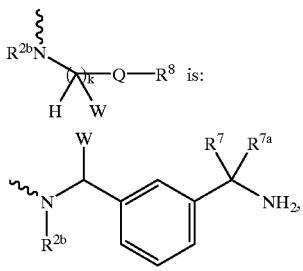

and the phenyl or cycloalkyl groups can be optionally substituted with 1 to 2 R2, 1 to 3 halogen, —$OR^2$, —$CON(R^2)_2$, —$C(O)OR^2$, $C_1$–$C_4$ alkyl, —$S(O)_mR^2$, $N(R^2)_2$, or $CF_3$; and in the case where diastereo- or regio-isomers are present, all are included;

W is selected from the group consisting of: hydrogen, $C_1$–$C_4$ alkyl or $(CH_2)_qC(O)OR^2$;

$R^7$ and $R^{7a}$ are independently trifluoromethyl or $R^2$;

$R^{2b}$ is selected from hydrogen, $C_1$–$C_4$ alkyl, $(CH_2)_nCF_3$ or $(CH_2)t$ heteroaryl;

E is selected from the group consisting of —CO—, —C(=N—CN)—, and —$SO_2$—;

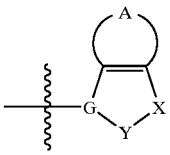

is a member selected from the group consisting of:

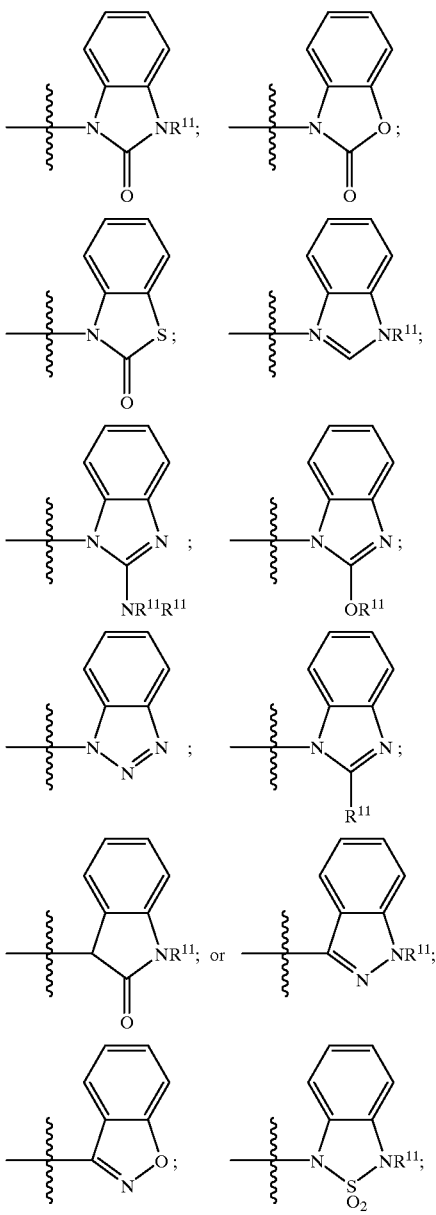

where the aromatic can be optionally substituted with 1–3 groups of $C_1$–$C_6$ alkyl, halogen, —$OR^2$, $N(R^2)_2$, methylenedioxy, —$S(O)_m R^2$, —$CF_3$, —$OCF_3$, nitro, —$N(R^2)C(O)(R^2)$, —$C(O)OR^2$, —$C(O)N(R^2)_2$, —1H-tetrazol-5-yl, —$SO_2N(R^2)_2$, —$N(R^2)SO_2$ phenyl, $N(R^2)C(O)N(R^2)$ or —$N(R^2)SO_2R^2$;

$R^{11}$ is H, $C_1$–$C_8$ alkyl, $CF_3$, $CH_2CF_3$, —$(CH_2)_p OR^2$, —$(CH_2)_p N(R^2)_2$, $(CH_2)_p N(R^2)C(O)N(R^2)_2$, —$(CH_2)_p N(R^2)C(O)R^2$, $(CH_2)_p$ heteroaryl, $(CH_2)_p N(R^2)SO_2C_1$–$C_4$ alkyl, —$(CH_2)_p C(O)N(R^2)_2$, or —$(CH_2)_p C(O)OR^2$ where heteroaryl is tetrazole, oxadiazole, imidazole or triazole which are optionally substituted with $R^2$, $OR^2$, CF3 or $N(R^2)_2$ and where p is 0–3;

m is an integer from 0 to 2;
n is an integer from 0 to 3; and
q is an integer from 0 to 3.

Also included in the invention is a pharmaceutical composition which is comprised of a compound of formula I in combination with a pharmaceutically acceptable carrier.

The invention also includes a method of treating diabetes, cancer, acromegaly chronic atrophic gastritis, Crohn's disease, ulcerative colitis, retinopathy, arthritis, viseral and neuropathic pain and to prevent restenosis, which comprises administering to a person or animal a compound of formula I in an amount which is effective for treating said disease or condition.

The invention is described herein in detail using the terms defined below unless otherwise specified.

The term "alkyl" refers to a monovalent alkane (hydrocarbon) derived radical containing from 1 to 15 carbon atoms unless otherwise defined and if two carbon atoms or more they may include a double or a triple bond. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

and

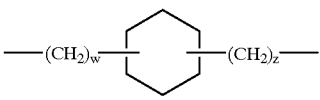

wherein: x plus y=from 0–10 and w plus z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

The term "alkoxy" refers to those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halogen" is intended to include the halogen atom fluorine, chlorine, bromine and iodine.

Aryl refers to aromatic rings e.g., phenyl, substituted phenyl and like groups as well as rings which are fused, e.g., naphthyl, indaryl, biphenyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted with from 1 to 3 groups of $C_1$–$C_{15}$ alkyl, halogen, —$OR^2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, — 1H-tetrazol-5-yl, —$SO_2N(R^2)_2$, —$N(R^2)SO_2$ phenyl or —$N(R^2)SO_2R^2$. Preferred substituted aryls include phenyl and naphthyl substituted with one or two groups.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups selected from 1 to 3 of $C_1$–$C_8$ alkyl, halogen, —$OR^2$, methylenedioxy, —$S(O)_mR^2$, —$CF_3$, —$OCF_3$, $N(R^2)_2$, nitro, —$N(R^2)C(O)(R^2)$, —$C(O)OR^2$, —$C(O)N(R^2)_2$, —1H-tetrazol-5-yl, —$SO_2N(R^2)_2$, —$N(R^2)SO_2$ phenyl or —$N(R^2)SO_2R^2$.

Heteroaryl thus includes aromatic and partially aromatic groups which contain one or more heteroatoms. Examples of this type are thiophene, oxadiazole, imidazopyridine, pyridine, oxazole, thiazole, pyrazole, tetrazole, imidazole, pyrimidine, pyrazine, benzothienyl, benzofuranyl, indolyl, azaindole, benzimidazolyl, quinolinyl, isoquinolinyl and triazine.

The terms "heterocycloalkyl" and "heterocyclyl" refer to a cycloalkyl group (nonaromatic) in which one of the carbon atoms in the ring is replaced by a heteroatom selected from O, S, SO, $SO_2$ or N, and in which up to three additional carbon atoms may be optionally replaced by heteroatoms.

Heterocyclyl is carbon or nitrogen linked; if carbon linked and contains a nitrogen, then the nitrogen may be substituted by $R^2$. Examples of heterocyclyls are piperidinyl, morpholinyl, pyrrolidinyl, tetrahydrofuranyl, tetrahydroimidazo[4,5-c]pyridinyl, imidazolinyl, piperazinyl, pyrolidin-2-onyl, piperidin-2-onyl and the like.

Certain of the above defined terms may occur more than once in the above formula and upon such occurrence each term shall be defined independently of the other.

Salts encompassed within the term "pharmaceutically acceptable salts" refer to non-toxic salts of the compounds of this invention which are generally prepared by reacting the free base with a suitable organic or inorganic acid. Representative salts include the following:

Acetate, Benzenesulfonate, Benzoate, Bicarbonate, Bisulfate, Bitartrate, Borate, Camsylate, Carbonate, Citrate, Dihydrochloride, Edetate, Edisylate, Estolate, Esylate, Fumarate, Gluconate, Glutamate, Hydrobromide, Hydrochloride, Hydroxynaphthoate, Lactate, Lactobionate, Laurate, Malate, Maleate, Mandelate, Mesylate, Mucate, Napsylate, Nitrate, N-methylglucamine ammonium salt, Oleate, Oxalate, Pamoate (Embonate), Paimitate, Pantothenate, Phosphate/diphosphate, Polygalacturonate, Salicylate, Stearate, Sulfate, Subacetate, Succinate, Tannate, Tartrate, Tosylate, and Valerate.

The compounds of the present invention may contain one or more asymmetric carbon atoms and may exist in racemic and optically active forms. All of these compounds are contemplated to be within the scope of the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention. In the case of the asymmetric carbon atom represented by an asterisk in Formula I, it has been found that compounds are more active as somatostatin agonists and, therefore preferred, in which the nitrogen substituent is above and the $R^{1a}$ is below the plane of the structure as represented in Formula II. An equivalent representation places $R^1$ and the N-substitutent in the plane of the structure with the C=O group above. This configuration corresponds to that present in a D-amino acid. In most cases, this is also designated an R-configuration, although this will vary according to the value of $R^1$ used in making R- or S-stereochemical assignments. In addition, configurations of some of the most preferred compounds of this invention are indicated. When the carbon atom in Formula I bearing an asterisk is of a defined and usually a D- configuration, up to two times more diastereomers result with each additional stereo centers are present. These diastereomers are arbitrarily referred to as diastereomer 1 ($d_1$) and diastereomer 2 ($d_2$) and so on as so forth in this invention and, if desired, their independent syntheses or chromatographic separations may be achieved as described herein. Their absolute stereochemistry may be determined by the x-ray crystallography of crystalline products or crystalline intermediates which are derivatized, if necessary, with a reagent containing an asymmetric center of known absolute configuration.

Formula II

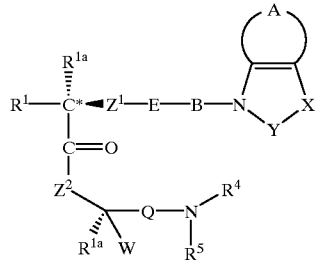

The term "pharmacologically effective amount" shall mean that amount of a drug or pharmaceutical agent that will elicit the biological or medical response of a tissue, system, animal or human that is being sought by a researcher or clinician.

The term "substituted" shall be deemed to include multiple degrees of substitution by a named substitutent.

Where multiple substituent moieties are disclosed or claimed, the substituted compound can be independently substituted by one or more of the disclosed or claimed substituent moieties, singly or plurally.

The ability of the compounds of the present invention to act as somatostatin agonists makes them useful as pharmacologic agents for mammals, especially for humans, for the treatment and prevention of disorders wherein somatostatin itself or the hormones it regulates may be involved. Examples of such disorders include diabetes, acromegaly restenosis, arthritis and cancer. The instant compounds can also be used in combination with other therapeutic agents. Illustrated for diabetes, examples of these compounds include metformin or other biguanides, acarbose, sulfonylureas thiazolidinediones or other insulin sensitizers including, but not limited to, compounds which function as agonists on peroxisome proliferator-activated receptor gamma (PPAR-gamma), insulin, insulin-like-growth factor I, glucagon-like peptide I (glp-I) and available satiety-promoting agents such as dexfenfluramine or leptin.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Intravenous dosages or oral dosages of the compounds of the present invention, when used for the indicated effects, will range between about 0.001 to 5 mg/kg and 0.1 to 50 mg/kg, respectively. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Throughout the instant application, the following abbreviations are used with the following meanings:

| | |
|---|---|
| Bu | butyl |
| Bn | benzyl |
| BOC, Boc | t-butyloxycarbonyl |
| BOP | Benzotriazol-1-yloxy tris/dimethylamino)-phosphonium hexafluorophosphate |
| calc. | calculated |
| CBZ, Cbz | Benzyloxycarbonyl |
| CDI | N,N'-carbonyl diimidazole |
| DCC | Dicyclohexylcarbodiimide |
| DCM | dichloromethane |
| DIEA | diisopropylethylamine |
| DMF | N,N-dimethylformamide |
| DMAP | 4-Dimethylaminopyridine |
| DSC | N,N'-disuccinimidyl carbonate |
| EDC | 1-(3-dimethylaminopropyl)-3-ethylcarbodi-imide hydrochloride |
| EI-MS | Electron ion-mass spectroscopy |
| Et | ethyl |
| EtOAc | ethyl acetate |
| EtOH | ethanol |
| eq. | equivalent(s) |
| FAB-MS | Fast atom bombardment-mass spectroscopy |
| HOAc | acetic acid |
| HOBT, HOBt | Hydroxybenztriazole |
| HPLC | High pressure liquid chromatography |
| KHMDS | Potassium bis(trimethylsilyl)amide |
| LAH | Lithium aluminum hydride |
| LHMDS | Lithium bis(trimethylsilyl)amide |
| Me | methyl |
| MeOH | methanol |
| MF | Molecular formula |
| MHz | Megahertz |
| MPLC | Medium pressure liquid chromatography |
| NMM | N-Methylmorpholine |
| NMR | Nuclear Magnetic Resonance |
| Ph | phenyl |
| Pr | propyl |
| prep. | prepared |
| TFA | Trifluoroacetic acid |
| THF | Tetrahydrofuran |
| TLC | Thin layer chromatography |
| TMS | Trimethylsilane |

The instant compounds can be effective to inhibit the secretion of various hormones and trophic factors in mammals. They may be used to suppress certain endocrine secretions, such as GH, insulin, glucagon and prolactin, in the treatment of disorders such as acromegaly; endocrine tumors such as carcinoids, vipomas, insulinomas and glucagonomas; or diabetes and diabetes-related pathologies, including retinopathy, neuropathy and nephropathy. The compounds may also be used to suppress exocrine secretions in the pancreas, stomach and intestines, for treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the instant compounds include cancers of the breast, prostate, and lung (both small cell and non-small cell epidermoids), as well as hepatomas, neuroblastomas, colon and pancreatic adenocarcinomas (ductal type), chondrosarcomas, and melanomas, and also atherosclerosis associated with vascular grafts and restenosis following angioplasty.

The compounds of the instant invention are further useful to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; and allergies, including asthma. The compounds can also function as neuromodulators in the central nervous system, with useful applications in the treatment of Alzheimer's disease and other forms of dementia, pain (as a spinal analgesic), and headaches. Furthermore, in disorders involving the splanchnic blood flow, including cirrhosis and oesophagal varices, the compounds of the invention can provide cytoprotection.

The preparation of compounds of Formula I of the present invention may be carried out in sequential or convergent synthetic routes. In the interest of clarity, the special case of Formula I, where B is 4-piperidinyl and A is a fused benzo ring as being unsubstituted (formula IIA), is depicted. Compounds fused with different aromatic or non aromatic rings and/or bearing additional substituents on these rings are readily prepared by minor modification of the methods herein with procedures known in the art. Syntheses detailing the preparation of the compounds of Formula I are presented in the following reaction schemes.

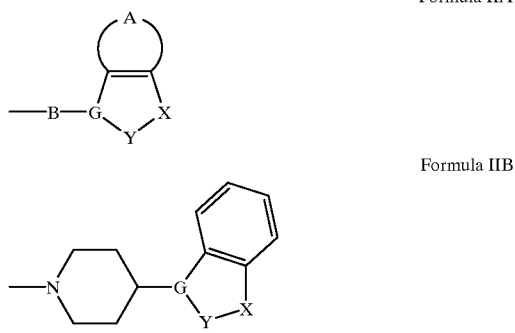

Formula IIA

Formula IIB

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The phrase "mixed urea formation" refers to conversion of two different amines to form their mixed urea by using phosgene or equivalents such as CDI, DSC, or p-nitrophenyl chloroformate. The reaction involves reacting one amine first with the phosgene or equivalents in the presence of a base such as NMM, TEA or DIEA in a inert solvent such as dichloromethane, THF and DMF or mixtures thereof, followed by addition of the second amine and a base such as NMM, TEA or DIEA. The uses of protective groups for amines and carboxylic acids to facilitate the desired reaction and minimize undesired reactions are well documented. Conditions required to remove protecting groups which may be present can be found in Greene, T, and Wuts, P. G. M., *Protective Groups in Organic Synthesis,* John Wiley & Sons, Inc., New York, N.Y. 1991. CBZ and BOC were used extensively and their removal conditions are known to those skilled in the art. For example, removal of CBZ groups can be achieved by a number of methods such as catalytic hydrogenation in the presence of a noble metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethyl sulfide. Removal of BOC protecting groups is carried out in a solvent such as methylene chloride, methanol or ethyl acetate, with a strong acid, such as trifluoroacetic acid, hydrochloric acid or hydrogen chloride gas.

The protected amino acid derivatives required in the synthesis of compounds of Formula 1 are, in many cases, commercially available, where the protecting group ($P^1$) is, for example, methyl, allyl or benzyl groups. Other protected amino acid can be prepared by literature methods (Williams, R. M. *Synthesis of Optically Active α-Amino Acids,* Pergamon Press: Oxford, 1989). Many of the piperidines of Formula 2 are either commercially available or known in the literature and others can be prepared following literature methods described for analogous compounds. Some of these methods are illustrated in the subsequent schemes. Purification procedures include crystallization, normal phase or reverse phase chromatography.

The compounds of the present invention can be prepared readily according to the following Schemes or modifications thereof using readily available starting materials, reagents and conventional synthesis procedures. In these reactions, it is also possible to make use of variants which are themselves known to those of ordinary skill in this art, but are not mentioned in greater detail. The definition for $R^1$, $R^{1a}$, $R^2$, $R^4$, $R^5$, G. Y, X, $Z^1$, $Z^2$, W, Q, E, B, etc., is described above unless otherwise stated.

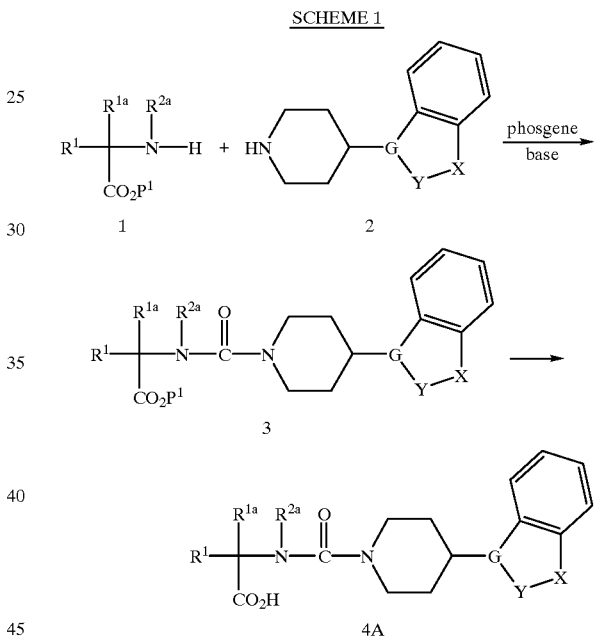

SCHEME 1

Intermediates of Formula 4A can be synthesized as described in Scheme 1. Mixed urea formation between the protected amino acid 1 and the piperidine of Formula 2, is conveniently carried out under usual urea formation reactions use phosgene or equivalents such as CDI, DSC, or p-nitrophenyl chloroformate. Removal of the $P^1$ protecting group can be achieved by saponification for most esters, or by catalytic hydrogenolysis when $P^1$ is benzyl, or by palladium (0) based homogeneous catalysis when $P^1$ is allyl. Intermediate 4A can be used as a common intermediate for the synthesis of somatostatin agonists with variation of the rest of the molecule of Formula I as shown in Scheme 2.

SCHEME 1A

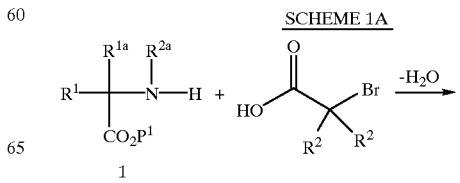

-continued

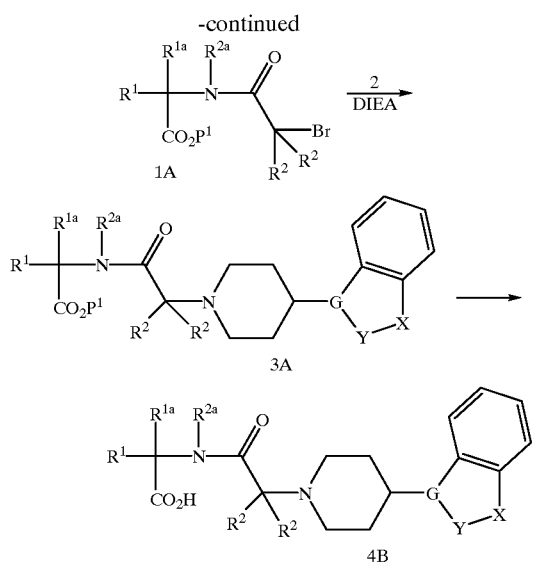

The preparation of amide intermediates of formula 4B can be achieved as shown in Scheme 1A. Standard peptide coupling reactions of protected amino acid 1 with 2-halo acids such as 2-bromoacetic acid gives intermediate 1A, which when reacted with amine of formula 2 gives the compound as 3A in the presence of a non-nucleophilic base such as DIEA. The P1 protecting group can be removed as described above.

Intermediates of Formula 4 can be coupled to intermediates of formula 5 (or formula 6 wherein $R^4$ is $P^2$) wherein $Z^2$ is oxygen or substituted nitrogen to afford compounds of Formula I-A under standard ester or peptide coupling reaction conditions. $P^2$ is an amine protecting group such as BOC, Cbz, etc. Many of the selectively protected diamines or amino alcohol's of Formula 5 are either commercially available or known in the literature and others can be prepared following literature methods described for analogous compounds. Some of these methods are illustrated in subsequent schemes. Also if $R^4$ or $R^5$ is a hydrogen then the protected amino acids 6 are employed in the coupling reaction, wherein $P^2$ is a protecting group as defined above. The removal of $P^2$ in I-A to afford I-B, can be carried out as noted above. $R^4$ as defined above can then be optionally introduced to yield compound of general formula I-C according to procedures known in the art. For example, if R4 is a substituted alkyl group, it can be introduced by reductive amination or opening of epoxide, or by alkylation by an alkyl halide; if R4 is an amidino group, it can be introduced by the reagents such as 1-amidino-3,5-dimethylpyrazole nitrate (Methods Enzymol., 25b, 558, 1972).

SCHEME 2

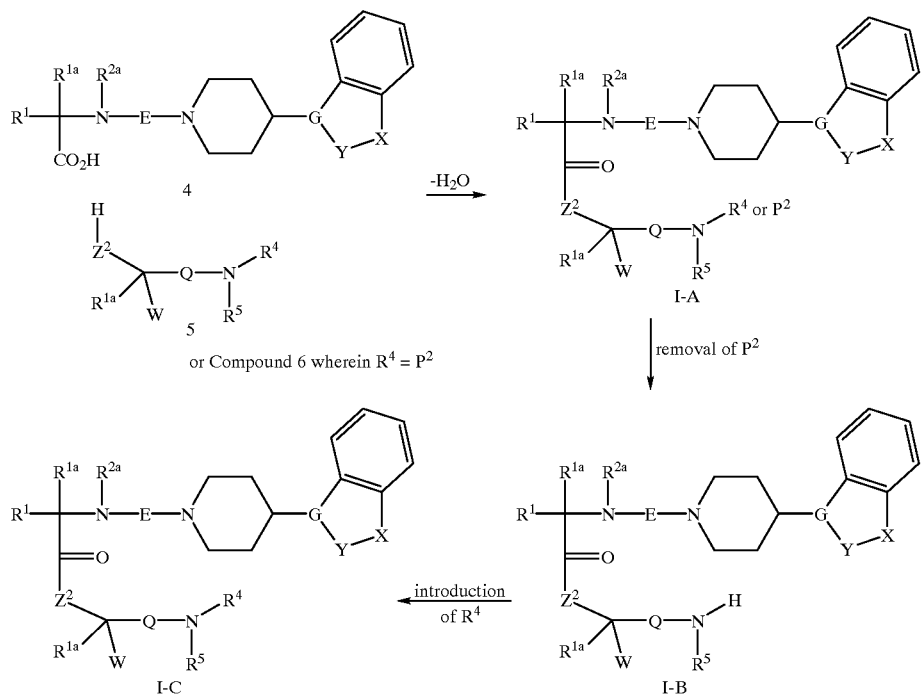

SCHEME 3

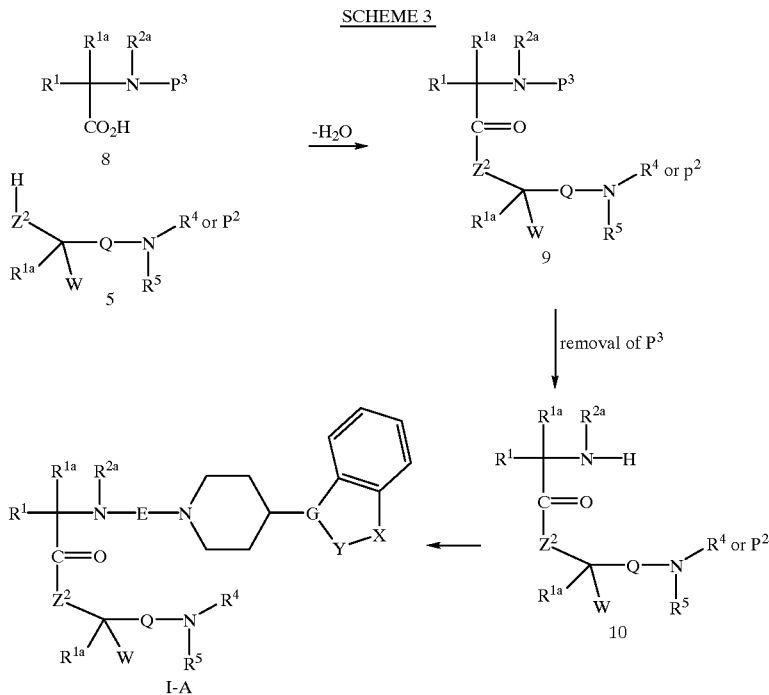

Alternatively, compounds of Formula I can be prepared starting from compound 5. The protected amino acid derivatives 8 are in many cases commercially available, where P3 is, for example, BOC, Cbz, Fmoc, and the like. N-Protected amino acid 8 can be coupled to intermediates of formula 5, wherein $Z^2$ is oxygen or substituted nitrogen to afford compounds of Formula 9 under standard ester or peptide coupling reaction conditions. The protecting group in compound 8 is selected with the criteria that its removal can be achieved without removing $P^2$. When the P2 protecting group is removed to afford compound 10, this compound can be further converted to compounds of formula I-A according to the procedures described in Scheme 1 and Scheme 1A Further elaboration of compound I-A to I-B and I-C are illustrated in Scheme 2.

Formula II

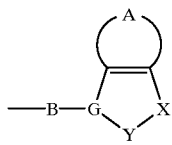

The preparation of compounds of formula II within the scope of this invention may be achieved by methods known in the art. Such methods are illustrated in the following schemes for piperidines with A shown as an unsubstituted fused benzo ring. Analogous methods may be used for the preparation of the other ring compounds or with different substitutions on the ring or both as defined herein. In the interest of clarity, the benzo rings in the following schemes are depicted as being unsubstituted. Compounds bearing additional substituents on the benzo rings are readily prepared by minor modification of the methods herein with procedures known in the art.

SCHEME 4

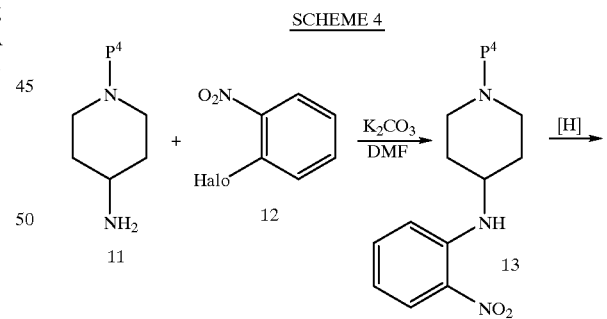

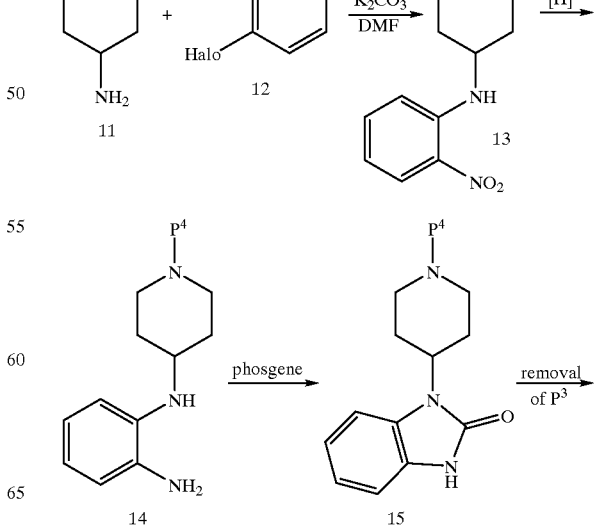

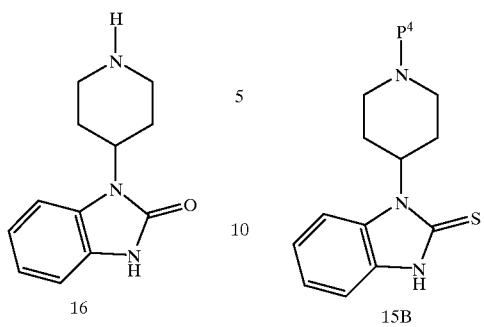

The piperidinylbenzimidazolinone 16 without substitution is commercially available; derivatives with substituents on the benzene ring are prepared by the methods shown in Scheme 4 as described in *J. Med. Chem.*, 30, 814–819 (1987) and U.S. Pat. No. 3,910,930, hereby incorporated by reference. $P^4$ is a protecting group such as benzyl, methyl, BOC, Cbz, ethyloxycarbonyl and the like. Thus, condensation of the commercially available 4-aminopiperidine 11, where $P^4$ is C(O)OEt, with a substituted o-halo nitrobenzene 12 gives the nitro compound 13. Reduction of the nitro group to an amine can be accomplished by catalytic hydrogenation with a catalyst such as Raney Ni, palladium on carbon or platinum on carbon in a protic solvent such as ethanol. Ring closure can be effected by phosgene or its equivalent such as DSC, CDI in the presence of a base. The protecting group $P^4$ can be removed by alkaline hydrolysis in the case of C(O)OEt or can be removed by the standard deprotection conditions as described in Greene, T, and Wuts, P. G. M., *Protective Groups in Organic Synthesis,* John Wiley & Sons, Inc., New York, N.Y. 1991.

Similarly, other groups as defined by Y in compounds of Formula I can be prepared according to the reactions shown in Scheme 5. Thus, cyclic sulfamide 15 A can be prepared by reacting the diamine 14 and sulfamide; reaction of diamine 14 with thiophosgene or equivalents in the presence of a base gives the thiourea 15B; and reaction with cyanogen bromide yields compound 15C. The protecting group $P^4$ can be removed as described above.

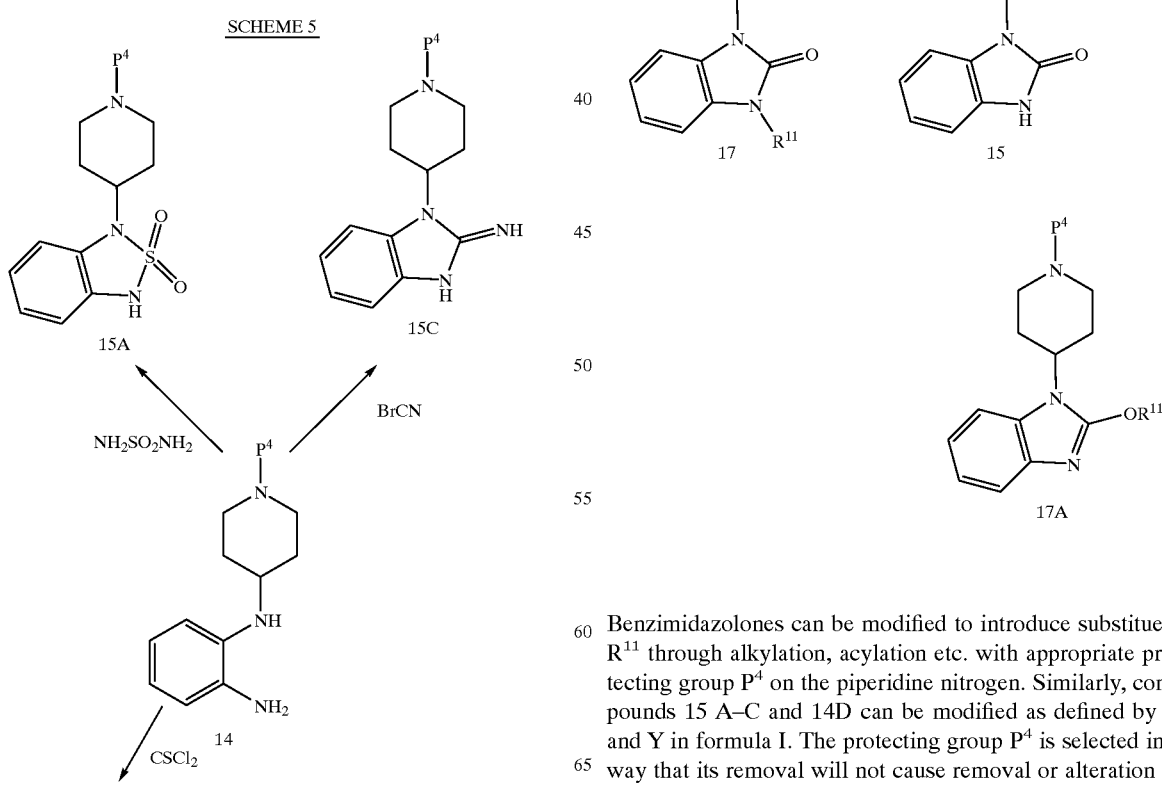

Benzimidazolones can be modified to introduce substituent $R^{11}$ through alkylation, acylation etc. with appropriate protecting group $P^4$ on the piperidine nitrogen. Similarly, compounds 15 A–C and 14D can be modified as defined by X and Y in formula I. The protecting group $P^4$ is selected in a way that its removal will not cause removal or alteration of $R^{11}$.

SCHEME 7

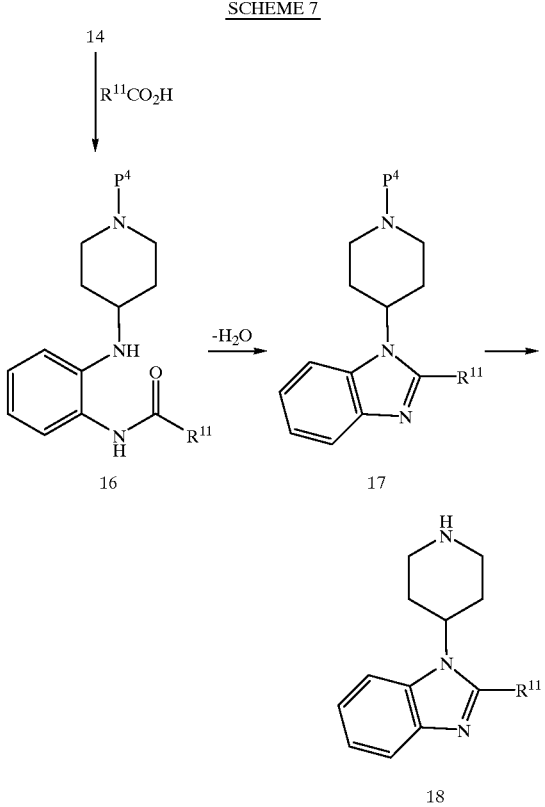

In cases where $R^{11}$ is attached directly to the ring, such compounds can be prepared according to Scheme 7. Coupling compound 14 with a carboxylic acid or equivalents followed by ring closure under dehydration conditions gives compound 17. Removal of the $P^4$ protecting group yields the compound 18.

SCHEME 8

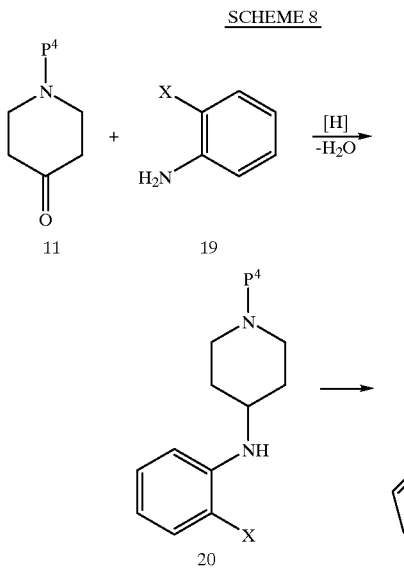

Alternatively, the ortho substituted aniline compound 19, where X is —OH, —NH2, —NR$^{11}$H, —SH, —CH$_2$OH, —CH$_2$NH$_2$, —CH$_2$NR$^{11}$H, —CH$_2$SH etc. can be reductively aminated with a protected 4-piperidinone 11 to afford compound 20. Ring closure can be effected through the chemistry discussed above.

SCHEME 9

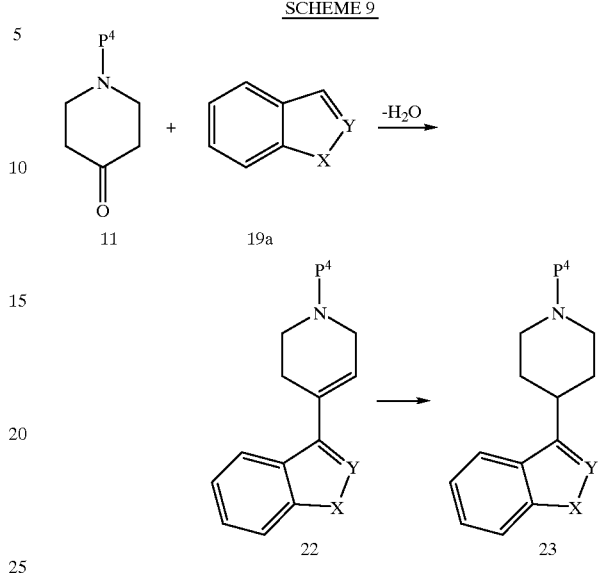

An alternative preparation involves an acid catalyzed coupling reaction of a protected 4-piperidinone 11 with an electron rich aromatic compound such as 19a, where X is O, S, NH or N-alkyl, and Y is CH, COH, COR$^{11}$, CH or N. The resulting 4-substituted tetrahydropyridines 22 obtained by this method can be elaborated to the instant compounds by utilizing chemistry detailed in Schemes 1–8. The 4-substituted tetrahydropyridines 22 can be hydrogenated by use of platinum or palladium catalysts in a protic solvent like methanol to give piperidines of formula 23 which can also be elaborated to the instant compounds of Formula I.

SCHEME 10

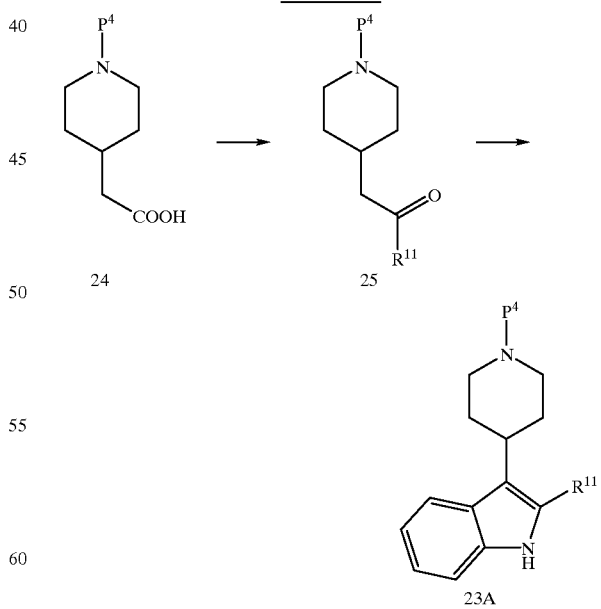

A specific indole embodiment of compound 23, where X=NH and Y=CR$^{11}$ and R$^{11}$ is H or alkyl, can be prepared using a Fisher indole synthesis protocol (see *J. Chem. Soc. Chem. Commun.*, 563 (1981); *J. Chem. Soc.*, 3175 (1957))

starting from a ketone or aldehyde and an aromatic hydrazine. Specifically, piperidines of formula 23A may be prepared from the protected piperidine acetic acid compound 24 as shown in Scheme 10. Conversion of the known carboxylic acid 24 to the corresponding aldehyde or ketones can be effected by a variety of conditions known in the art. For example, treatment of 24 with either oxalyl chloride or thionyl chloride in an inert solvent like benzene or carbon tetrachloride gives the corresponding acid chloride that is converted to the aldehyde 25 ($R^{11}$=H) by a Rosemund reduction. The conversion can also be effected by the Weinreb protocol in which an N,O-dimethyl hydroxylamine amide is reacted with a Grignard reagent to give the ketone or is reacted with LAH to give the aldehyde. Most hydrazines are commercially available or known in the literature and can be prepared accordingly. The condensation of the ketone 25 and hydrazine under the Fisher indole synthesis conditions yields the indole compound 23A. The protecting group $P^4$ can be removed by standard protocols and elaborated to the instant compounds by using chemistry presented in Schemes 1–8.

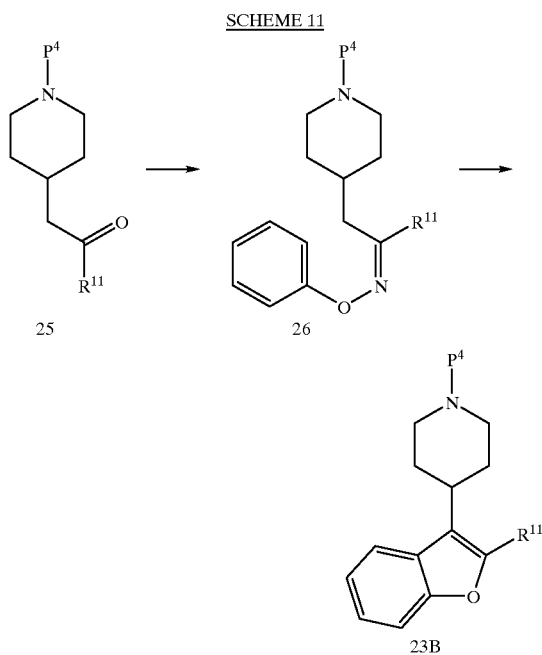

An analogous synthesis of benzofurans of formula 23B from o-aryloximes is exemplified by the transformation of 25 to 26 (see *Tetrahedron Lett.*, 2867 (1967)) as depicted in Scheme 12.

Formula III

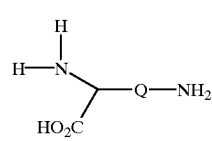

In many cases, compounds of Formula III or its mono protected form within the scopes of this invention are either commercially available or known in the art. In the simplest case where $Z^2$ is NH or O, $R^{1a}$, W, $R^4$ and $R^5$ are H's, Q is —$(CH_2)_x$—V—$(CH_2)_y$—; where x and y are 1–7, the formula represents diamines some of which are commercially available. Mono Boc protected amine can be prepared by reacting excess diamine with $Boc_2O$ in methanol, where Boc protected amino alcohols can be prepared by reacting the amino alcohol with Boc2O.

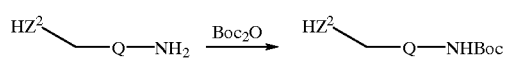

The above procedure is also applicable to compounds of formula III where $R^{1a}$ and W are groups as define defined before.

Formula IV $$\begin{array}{c} H \\ | \\ H-N \\ \diagdown \\ HO_2C \end{array} \!\!\!\!\!\!-\!Q\!-\!NH_2$$

Compounds of Formula IV represent amino acids, which in some cases are commercially available. Amino acids can be modified to give compounds as defined by the scope of the instant application. For example, with the two amino groups properly protected, the carboxylic acid can be converted into its next higher homologue, or to a derivative of the homologous acid, such as amide or ester by an Arndt-Eistert reaction. The acid can also be converted amides with a variety of amines as defined. The acid can be reduced to alhohol, which can be converted to ether by alkylation or reduced with methods know to those skilled in the art.

Optically pure cis-3-aminomethyl-1-BOC-aminomethyl cyclohexane enantiomers are prepared (Scheme 12) starting from commercially available m-cyanobenzoic acid. Reduction of the nitrile with Raney $Ni/H_2$ is followed by protection of the resulting 1° amino group. Reduction of the aromatic ring is then accomplished using $PtO_2$ as catalyst to give predominantly the cis-cyclohexane carboxylic acid. A sequence of crystallizations using either (S) or (R)-a-methylbenzylamine to form the salt, generates the homochiral cis acids as shown below. Enantiomeric purity is evaluated by derivatization of the acids with Trp-OMe and integration of the methoxy methyl singlets in the $^1H$ NMR spectra. The absolute stereochemistries are determined by solving the x-ray structure for the pure salt obtained from crystallization with the S-enantiomer of a-methylbenzylamine and are as shown in Scheme 12 below. Borane reduction of the pure acids, followed by coversion of the resulting alcohols to their mesylates and displacement with azide anion furnishes the corresponding azidomethyl compounds. Reduction of the azide group (Pd/C, $H_2$) gives the desired amines, ready for incorporation into final target compounds.

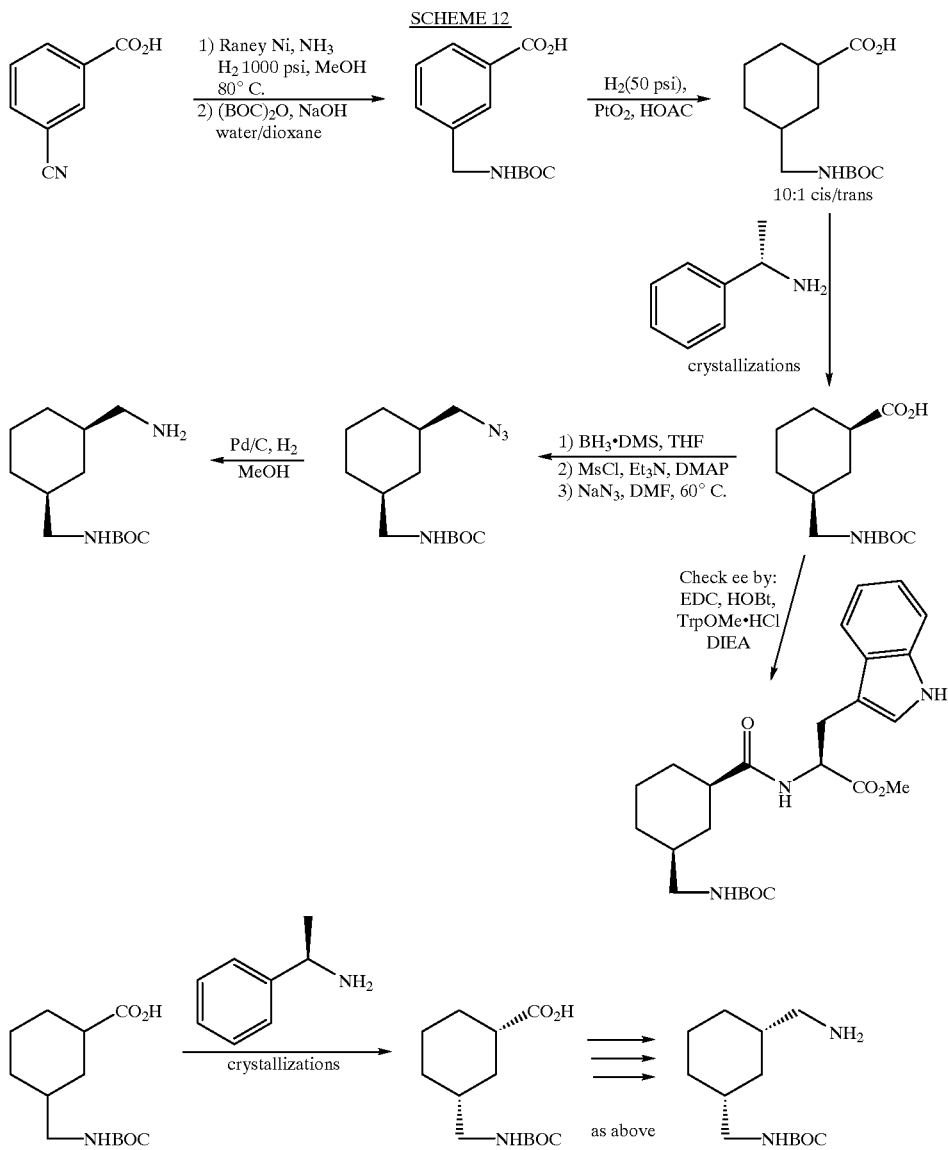

The racemic cis and trans-3-aminomethyl-1-BOC-aminomethyl cyclohexane isomers are also prepared (Scheme 13) and incorporated into target compounds. Commercially available bis-aminomethylcyclohexane (sold as a mixture of cis and trans isomers) is resolved into the pure cis and pure trans isomers by conversion to the dihydrochloride salts and crystallization from methanol/ethyl acetate. Mono-BOC protection is accomplished by slow addition of $BOC_2O$ to an excess of the diamines.

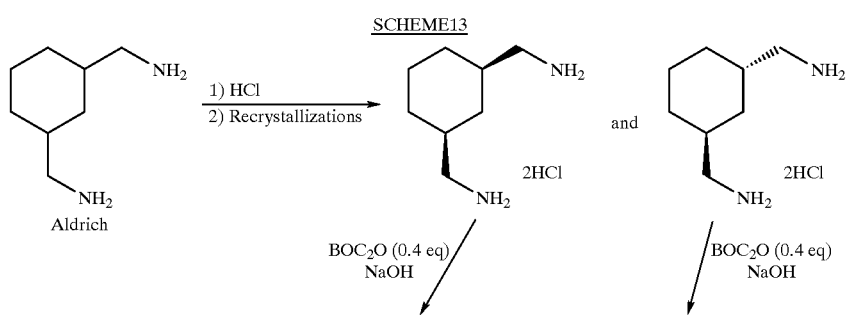

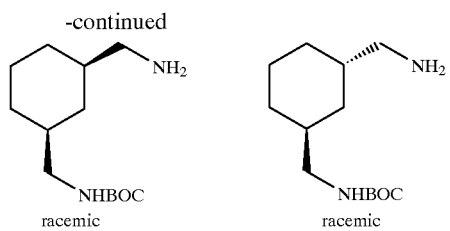

racemic      racemic

Secondary amines derived from homochiral cis-3-aminomethyl-1-BOC-aminomethyl cyclohexane are also introduced into target analogs. These secondary amines are prepared (Scheme 14) starting from the corresponding pure acids (see Scheme 12 for preparation of acids) by conversion to the Wienreb amides, followed by reduction to the corresponding aldehydes. Reductive amination with a variety of amines furnished the secondary amines.

SCHEME 14

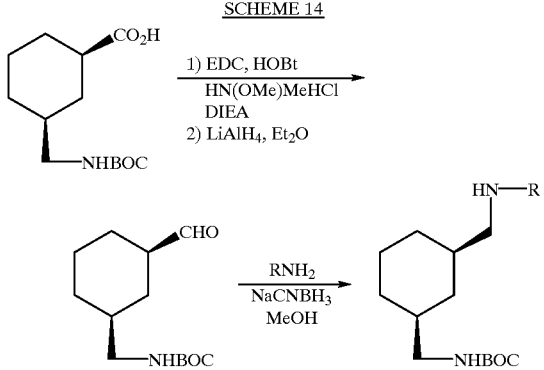

Precursor amines possessing secondary amino functionality at what would ultimately be the terminal amino group in the final target analogs are prepared by various means. For example (Scheme 15), the azide intermediate below (prepared as described in Scheme 12) is deprotonated with KHMDS and alkylated with methyl iodide; reduction of the azide group then provides the N-methyl-N-BOC precursor. Another strategy (Scheme 15) starts with the acid intermediate described earlier. Conversion to the corresponding secondary amines is achieved in the same fashion as described in Scheme 13. Protection of the secondary amine is carried out using Cbz-Cl; removal of the BOC group then gives the N-alkyl-N-Cbz-amines, ready for incorporation into target analogs.

SCHEME 15

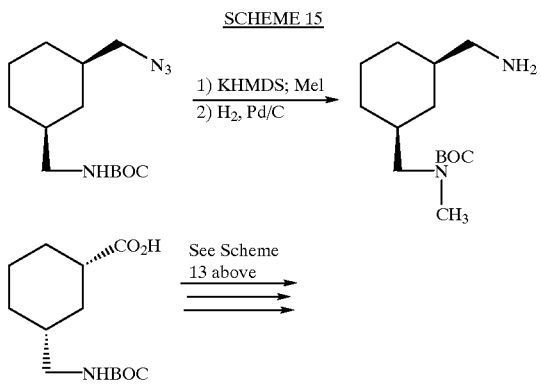

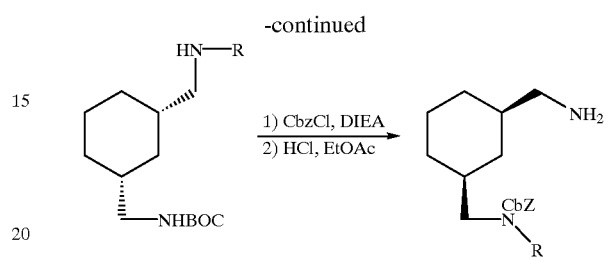

Final target terminating in either tertiary or secondary amines could alternatively be prepared at a later stage of the synthesis (Scheme 16). Fully assembled primary amine-based compounds can be reductively alkylated with aldehydes to give the tertiary amines or alkylated with alkyl halides to give secondary amines.

SCHEME 16

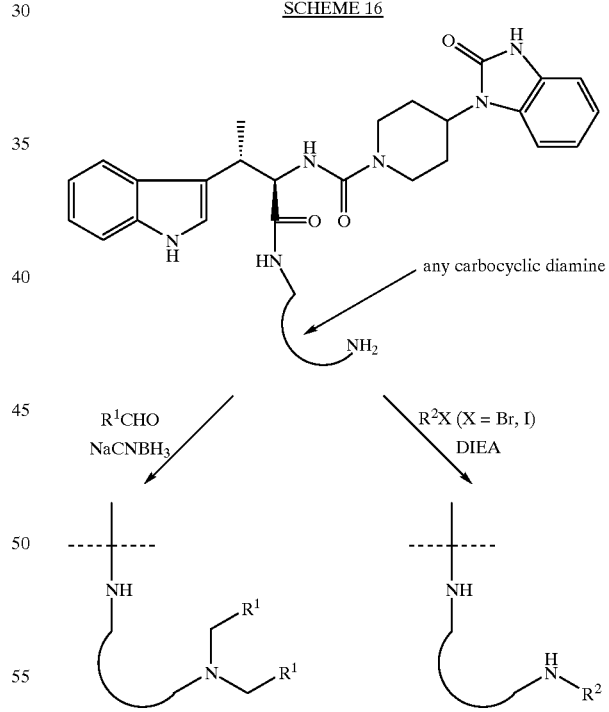

Trans-1-N-BOC-amino-4-aminomethylcyclohexanes are prepared from the commercially available amino acid shown below (Scheme 17). Protection of the amine as its phthalimide, followed by Curtius rearrangement gives the amino-protected isocyanide. Trapping of the isocyanide with t-butanol, is then followed by removal of the phthalimide protecting group using hydrazine to provide the target amine, which is incorporated into various analogs. Reductive alkylation of the free amine with various aldehydes gives secondary amines which are also incorporated into final target analogs.

SCHEME 17

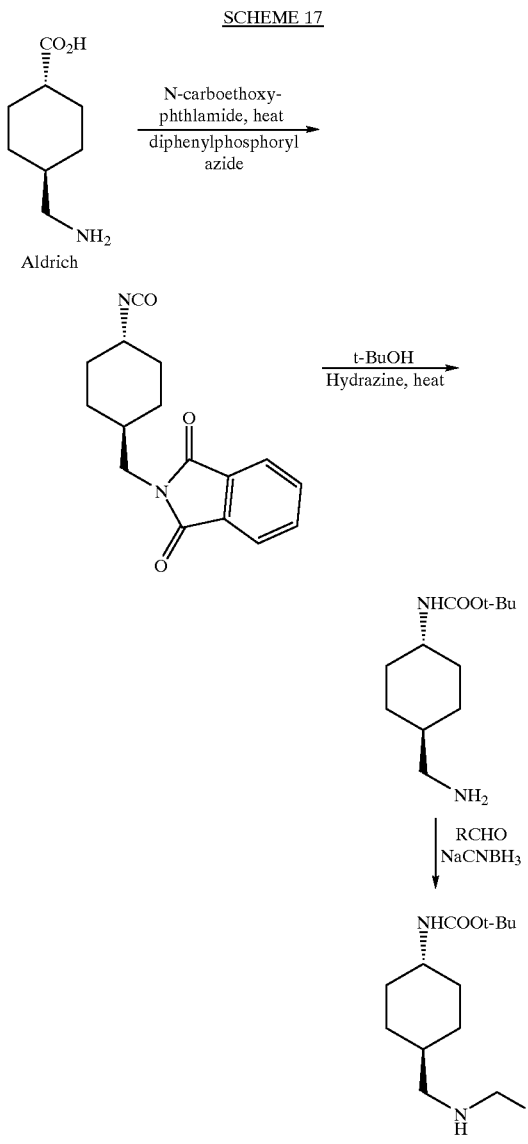

Mono-protected-1,3-bisaminomethylbenzene intermediates also lead to potent analogs. These are prepared (Scheme 18) starting from commercially available m-xylylenediamine. Slow addition of BOC$_2$O to an excess of diamine furnishes the mono-protected amine, which is employed in the synthesis of target compounds. Alternatively, reductive alkylation with a variety of aldehydes gives the corresponding secondary amines.

SCHEME 18

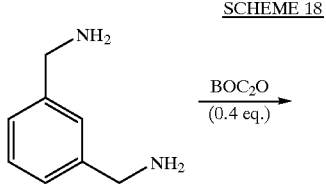

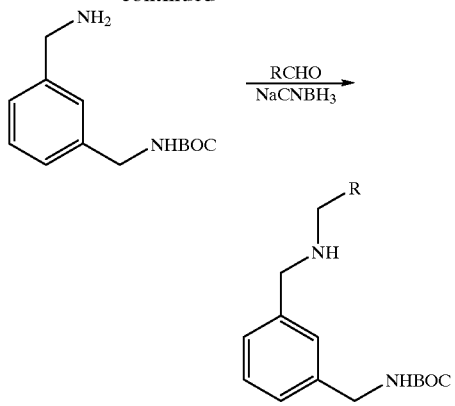

Racemic cis-3-aminomethyl-1-BOC-aminomethylcyclopentane is prepared as shown in Scheme 19. Reduction of the commercially available anhydride give cis-hydroxymethylcyclopentane. Conversion to the bis-mesylate, followed by displacement with azide results in the corresponding bis-azide. Reduction of the mono-protection (as described previously) provides the desired intermediate amine.

SCHEME 19

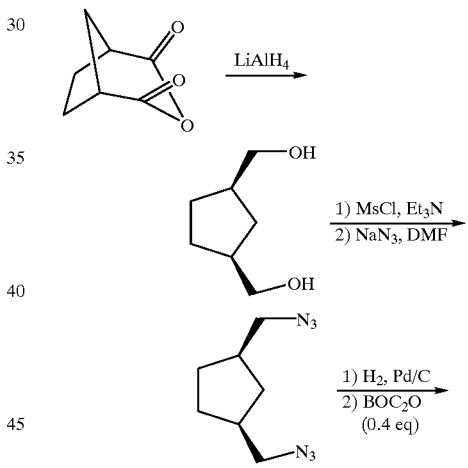

The preferred compounds of the invention are any or all of those specifically set forth in the Examples below. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

INTERMEDIATE 1

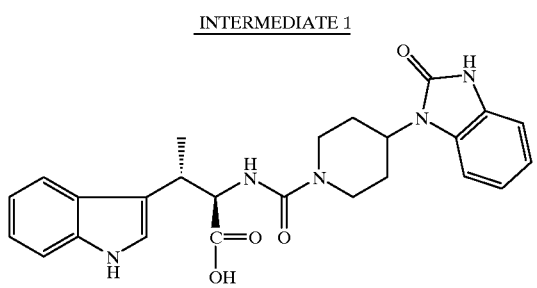

Step A:

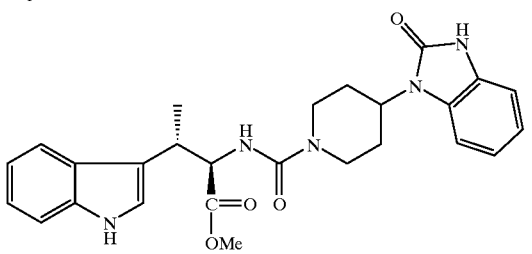

b-Methyl-D-Tryptophan methyl ester (6.00 g, 25.9 mmol) was combined with disuccinimidyl carbonate (6.95 g, 27.1 mmol) and DIEA (11.3 mL, 64.6 mmol) in dichloromethane. After stirring the reaction mixture for 0.5 h, 4-(2-keto-1-benzimidazolinyl)-piperidine (5.90 g, 27.1 mmol) was added and the mixture was permitted to stir over night. The reaction mixture was diluted with dichloromethane, and washed in succession with 1N HCl (100 mL), saturated NaHCO$_3$ solution (100 mL) and brine (100 mL), dried over MgSO$_4$, filtered and concentrated. The resulting crude product was purified by MPLC (silica, 5% methanol/ethyl acetate) to give 7.55 g of a white solid.

Step B:

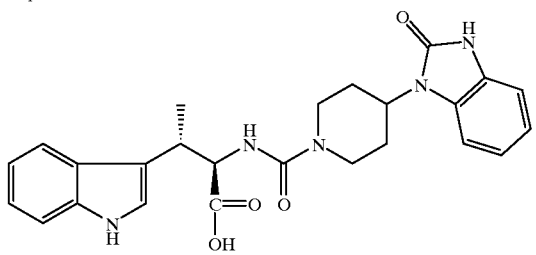

The coupled product from the previous step (7.55 g, 15.9 mmol) was dissolved in THF (30 mL), treated with LiOH (2.67 g, 63.6 mmol) in 1:1 EtOH/water (60 mL) and stirred for 4h at room temperature. The pH was adjusted to ~2–3 by addition of 3N HCl and the resulting solution was extracted with ethyl acetate 3 times. The combined organic layers were washed with brine, dried over MgSO$_4$, filtered and concentrated to give 6.50 g of a white solid.

INTERMEDIATE 2a, 2b (both enentiomers)

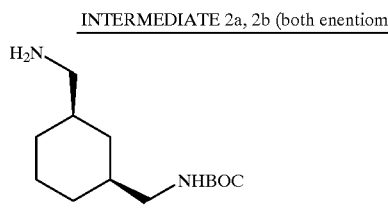

Step A:

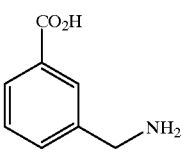

Commercially available m-cyanobenzoic acid (38 g, 0.26 mol) was dissolved in methanol (350 mL). Raney Ni (2 g) was added and 75 mL of NH$_3$ was condensed into the vessel. The resulting mixture was agitated at 80° C. under 1000 psi H$_2$ for 16 h. The mixture was filtered through celite and concentrated. The crude product was used in the following step.

Step B:

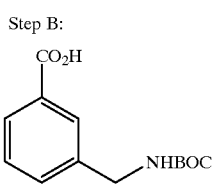

To the crude product from the above step (0.26 mol) was added a solution of NaOH (18.7 g, 0.468 mol) in water (200 mL). Then BOC$_2$O (62 g, 0.28 mol) in p-dioxane (200 mL) was added via addition funnel over 0.5 h. After an additional 2 h the reaction mixture was concentrated to remove the dioxane and then washed twice with DCM (200 mL). The aqueous phase was acidified by slow addition of conc. HCl while cooling in an ice bath. Some gas evolution indicated the presence of residual Raney Ni. The aqueous mixture was then extracted twice with ether (200 mL). The combined ethereal extracts were washed with 1N HCl (200 mL), and brine (200 mL), dried over MgSO$_4$, filtered and concentrated to afford 33.3 g of a white solid.

Step C:

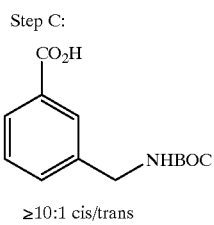

≥10:1 cis/trans

To a solution of the product from the previous step (10.0 g, 39.8 mmol) in glacial acetic acid (40 mL) was added PtO$_2$ and the resulting mixture was agitated under 50 psi H$_2$ for overnight. The reaction mixture was filtered through celite and the filter cake was further washed with two portions of methanol (50 mL each). The filtrate was concentrated. The remaining acetic acid was removed by toluene/acetic acid azeotrope. The product (13.15 g) was collected as a white solid. 1HNMR analysis indicated that the product was ≧10:1 cis/trans.

CI-MS calc. for $C_{13}H_{23}NO4$: 257; Found 258 (M+H).

Step D:

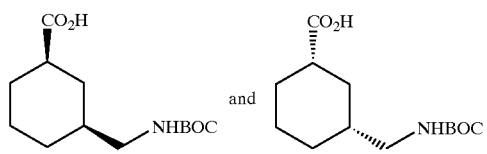

The racemic product of the above reaction (78 g, 0.30 mol) was combined with (39 mL, 0.30 mol) in hot ethyl acetate. Slow cooling to room temperature with gentle stirring and continued stirring overnight afforded crystals. The above was repeated four times (pure seed crystals from an earlier purification facilitated more efficient purification). The resulting salt was partioned between ethyl acetate and 3N HCl. The organic layer was washed with brine, dried over $MgSO_4$, filtered and concentrated to afford 9.3 g of optically enhanced acid. The purity of the acid was found to be ≧20:1 by derivatization as described below. The absolute stereochemistry of both stereocenters was established by x-ray crystallographic analysis of the final pure (S)-a-methylbenzylamine salt (see below) as being (R) alpha to the carboxyl group and (S) alpha to the BOC-aminomethyl group. The combined mother liquors from the above purification were converted back to free acid as described above. Three recrystallizations of the acid recovered from the ML were carried out in the same fashion using (R)-a-methylbenzylamine to give (after extractive removal of the amine) 9.6 g of free acid of the opposite absolute stereochemistry as for the initial batch described above. Again, the purity was demonstrated to be ≧20:1 by $^1$H NMR analysis of a derivative.

Determination of optical-purity:

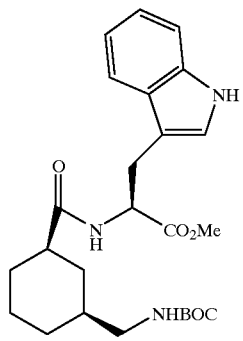

A small sample of the acid purified as described above (10.8 mg, 0.0420 mmol) was combined with H-Trp-OMe.HCl (14 mg, 0.055 mmol), EDC (12 mg, 0.063 mmol), HOBt (9.0 mg, 0.063 mmol) and DIEA (10 mL, 0.055 mmol) in DCM (1 mL). The resulting solution was allowed to stir at rt for 3h at which time no acid starting material could be detected by TLC analysis. The reaction mixture was diluted with DCM (10 mL) and washed sequentially with 1N HCl (3×5 mL), saturated $NaHCO_3$ solution (3×5 mL) and brine (5 mL), dried over $MgSO_4$, filtered and concentrated. $^1$H NMR analysis of the crude product indicated an isomer ratio of ~25:1 by integration of the singlet signals arising from the Lys-OMe group.

$^1$H NMR (CDCl$_3$, 400 MHz) d 8.35 (br s, 1H), 7.50 (d, J=7.6 Hz, 1H), 7.35 (d, J=7.6 Hz, 1H), 7.17 (t, J=7.6 Hz, 1H), 7.09 (t, J=7.6 Hz, 1H), 6.94 (d, J=1.5 Hz, 1H), 5.95 (d, J=7.6 Hz, 1H), 4.91 (m, 1H), 4.59 (br s, 1H), 3.69 (s, 3H), 3.31 (dd, J=6.1, 15.2 Hz, 2H), 3.00 (m, 1H), 2.83 (m, 1H), 1.99 (m, 1H), 1.86-1.60 (m, 5H), 1.44 (s, 9H), 1.31-1.12 (m, 2H), 0.98 (q, J=11.4 Hz, 1H), 0.82 (m, 1H).

Step E:

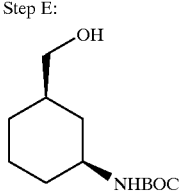

The pure (3S)-BOC-aminomethyl cyclohexane-(1R)-carboxylic acid (495 mg, 1.92 mmol) was dissolved in THF (5 mL), cooled to 0° C. and treated dropwise with a 2M solution of $BH_3$.DMS in THF (1.6 mL, 3.2 mmol). After an additional 5 min at 0° C. the temperature was permitted to warm to rt and the reaction mixture was stirred for 1.5 h. Water was then added dropwise to quench thew remaining borane. When gas evolution ceased the reaction mixture was diluted with ethyl acetate (75 mL) and washed sequentially with 1N HCl (50 mL), and brine (50 mL). The organic layer was dried over $MgSO_4$, filtered and concentrated to afford the crude product (534 mg) which was used without further purification. The alcohol of the opposite absolute stereochemistry was prepared in the same way.

$^1$H NMR (CDCl$_3$, 400 MHz) d 4.60 (br s, 1H), 3.42 (m, 2H), 2.94 (m, 2H), 1.82-1.68 (m, 5H), 1.48 (m, 1H), 1.41 (s, 9H), 1.23 (m, 1H), 0.82 (m, 2H), 0.58 (q, J=12.4 Hz, 1H).

Step F:

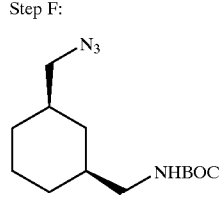

To a solution of the alcohol prepared as described above (445 mg, 1.83 mmol) in DCM (10 mL) at 0° C. was added triethylamine (510 mL, 3.66 mmol) and DMAP (ca. 50 mg, catalytic), followed in turn by methane sulfonyl chloride (160 mL, 2.01 mmol). After 1.5 h the reaction mixture was diluted with DCM (75 mL) and washed sequentially with 1N HCl (2×50 mL), saturated $NaHCO_3$ solution (2×50 mL), and brine (50 mL). The organic layer was dried over $MgSO_4$, filtered and concentrated to provide the mesylate product (594 mg) which was used immediately in the following reaction. A solution of the mesylate (590 mg, 1.83 mmol) and $NaN_3$ (238 mg, 3.66 mmol) in DMF (5 mL) was stirred at 65° C. for 7 h. The reaction mixture was diluted with ether (60 mL) and washed five times with water (40 mL each) and once with brine (40 mL). The ethereal layer was dried over $MgSO_4$, filtered and concentrated to give 422.7 mg of crude product. The azide of the opposite absolute stereochemistry was prepared in the same fashion from the corresponding alcohol.

$^1$H NMR (CDCl$_3$, 400 MHz) d 4.58 (br s, 1H), 3.12 (dd, J=6.4, 1.6 Hz, 2H), 2.95 (m, 2H), 1.82-1.68 (m, 4H), 1.57 (m, 2H), 1.42 (s, 9H), 1.24 (m, 1H), 0.93-0.76 (m, 2H), 0.62 (q, J=12 Hz, 1H).

Step G:

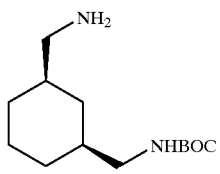

The intermediate prepared as described above (409 mg, 1.53 mmol) was combined with 10% Pd/C (80 mg) in methanol (12 mL). This mixture was stirred under a $H_2$ balloon for 6 h, then filtered through celite. The filter cake was washed with an additional 50 mL of methanol and the combined filtrates were concentrated. Flash chromatography (silica, 1.5% $NH_4OH$ solution, 13.5% MeOH, 85% DCM) afforded the pure amine (264.1 mg). $[\alpha]^{22}D=-5.2°$ (c 0.78, $CHCl_3$).

$^1H$ NMR ($CDCl_3$, 400 MHz) d 4.61 (br s, 1H), 2.93 (m, 2H), 2.50 (dd, J=6.4, 2.4 Hz, 2H), 1.80-1.66 (m, 4H), 1.50 (app br s, 2H), 1.40 (s, 9H), 1.25 (m, 2H), 0.79 (m, 2H), 0.52 (q, J=12.4 Hz, 1H).

INTERMEDIATE 2c, 2d (trans and cis, racemic)

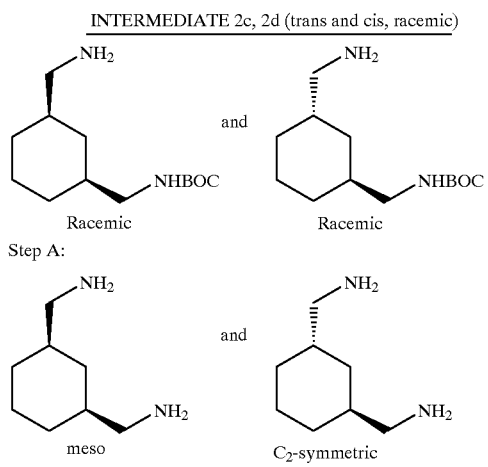

Commercially available 1,3-bis(aminomethyl) cyclohexane (200 g, 1.41 mol), sold as a mixture of isomers, was dissolved in isopropanol (1 L) and treated with concentrated HCl (12N, 240 mL, 2.88 mol). After the addition was complete the solvent was removed and the residue was crystallized from hot ~1:1 methanol/ethyl acetate. Material enhanced in the trans isomer crystallized first. Several recrystallizations of salt obtained from the mother liquor, however, furnished 76.4 g of 10:1 cis/trans diamine hydrochloride(determined by $^1H$ NMR). By checking crystals and ML's by $^1H$ NMR and following up with additional recrystallizations a small quantity of diamine enhanced in trans was also obtained (~1:8 cis/trans).

$^1H$ NMR trans isomer ($CD_3OD$, 400 MHz) d 2.91 (dd, J=7.5, 1.1 Hz, 4H), 2.01 (m, 2H), 1.71 (m, 2H), 1.58 (app t, J=6Hz, 4H), 1.38 (m, 2H).

$^1H$ NMR cis isomer ($CD_3OD$, 400 MHz) d 2.86 (dd, J=13, 6.5 Hz, 2H), 2.79 (dd, J=13, 7.6 Hz, 2H), 1.90-1.82 (m, 3H), 1.74 (m, 2H), 1.58 (m, 1H), 1.38 (m, 1H), 0.99 (m, 2H), 0.79 (q, J=12 Hz, 1H).

Step B:

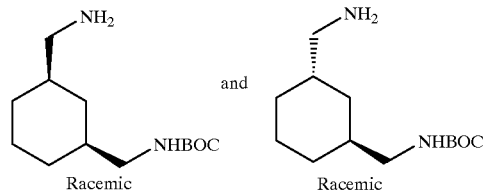

For cis compound: The meso diamine dihydrochloride prepared as described above (6.5 g, 30 mmol) was dissolved in methanol (75 mL) and NaOH (1.27 g, 31.7 mmol) was added. When all reagents were fully dissolved a solution of $BOC_2O$ (2.68 g, 12.1 mmol) in p-dioxane (20 mL) was added via addition funnel dropwise over 1.25 h. After the addition the reaction mixture was stirred for an additional 3.5 h and then the solvents were evaporated under reduced pressure. The residue was dissolved in DCM (100 mL) and washed in turn with saturated $NaHCO_3$ solution (75 mL), water (75 mL) and brine (75 mL), dried over $Na_2SO_4$, filtered and concentrated to afford the product (2.94 g, 100%). The trans mono BOC compound was prepared in an identical fashion.

Cis: $^1H$ NMR ($CDCl_3$, 400 MHz) d 4.60 (br s, 1H), 2.93 (m, 2H), 2.51 (m, 2H), 1.80-1.66 (m, 4H), 1.57 (m, 2H), 1.41 (s, 9H), 1.24 (m, 1H), 0.80 (m, 2H), 0.52 (q, J=12.1 Hz, 1H).

Trans: $^1H$ NMR ($CDCl_3$, 400 MHz) d

ESI-MS calc. for C13H26N2O2: 242; Found: 243 (M+H).

INTERMEDIATE 3

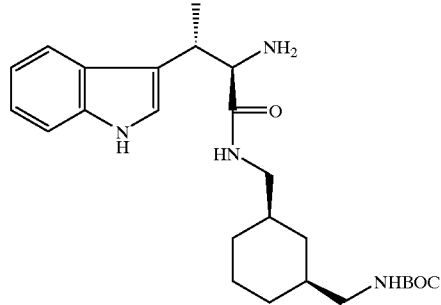

Step A:

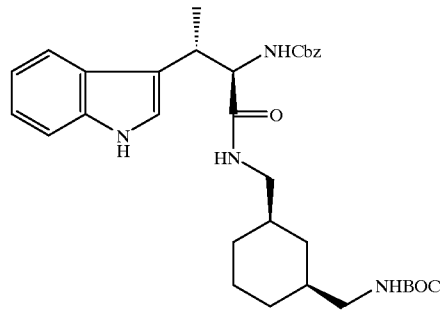

To a mixture of (3R)-aminomethyl-(1S)-BOC-aminomethylcyclohexane (2a above, 1.46 g, 6.04 mmol), beta-methyl Trp (2.03 g, 6.04 mmol), and HOBt (1.47 g, 10.9 mmol) in DCM (50 mL) was added at 0° C. EDC (2.08 g, 10.9 mmol). The reaction mixture was then permitted to warm to rt and stir overnight. The reaction mixture was diluted with more DCM (150 mL) and washed in turn with 1N HCl (100 mL), saturated $NaHCO_3$ solution (100 mL) and brine (100 mL), dried over $MgSO_4$, filtered and concentrated. Purification by MPLC (silica, 70% ethyl acetate/hexane) afforded 2.40 g (69%) of the product as a white solid.

ESI-MS calc. for C33H44N4O5: 576; Found: 577 (M+H).

Step B:

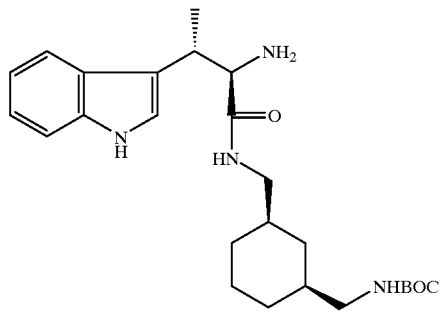

The intermediate from the previous step (2.40 g, 4.16 mmol) was dissolved in methanol (50 mL) and stirred under H$_2$ (g) in the presence of catalytic Pd/C (10%, 240 mg) for 1.25 h. The reaction mixture was filtered through celite, the filter cake was washed with additional methanol and the combined filtrates were concentrated to give 1.82 g (99%) of the desired product.

$^1$H NMR (CDCl$_3$, 400 MHz) d 8.76 (br s, 1H), 7.72 (d, J=7.6 Hz, 1H), 7.36 (d, J=8.4 Hz, 1H), 7.17 (app t, J=8.4 Hz, 1H), 7.11-6.97 (m, 2H), 4.68 (t, J=5.2 Hz, 1H), 3.76 (m, 2H), 3.12 (m, 1H), 3.00 (m, 1H), 2.86-2.78 (m, 2H), 1.90 (m, 4H), 1.69 (m, 2H), 1.59 (m, 1H), 1.44 (s, 9H), 1.33 (d, J=6.8 Hz, 3H), 1.19 (m, 2H), 0.71 (m, 2H), 0.37 (q, J=12 Hz, 1H).

ESI-MS calc. for C25H38N4O3: 442; Found: 443 (M+H).

INTERMEDIATE 4

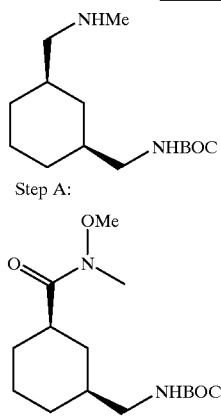

Step A:

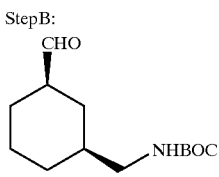

The pure (3S)-BOC-aminomethyl cyclohexane-(1R)-carboxylic acid (3.93 g, 15.3 mmol), prepared as described above, was combined with N-methyl-O-methyl-hydroxylamine hydrochloride (2.98 g, 30.6 mmol), HOBt (4.13 g, 30.6 mmol) and DIEA (5.90 mL, 33.6 mmol) in DCM (100 mL). The resulting solution was cooled to 0° C. and treated with EDC (5.86 g, 30.6 mmol). The reaction mixture was allowed to warm to rt and then stirred for 2 h. The reaction mixture was diluted with DCM (200 mL) and washed with saturated NAHCO$_3$ solution (2×100 mL), 1N HCl (2×100 mL) and brine (100 mL). The organic layer was dried over MgSO$_4$, filtered and concentrated to provide 4.52 g of crude product.

Step B:

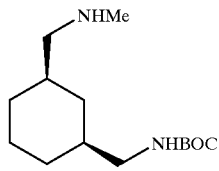

The product from the previous step (1.93 g, 6.42 mmol) was dissolved in anhydrous ether (150 mL), cooled to 0° C., and treated with 1.0 M LiAlH$_4$.2THF in toluene (8.03 mL, 8.03 mmol) dropwise over 5 min. After an additional 1 h, the reaction was quenched by dropwise addition of water until bubbling ceased. The reaction mixture was then washed with 1N HCl (2×100 mL), saturated NaHCO$_3$ solution (100 mL) and brine (100 mL). The ethereal layer was dried over MgSO$_4$, filtered and concentrated to afford the product (1.53 g, 99%) as an oil. $^1$H NMR (CDCl$_3$, 400 MHz) d 9.61 (d, J=2 Hz, 1H), 4.63 (br s, 1H), 3.00 (m, 2H), 2.23 (m, 1H), 2.04-1.83 (m, 3H), 1.78 (m, 2H), 1.53-1.08 (m, 2H), 1.44 (s, 9H), 0.88 (m, 2H).

Step C:

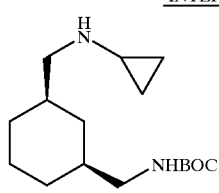

The aldehyde prepared in the previous step (2.98 g, 12.4 mmol) was combined with methylamine hydrochloride (2.50 g, 37.0 mmol) and NaOAc (15.2 g, 185 mmol) in methanol (100 mL). After 15 min NaCNBH$_3$ (2.33 g, 37.0 mmol) was added and the mixture was stirred overnight at rt. The solvent was then removed and the residue was dissolved in DCM (150 mL) and washed with saturated NaHCO$_3$ solution (2×100 mL), and brine (2×100 mL). The organic layer was dried over MgSO$_4$, filtered and concentrated. Flash chromatographic purification (silica, 1.5% NH$_4$OH solution, 13.5% methanol/DCM) afforded 778.4 mg of pure product.

$^1$H NMR (CDCl$_3$, 400 MHz) d 4.61 (br s, 1H), 2.97 (m, 2H), 2.45 (m, 2H), 2.43 (s, 3H), 2.13 (br s, 2H), 1.78 (m, 4H), 1.49 (m, 1H), 1.43 (s, 9H), 1.27 (m, 1H), 0.88 (m, 2H), 0.59 (q, J=16 Hz, 1H).

INTERMEDIATE 5

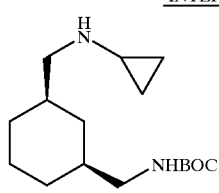

In a similar fashion as described for the preparation of intermediate 4, the aldehyde used in that synthesis (intermediate 4, Step B, 124 mg, 0.516 mmol) was combined with cyclopropylamine (88.0 mg, 1.55 mmol) and acetic acid (dropwise addition until pH=7) in methanol (5 mL). Then NaCNBH$_3$ (52 mg, 0.83 mmol) was added and the mixture was permitted to stir overnight at rt. The reaction mixture was then concentrated, diluted with DCM (25 mL)

and washed with saturated NaHCO₃ solution (2×10 mL), and brine (2×10 mL). The organic layer was dried over MgSO₄, filtered and concentrated to afford the desired 2° amine as an oil (127.5 mg, 88%).

ESI-MS calc. for C16H30N2O2: 282; Found: 283 (M+H).

INTERMEDIATES 6–12

Intermediates 6 through 12 (shown in the below table) were prepared in the same fashion as described for either Intermediate 4 or Intermediate 5.

| Intermed. | Structure | ESI—MS | Intermed. | Structure | ESI—MS |
|---|---|---|---|---|---|
| 6 | 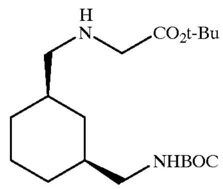 | calc. for C19H36N2O4: 356 Found: 357 (M + H) | 10 | 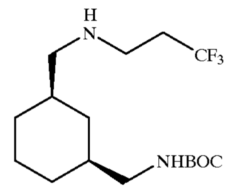 | calc. for C16H29N2O2-F3: 338 Found: 339 (M + H) |
| 7 | 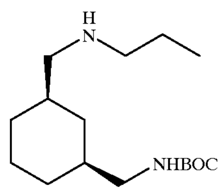 | calc. for C16H32N2O2: 284 Found: 285 (M + H) | 11 | 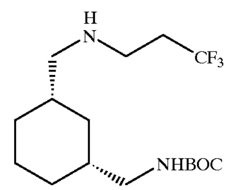 | |
| 8 | 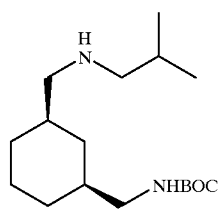 | calc. for C17H34N2O2: 298 Found: 299 (M + H) | 12 | 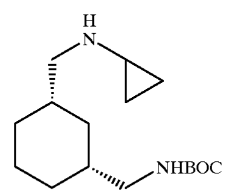 | |
| 9 | 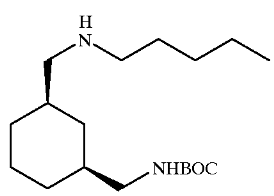 | calc. for C18H36N2O2: 312 Found: 313 (M + H) | | | |

INTERMEDIATE 13

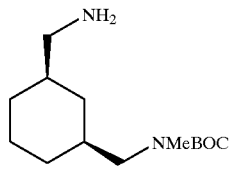

Step A:

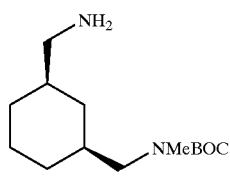

(3R)-Azidomethyl-(1S)-BOC-aminomethylcyclohexane (275 mg, 1.03 mmol), prepared as described above, was dissolved in THF (5 mL), cooled to 0° C. and treated with 0.5M KHMDS in toluene (4.1 mL, 2.1 mmol) dropwise over 3 min. After an additional 15 min, methyl iodide (128 mL, 2.05 mmol) was added and the reaction mixture was permitted to warm to rt and stir for 1.3 h. The reaction mixture was then diluted with ethyl acetate (50 mL) and washed with 1N HCl (40 mL), saturated NaHCO$_3$ solution (40 mL) and brine (40 mL). The organic layer was dried over MgSO$_4$, filtered and concentrated to afford 295 mg of product as an oil.

$^1$H NMR (CCDl$_3$, 400 MHz) d 3.12 (m, 2H), 3.03 (m, 2H), 2.82 (br s, 3H), 1.82-1.50 (m, 6H), 1.42 (s, 9H), 1.22 (m, 1H), 0.83 (m, 2H), 0.62 (br q, J=12 Hz, 1H).

Step B:

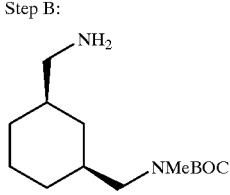

The product from the previous step (291 mg, 1.03 mmol) was combined with 10% Pd/C (60 mg) in methanol (10 mL) and stirred under H$_2$ (g), introduced via balloon, overnight. The reaction mixture was then filtered through celite and the filtercake was washed with additional methanol (30 mL). The combined filtrates were concentrated to afford 256.6 mg of crude product.

ESI-MS calc. for C14H28N2O2: 256; Found: 257 (M+H).

INTERMEDIATE 14

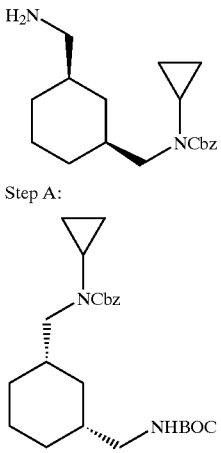

Intermediate 12 (106 mg, 0.374 mmol), prepared as described above, was combined with DIEA (91 mL, 0.52 mmol) in DCM (5 mL) and the resulting solution was cooled to 0° C. and treated with Cbz-Cl (61 mL, 0.43 mmol) dropwise. The reaction mixture was warmed to rt and stirred for 2h. To hydrolyze the remaining Cbz-Cl, water (5 mL) and DMAP (~10 mg) were added and the mixture was stirred for an additional 0.5 h. The reaction mixture was then diluted with DCM (40 mL) and washed with 1N HCl (40 mL), saturated NaHCO$_3$ solution (40 mL) and brine (40 mL). The organic layer was dried over MgSO$_4$, filtered and concentrated to afford 142.3 mg of product.

Step B:

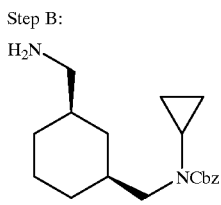

The product of the previous reaction (142 mg, 0.341 mmol) was dissolved in ethyl acetate (10 mL) and HCl (g) was bubbled through the resulting solution for 3–4 min. The solvent was removed to give 117.5 mg of product.

$^1$H NMR (CD$_3$OD, 300 MHz) d 7.37 (m, 5H), 5.12 (s, 2H), 3.17 (d, J=7.5 Hz, 2H), 2.75 (d, J=6.6 Hz, 2H), 2.60 (m, 1H), 1.90-1.55 (m, 7H), 1.29 (m, 2H), 0.92 (m, 2H), 0.78 (m, 1H), 0.63 (m, 2H).

INTERMEDIATE 15

N-(4-tertbutoxycarbonylamino)cyclohexylmethyl amine

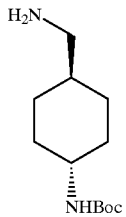

Step 1: N-(trans-4-Carboxycyclohexylmethyl)phthalimide

N-carboethoxyphthalimide (21.9 g, 0.10 mol), trans-4-(aminomethyl)cyclohexane carboxylic acid (15.7 g, 0.10 mol) and triethylamine (14 mL) were stirred in 100 mL THF and the mixture refluxed 18 hours. The nearly clear solution was poured into 400 ml water containing 10 mL glac. HOAc with rapid stirring and the precipitated product collected by suction and dried in a vacuum oven at 80° C., mp 190–192°.

Step 2: N-(trans-4-Isocyanato-cyclohexylmethyl) phthalimide

The product from the previous step was stirred in 200 ml CCl$_4$ containing 10 mL SOCl$_2$ and the mixture refluxed under a drying tube until the solution remained clear on cooling and gas evolution ceased. The mixture was concentrated in vacuo to 100 ml and treated with 14.0 mL trimethylsilyl azide at reflux for 18 hours. The resulting solution was concentrated to give the crude title isocyanate.

Step 3: N-(4-tertbutoxycarbonylamino)cyclohexylmethyl phthalimide

The crude product from example 1, step 2 was treated with a solution of lithium tert butoxide in THF for 2 hours at room temperature to give a dark solution which was diluted with aqueous acetic acid and ice to precipitate the crude product which is recrystallized from 1-chlorobutane to give beige needles of the title urethane, mp. 163–165°.

Step 4: N-(4-tertbutoxycarbonyamino)cyclohexylmethyl amine

The above urethane phthalimide was treated with 1 equivalent anhydrous hydrazine in isopropanol for 18 hours at room temperature followed by 4 hours reflux. The mixture was concentrated, diluted with cold aqueous acetic acid and filtered to remove phthalazinedione. The aqueous layer was basified with NaOH followed by extraction with ethyl acetate, drying, and evaporation to afford the desired product Intermediate 1 as a solid.

INTERMEDIATE 16

Some of the instant compounds can be prepared employing solid phase methodology, the general procedure for which is described below:

Preparation of resin-bound diamine or amino-alcohol:

Transferred 1.8 g of Rapp Tentagel HMPB resin (0.20 mmol/g, see FIG. 1) to a fritted tube and washed with 30 mL of 1:1 THF/CH$_2$Cl$_2$. Added 9 mL of a 0.75M solution of DIEA in THF/CH$_2$Cl$_2$. Added 9 mL of a 0.75M solution of p-nitrophenylchloroformate in THF/CH$_2$Cl$_2$. Agitated for 6 hours. Drained the tube and washed the resin with 2×30 mL of THF/CH$_2$Cl$_2$. Added 18 mL of a 0.25M DMF solution of a 1:1 mixture of diamine or amino-alcohol (see Table 1) and DIEA and agitated for 16 hours. Drained the tube and washed the resin with 4×20 mL of DMF.

FIG. 1. Rapp Tentagel HMPB Resin

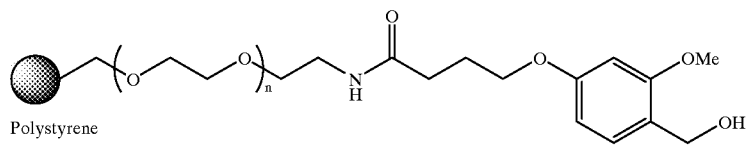

Transferred 25 mg of diamine or amino-alcohol loaded resin (see FIG. 2 and Table 1) into a fritted tube. Washed the resin with 2×1.5 mL of DMF. Added 250 μL of a 0.52M solution of Fmoc-(RS,SR)-b-methyltryptophan in DMF. Added 250 μL of a 0.52M solution of DIC/3% DMAP in DMF. Agitated the reaction vessel for 3 hours. Drained the tube and washed the resin with 2×1.5 mL of DMF and repeated the acylation. Drained the tube and washed the resin with 3×1.5mL of DMF. Added 500 μL of 20% piperidine in DMF and agitated for 30 minutes. Drained and washed the resin with 2×1.5 mL each of DMF and 1:1 THF/CH$_2$Cl$_2$. Added 250 μL of a 0.5M solution of DIEA in THF/CH$_2$Cl$_2$. Added 250 μL of a 0.5M solution of p-nitrophenylchloroformate in THF/CH$_2$Cl$_2$. Agitated for 30 minutes. Drained the tube and washed the resin with 2×1.5 mL of THF/CH$_2$Cl$_2$. Added 500 μL of a 0.25M solution of 1:1 4-(2-keto-1-benzimidiazolinyl)piperidine/DIEA in DMF and agitated for 20 minutes. Drained the tube, and washed the resin with 3×1.5 mL each of DMF, THF/CH$_2$Cl$_2$, THF, CH$_2$Cl$_2$, isopropanol, CH$_2$Cl$_2$, and glacial acetic acid. Added 1 mL of glacial acetic acid under nitrogen, and heated to 40° C. for 21.5 hours to release the compound from the resin. Drained the tube, collecting the solution. Lyophilized this solution to afford the product. Mass Spectroscopy confirms the presence of the desired product (See Table II below).

EXAMPLE 1

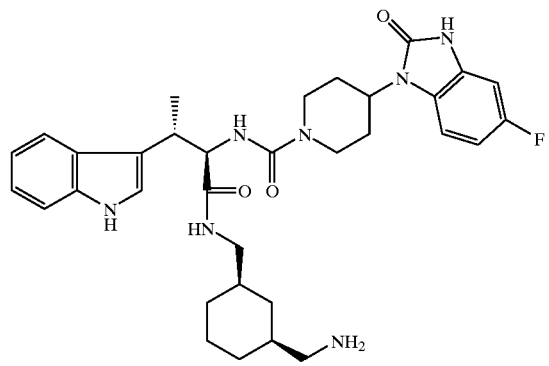

FIG. 2.

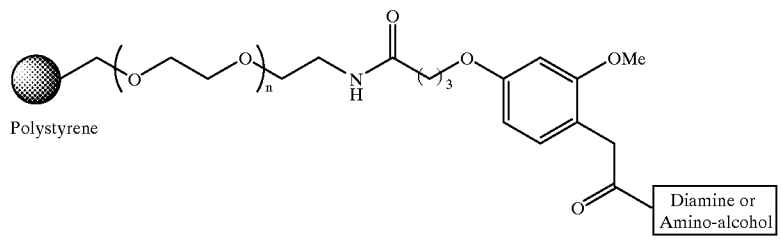

Step A:

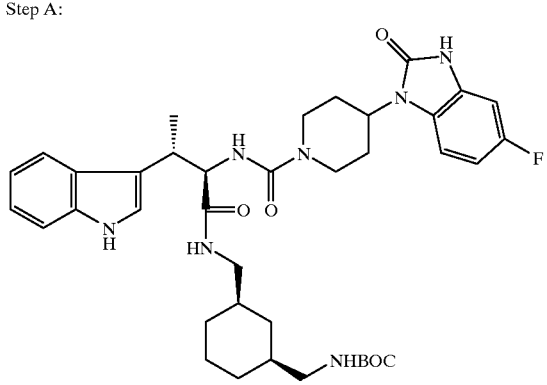

Intermediate 3 prepared as described above (100 mg, 0.226 mmol) was dissolved in DCM (10 mL) and treated with disuccidimidyl carbonate (DSC, 58.0 mg, 0.237 mmol) and DIEA (0.250 mL, 1.35 mmol). After about 40 min. 4-(fluoro-2-keto-1-benzimidazolinyl)-piperidine hydrochloride (64 mg, 0.27 mmol) was added and the resulting mixture was allowed to stir at rt overnight. The reaction mixture was then diluted with DCM (40 mL) and washed with 1N HCl (2×30 mL), saturated $NaHCO_3$ solution (30 mL) and brine (30 mL), dried over $MgSO_4$, filtered and concentrated. The crude product was purified by MPLC (silica, 5% methanol/ethyl acetate) to afford 110 mg of pure product.

Step B:

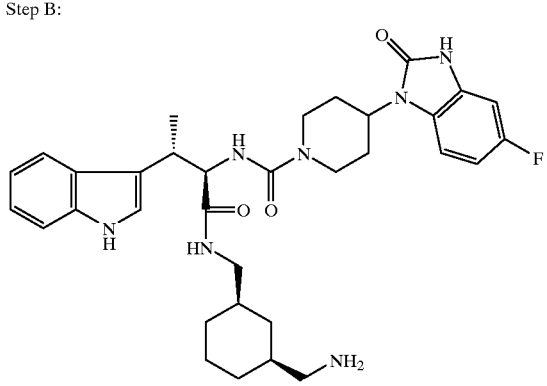

The product from the previous step (109 mg, 0.155 mmol) was dissolved in ethyl acetate (15 mL) and HCl gas was bubbled through the solution for 2 min. The reaction mixture was concentrated to give the product as its HCl salt.

ESI-MS calc. for C33H42N7O3F: 603; Found 604 (M+H).

EXAMPLE 2

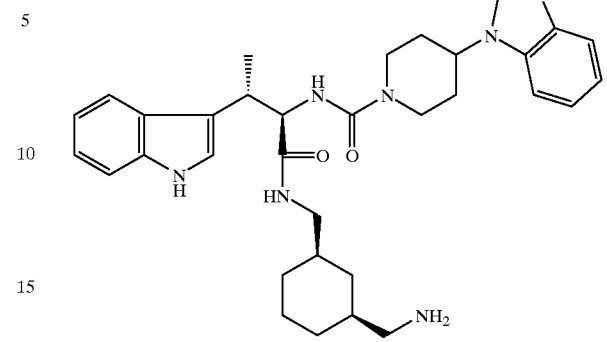

Step A:

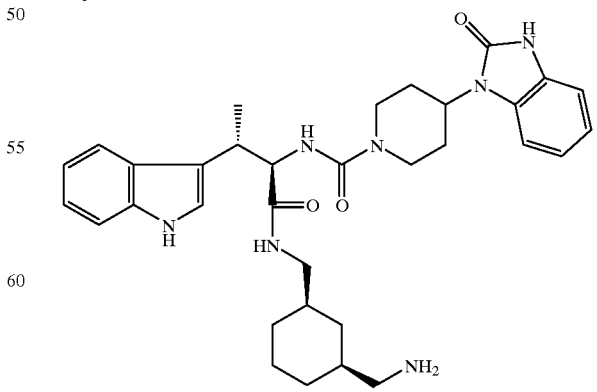

Carboxylic acid 1 (82.1 mg, 0.178 mmol), prepared as described above, was combined with (3R)-aminomethyl-(1S)-BOC-aminomethylcyclohexane (2a above, 43.1 mg, 0.178 mmol), and HOBt (34.5 mg, 0.267 mmol) in DCM (5 mL). The mixture was cooled to 0° C. and EDC (51.2 mg, 0.267 mmol) was added. The reaction mixture was allowed to warm to rt and stir for 2.5 h. Dilution with DCM (40 mL) was followed by washing with 1N HCl (20 mL), saturated $NaHCO_3$ solution (20 mL) and brine (20 mL). The organic phase was dried over $MgSO_4$, filtered and concentrated to yield an oil which was purified by MPLC (silica, 5% methanol/ethyl acetate) to afford a white solid (105.0 mg, 86%).

Step B:

The intermediate prepared in the previous step (90 mg, 0.13 mmol) was dissolved in DCM (5 mL) and treated with TFA (5 mL). After 0.5 h at rt the reaction mixture was concentrated and acetic acid (5 mL) was added. The solution was subjected to lyophilization to give the product as a pink/white solid (acetic acid salt).

$^1$H NMR (CD$_3$OD, 400 MHz) d 7.67 (d, J=8 Hz, 1H), 7.59 (t, J=6.4 Hz, 1H), 7.32 (d, J=8 Hz, 1H), 7.16 (m, 2H), 7.11-6.99 (m, 4H), 4.52 (d, J=9.2 Hz, 1H), 4.47 (m, 1H), 4.22 (m, 2H), 3.56 (m, 1H), 2.98 (m, 3H), 2.69 (m, 1H), 2.51 (m, 2H), 2.45-2.24 (m, 2H), 1.99 (s, 2H), 1.79 (m, 2H), 1.66 (m, 2H), 4.53 (d, J=9.5 Hz, 3H), 1.42-1.25 (m, 3H), 1.11 (m, 2H), 0.68 (dq, J=12, 3.2 Hz, 1H), 0.51 (dq, J=12, 3.2 Hz, 1H), 0.19 (q, J=12 Hz, 1H).

ESI-MS calc. for C33H43N7O3: 585; Found: 586 (M+H).

EXAMPLE 3

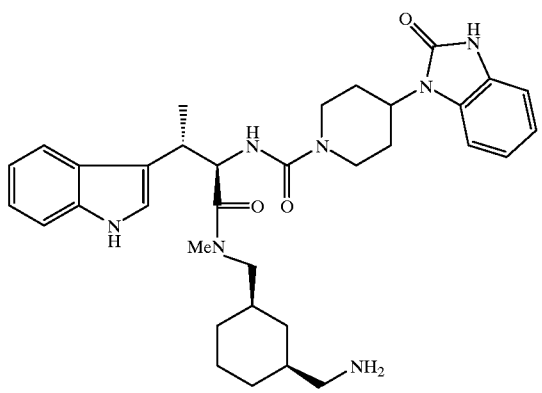

Step A:

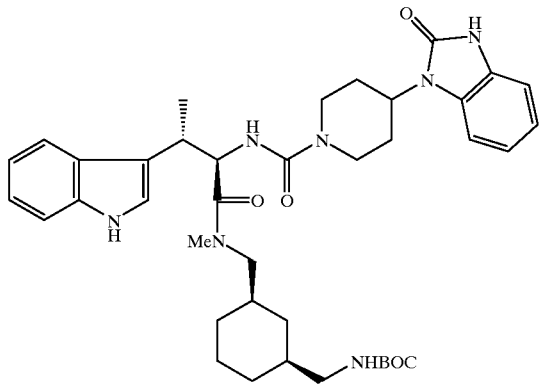

Carboxylic acid 1 (77.2 mg, 0.167 mmol), prepared as described above, was combined with (3R)-aminomethyl-(1S)-BOC-N-methyl-aminomethylcyclohexane (33 mg, 0.13 mmol), prepared as described above, and HOBt (31 mg, 0.23 mmol) in DCM (5 mL). The mixture was cooled to 0° C. and EDC (46 mg, 0.23 mmol) was added. The reaction mixture was allowed to warm to rt and stir overnight. Dilution with DCM (40 mL) was followed by washing with 1N HCl (20 mL), saturated NaHCO$_3$ solution (20 mL) and brine (20 mL). The organic phase was dried over MgSO$_4$, filtered and concentrated to yield an oil which was purified by MPLC (silica, 6.5% methanol/ethyl acetate) to afford a white solid (69.4 mg).

ESI-MS calc. for C39H53N7O5: 699; Found: 700 (M+H).

Step B:

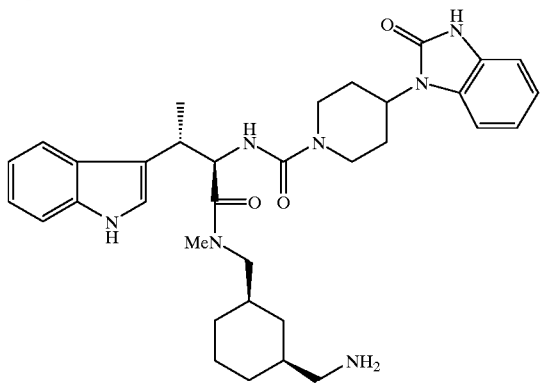

The intermediate from the previous step (69 mg, 0.099 mmol) was dissolved in 5:1 ethyl acetate/DCM (10 mL) and HCl (g) was bubbled through the resulting solution for 3–4 min. The reaction mixture was concentrated. The crude product was purified by flash chromatography (silica, 1.2% conc. NH$_4$OH, 10.8% methanol/DCM to 1.5% conc. NH$_4$OH, 10.8% methanol/DCM, gradient). The resulting pure free base was converted to its HCl salt by adding 1 equivalent concentrated HCl to a methanolic solution of the free base and concentrating.

ESI-MS calc. for C34H45N7O3: 599; Found: 600 (M+H).

EXAMPLE 4

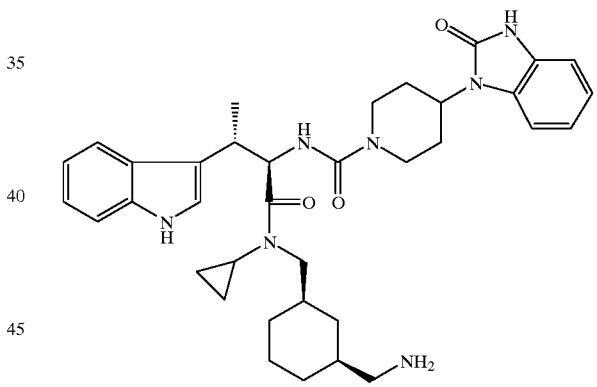

Step A:

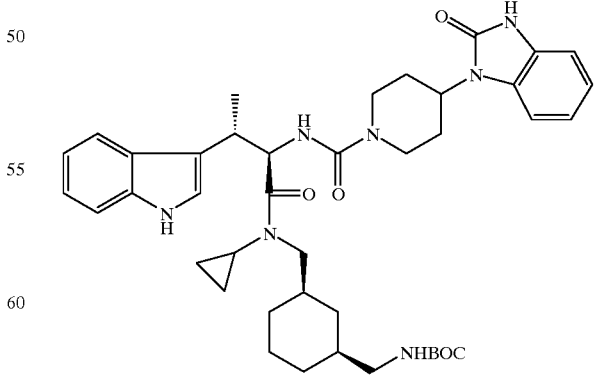

Secondary amine intermediate 5 (127 mg, 0.450 mmol), prepared as described above was combined with carboxylic acid intermediate 1 (228 mg, 0.495 mmol), PyBroP (241 mg, 0.518 mmol) and DIEA (235 mL, 1.35 mmol) in DCM (10 mL). The resulting mixture was stirred at rt overnight. The mixture was then diluted with DCM (80 mL) and washed with 1N HCl (2×75 mL), saturated NaHCO$_3$ solution (75 mL) and brine (75 mL). The organic layer was dried over MgSO$_4$, filtered and concentrated. The crude product was purified by MPLC (silica, 5% methanol/ethyl acetate), giving 178 mg of the product as a white solid.

Step B:

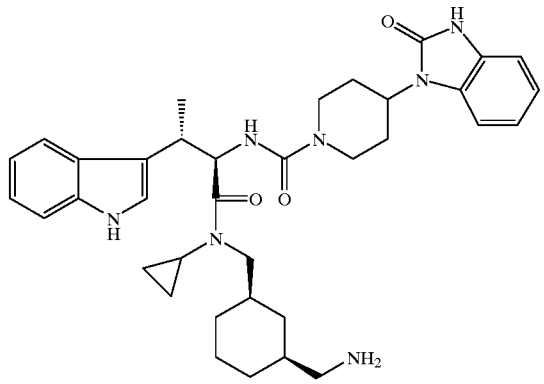

The product of the previous reaction (169.9 mg, 0.234 mmol) was dissolved in ethyl acetate (10 mL) and HCl (g) was bubbled through the resulting solution for 3–4 min. The solvent was evaporated to give 161.9 mg of product as a white solid.

ESI-MS calc. for C36H47N7O3: 625; Found: 626 (M+H).

EXAMPLE 5

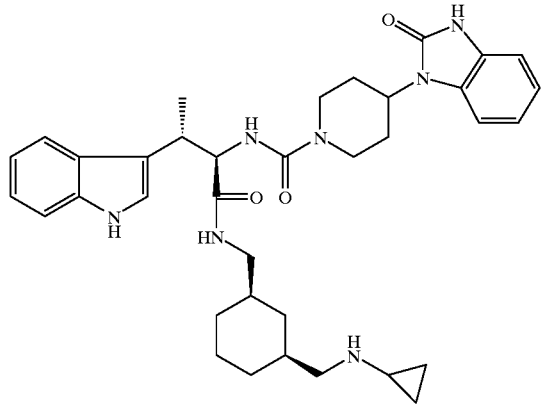

Step A:

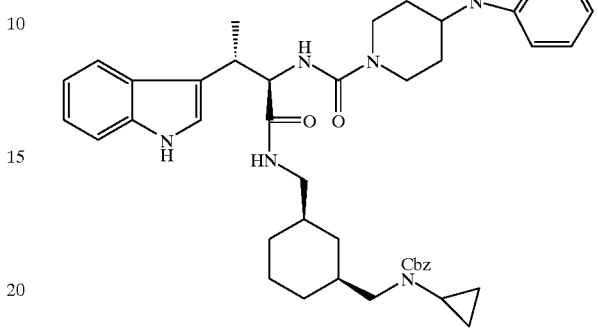

Intermediate amine 14 (117 mg, 0.332 mmol) was combined with intermediate carboxylic acid 1 (168 mg, 0.365 mmol), HOBt (81 mg, 0.60 mmol), DIEA (104 mL, 0.598 mmol) and EDC (115 mg, 0.598 mmol) in DCM (5 mL) and stirred overnight at rt. The reaction mixture was then diluted with DCM (50 mL) and washed with 1N HCl (40 mL), saturated NaHCO$_3$ solution (40 mL) and brine (40 mL). The organic layer was dried over MgSO$_4$, filtered and concentrated. The crude product was purified by MPLC (silica, 7.5% methanol/ethyl acetate) to afford 195.4 mg of product.

Step B:

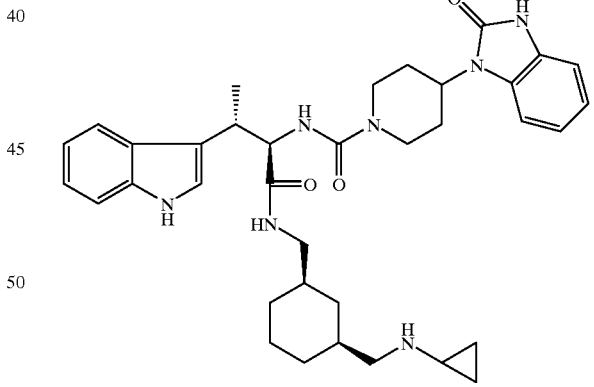

The product of the previous reaction (165 mg, 0.207 mmol) was combined with 20% Pd(OH)$_2$/C (30 mg) and ethanol (10 mL) and stirred under H$_2$ (g) for 3.5 h. The reaction mixture was filtered through celite and concentrated. The crude product was purified by flash chromatography (silica, 1% conc NH$_4$OH, 9% methanol/DCM) to give the pure product, which was converted to its HCl salt by addition of concentrated HCl solution (9 mL) to a methanolic (5 mL) solution of the free base, then removal of thge solvent under reduced pressure.

ESI-MS calc. for C36H47N7O3: 625; Found: 626 (M+H).

EXAMPLE 6

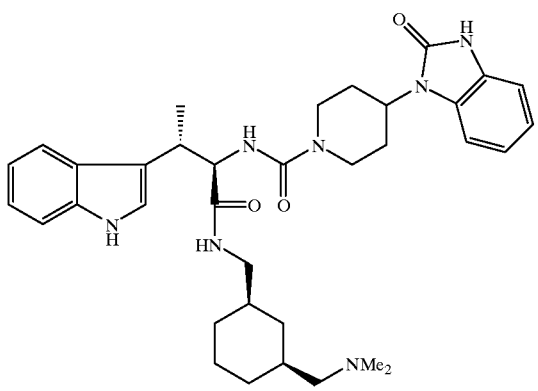

The primary amine product from example 2 above (145 mg, 0.233 mmol) was combined with 37% aqueous formaldehyde (95 mg, 1.2 mmol) and NaOAc (95.6 mg, 1.17 mmol) in methanol (5 mL). After 15 minutes NaCNBH$_3$ (24 mg, 0.37 mmol) was added and the reaction mixture was stirred at rt overnight. The reaction mixture was concentrated and the residue was purified by flash chromatography (silica, 1.5% conc NH$_4$OH, 13.5% methanol/DCM), giving, after adding concentrated HCl solution (19 mL) and concentrating again, 112.9 mg of the HCl salt.

ESI-MS calc. for C35H47N7O3: 613; Found 614 (M+H).

The examples listed in Table I below were prepared using the same protocols as for the examples (1–6) listed above.

TABLE I

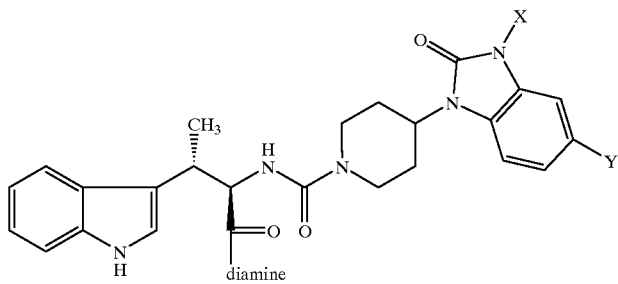

| Example | X | Y | diamine | MF ESI—MS (M + H) |
|---|---|---|---|---|
| 7 | H | H | HN–CH$_2$–(cyclohexane)–CH$_2$–NH$_2$ trans | C$_{33}$H$_{43}$N$_7$O$_3$ 586 |
| 8 | H | H | HN–CH$_2$–(cyclohexane)–CH$_2$–NH$_2$ cis | C$_{33}$H$_{43}$N$_7$O$_3$ 586 |
| 9 | H | H | HN–CH$_2$–(cyclohexane)–CH$_2$–NH$_2$ | C$_{33}$H$_{43}$N$_7$O$_3$ 586 |
| 10 | H | H | pentyl-N(CH$_2$–cyclohexane–CH$_2$–NH$_2$) | C$_{33}$H$_{43}$N$_7$O$_3$ 656 |
| 11 | H | H | t-BuO-C(O)-CH$_2$-N(CH$_2$-cyclohexane-CH$_2$-NH$_2$) | C$_{38}$H$_{53}$N$_7$O$_5$ 700 |

TABLE I-continued

| Example | X | Y | diamine | MF ESI—MS (M + H) |
|---|---|---|---|---|
| 12 | H | H | (isobutyl-N-CH2-cyclohexyl-CH2-NH2) | C37H51N7O3 642 |
| 13 | H | H | (propyl-N-CH2-cyclohexyl-CH2-NH2) | C36H49N7O3 628 |
| 14 | H | H | (F3C-CH2CH2-N-CH2-cyclohexyl-CH2-NH2) | C36H46N7O3F3 682 |
| 15 | H | H | (HN-CH2-cyclohexyl-CH2-NMeH) | C34H45N7O3 600 |
| 16 | H | H | (HN-CH2-cyclohexyl-CH2-NH-cyclopropyl) | C36H47N7O3 626 |
| 17 | H | H | (HN-CH2-cyclohexyl-CH2-NH-CH2CH2-CF3) | C36H46N7O3F3 682 |
| 18 | H | H | (HN-CH2-cyclohexyl-CH2-NH-CH2-C(=O)-OEt) | C37H49N7O5 672 |
| 19 | H | H | (HN-CH2-phenyl-CH2-NH2) | C33H37N7O3 580 |
| 20 | H | H | (isobutyl-N-CH2-phenyl-CH2-NH2) | C37H45N7O3 636 |

TABLE I-continued

| Example | X | Y | diamine | MF ESI—MS (M + H) |
|---|---|---|---|---|
| 21 | H | H | (N-benzyl, N-(3-aminomethylbenzyl)amine; Ph-CH2-N(H)-CH2-C6H4-CH2-NH2) | C40H43N7O3 670 |
| 22 | H | H | (N-(pyridin-3-ylmethyl)-N-(3-aminomethylbenzyl)amine) | C39H43N8O3 |
| 23 | H | H | (3-((dimethylamino)methyl)benzylamine) | C35H41N7O3 608 |
| 24 | H | H | (2-methyl-1,3-bis(aminomethyl)benzene) | C34H39N7O3 594 |
| 25 | H | H | (trans-4-(aminomethyl)cyclohexylamine) | C32H41N7O3 572 |
| 26 | H | H | (trans-4-((methylamino)methyl)cyclohexylamine) | C33H43N7O3 586 |
| 27 | H | H | (trans-4-((isobutylamino)methyl)cyclohexylamine) | C36H49N7O3 628 |
| 28 | H | H | (trans-4-(aminomethyl)-N,N-dimethylcyclohexylamine) | C34H44N7O3 599 |
| 29 | H | H | (trans-4-(aminomethyl)-N-ethylcyclohexylamine) | C34H44N7O3 599 |

TABLE I-continued
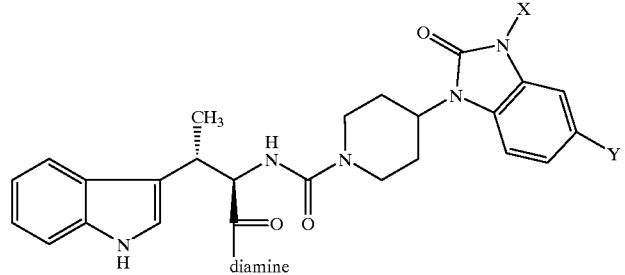
| Example | X | Y | diamine | MF ESI—MS (M + H) |
|---|---|---|---|---|
| 30 | H | H | | C34H43N7O5 630 |
| 31 | H | H | | C34H43N7O3 598 |
| 32 | H | H | | |
| 33 | H | Cl | | C33H42ClN7O3 621 |
| 34 | ethyl | H | | C35H47N7O3 614 |
| 35 | H | F | | C33H36FN7O3 598 |
| 36 | ethyl | H | | C35H41N7O3 608 |
| 37 | H | H | | |
| 38 | H | H | | |

TABLE I-continued

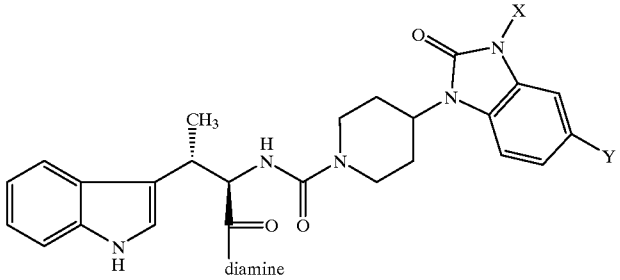

| Example | X | Y | diamine | MF ESI—MS (M + H) |
|---|---|---|---|---|
| 39 | H | H | 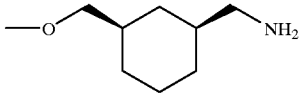 | |

The compounds shown in Table II, containing a variety of representative diamine units appended to the Trp, were prepared according to the above established procedures as exemplified in ExampleS 1 & 2 in conjunction with Intermediate 17 and for preparing the various required intermediates.

TABLE II

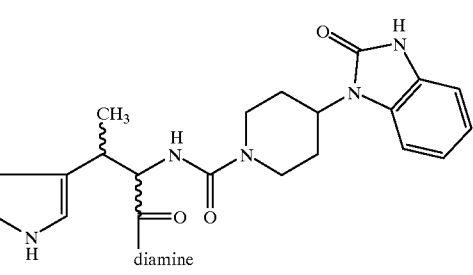

| Example | diamine | MF ESI—MS (M + H) |
|---|---|---|
| 40 | 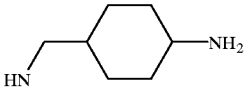 | C33H43N7O3 586 |
| 41 | 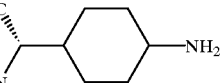 | C33H43N7O3 586 |
| 42 | 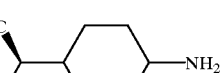 | C35H47N7O3 614 |

TABLE II-continued

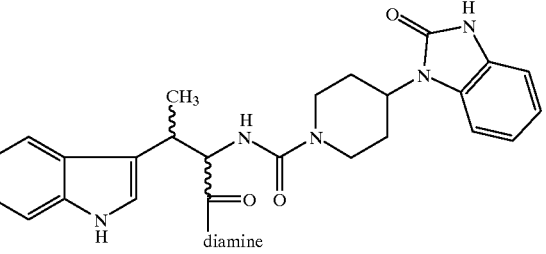

| Example | diamine | MF ESI—MS (M + H) |
|---|---|---|
| 43 | 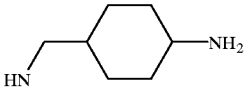 | C32H41N7O3 572 |
| 44 | 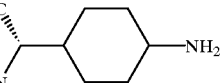 | C35H45N7O5 644 |
| 45 | 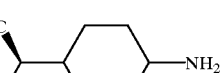 | C35H45N7O5 644 |

Biological Assays

The ability of compounds of the present invention to act as somatostatin agonist can be determined by the following in vitro assays, which is disclosed in Rens-Domiano, et al., Pharmacological Properties of Two Cloned Somatostatin Receptors, *Mol. Pharm.*, 42:28–34 (1992) and incorporated herein.

Receptor Expression Constructs

Mammalian expression vectors containing full length coding sequences for hSSTR1–5 were constructed as follows: Fragments of genomic DNA carrying the various human somatostatin receptors were inserted into the multiple cloning site of pcDNA3 (Invitrogen). The fragments used were a 1.5-kb PstI-XmnI fragment for hSSTR1, 1.7-kb BamHI-HindIII fragment for hSSTR2, 2.0-kb NcoI-HindIII fragment for hSSTR3, a 1.4-kb NheI-NdeI fragment for hSSTR4, and a 3.2-kb XhoI-EcoRI fragment for hSSTR5.
Transfection CHO-K1 cells were obtained from American Type Culture Collection (ATCC) and grown in alpha-MEM containing 10% fetal calf serum. Cells were stably transfected with DNA for all 5 hSSTRs using lipofectamine. Neomycin resistant clones were selected and maintained in medium containing G418 (400 µg ml).
Receptor binding assay Cells were harvested 72 hr after transfection to 50 mM Tris-HCl, pH 7.8, containing 1 mM EGTA, 5 mM $MgCl_2$, 10 µg/ml leupeptin, 10 µg/ml pepstatin, 200 µg/ml bacitracin, and 0.5 µg/ml aprotinin (buffer 1) and were centrifuged at 24,000×g for 7 min at 4°. The pellet was homogenized in buffer 1 using a Brinkman Polytron (setting 2.5, 30 sec). The homogenate was then centrifuged at 48,000 µg for 20 min at 4° C. The pellet was homogenized in buffer 1 and the membranes were used in the radioligand binding assay. Cell membranes (approximately 10 µg of protein) were incubated with $^{125}I$-$Tyr^{11}$-somatostatin (0.2 nM; specific activity, 2000 Ci/mmol; NEN) in the presence or absence of competing peptides, in a final volume of 200 µl, for 30 min at 25°. Nonspecific binding was defined as the radioactivity remaining bound in the presence of 100 nM somatastatin. The binding reaction was terminated by the addition of ice-cold 50 nM Tris-HCl buffer, pH 7.8, and rapid filtration with 12 ml of ice-cold Tris HCl buffer, and the bound radioactivity was counted in a gamma scintillation spectrophotometer (80% efficiency). Data from radioligand binding studies were used to generate inhibition curves. $IC_{50}$ values were obtained from curve-fitting performed with the mathematical modeling program FITCOMP, available through the National Institutes of Health-sponsored PROPHET system.
Inhibition of forskolin-stimulated cAMP accumulation Cells used for cAMP accumulation studies were subcultured in 12-well culture plates. COS-7 cells were transfected 72 hr before the experiments. Culture medium was removed from the wells and replaced with 500 µl of fresh medium containing 0.5 mM isobutylmethylxanthine. Cells were incubated for 20 min at 37°. Medium was then removed and replaced with fresh medium containing 0.5 mM isobutylmethylxanthine, with or without 10 µM forskolin and various concentrations of test compound. Cells were incubated for 30 min at 37°. Medium was then removed, and cells were sonicated in the wells in 500 µL of 1N HCl and frozen for subsequent determination of cAMP content by radioimmunassay. Samples were thawed and diluted in cAMP radioimmunassay buffer before analysis of cAMP content using the commercially available assay kit from NEW/DuPont (Wilmington, Del.).
Inhibition of growth hormone release Functional activity of the various compounds was evaluated by quantitating release of growth hormone secretion from primary cultures of rat anterior pituitary cells. Cells were isolated from rat pituitaries by enzymatic digestion with 0.2% collagenase and 0.2% hyaluronidase in Hank's balanced salt solution. The cells were suspended in culture medium and adjusted to a concentration of $1.5 \times 10^5$ cells per milliliter, and 1.0 ml of this suspension was placed in each well of a 24-well tray. Cells were maintained in a humidified 5% $CO^2$-95% air atmosphere at 37° C. for 3 to 4 days. The culture medium consisted of Dulbecco's modified Eagle's medium containing 0.37% $NaHCO_3$, 10% horse serum, 2.5% fetal bovine serum, 1% nonessential amino acids, 1% glutamine, 1% nystatin, and 0.1% gentamycin. Before testing compounds for their capacity to inhibit GH release, cells were washed twice 1.5 hours before and once more immediately before the start of the experiment with the above culture medium containing 25 mM Hepes (pH 7.4). The compounds of the insant invention were tested in quadruplicate by adding them in 1 ml of fresh medium to each well and incubating them at 37° C. for 15 min. After incubation, the medium was removed and centrifuged at 2000 g for 15 min to remove any cellular material. The supernatant fluid was removed and assayed for GH by radioimmunoassay.

The compounds of this invention were found to inhibit the binding of somatostatin to its receptor at an $IC_{50}$ of about 30 µM to about 3 µM.

What is claimed is:

1. A compound represented by formula I:

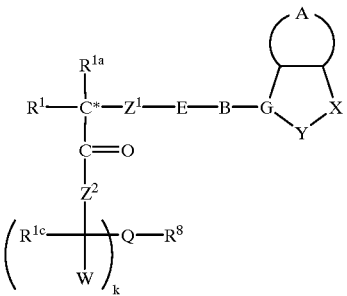

or a pharmaceutically acceptable salt or hydrate thereof, wherein $R^1$ is selected from the group consisting of: $C_{1-10}$alkyl, aryl, aryl($C_{1-6}$alkyl)—, $C_{3-7}$cycloalkyl($C_{1-6}$alkyl)—, $C_{1-5}$alkyl-K-($C_1$–$C_5$ alkyl)—, aryl($C_{0-5}$ alkyl)-K-($C_{1-5}$alkyl)—, and $C_{3-7}$cycloalkyl($C_{0-5}$alkyl)-K-($C_{1-5}$alkyl)—, wherein K is —O—, —S(O)$_m$—, —N($R^2$)C(O)—, —C(O)N($R^2$)—, —$CR^2$=$CR^2$— or —C≡C—, the allyl portions of which are optionally substituted with by 1 to 5 halogen groups, S(O)$_m R^{2a}$, 1 to 3 of $OR^{2a}$ groups or C(O)$OR^{2a}$, and wherein aryl is selected from the group consisting of: phenyl, naphthyl, biphenyl, quinolinyl, isoquinolinyl, indolyl, azaindolyl, pyridyl, benzothienyl, benzofuranyl, thiazolyl and benzimidazolyl, said aryl groups being unsubstituted or substituted with 1 to 3 $C_{1-6}$ alkyl or halo groups, 1 to 2 —$OR^2$ groups, methylenedioxy, —S(O)$_m R^2$, 1 to 2 —$CF_3$ groups, —$OCF_3$, —$NO_2$, —N($R^2$)C(O)($R^2$), —C(O)$OR^2$, —C(O)N($R^2$)$_2$, 1H-tetrazol-5-yl, —$SO_2$N($R^2$)($R^2$), —N($R^2$)$SO_2$ phenyl, or —N($R^2$)$SO_2 R^2$;

$R^2$ is selected from the group consisting of: H, $C_{1-8}$alkyl, —(CH$_2$)$_t$-aryl and $C_{3-7}$cycloalkyl, and where two $R^2$ groups are present, they optionally are joined to form a $C_3$–$C_8$ ring, optionally interrupted by O, S or $NR^{3a}$, in which $R^{3a}$ is H or $C_{1-6}$alkyl optionally substituted by OH;

t is an integer from 0 to 3;

and when $R^2$ is other than H, $R^2$ is optionally substituted with 1 to 5 halogen groups, S(O)$_m R^{2a}$, 1 to 3 of $OR^{2a}$ groups or C(O)$OR^{2a}$, $R^{2a}$ is H or $C_{1-3}$ alkyl optionally substituted by OH;

m is 0, 1 or 2;

$R^{1a}$ is H or $C_{1-3}$alkyl;

$Z^1$ is selected from the group consisting of —O—, —CH$_2$— and $NR^{2a}$;

E is selected from the group consisting of —SO$_2$—, —C(O)—, —CO(C(R$^2$)$_2$)$_n$—, —C(=N—CN)—, —C(=N—NO$_2$)— and —C(=N—SO$_2$N(R$^2$)$_2$)—;

n is an integer from 0 to 3;

B is

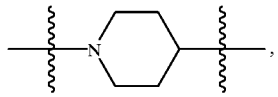

where attachment points are indicated by lines,

said group being optionally substituted by $C_{1-6}$alkyl;

represents an aromatic or non-aromatic 5–6 membered ring structure wherein:

G is N,

Y is —C(O)—, —C(OR$^{11}$)=, —C(SR$^{11}$)=, —C(NR$^{11}$)=, or —C(R$^{11}$)$_2$—;

and

X is —N(R$^{11}$)— or =N—;

$R^{11}$ is H, $C_{1-8}$alkyl, CF$_3$, CH$_2$CF$_3$, —(CH$_2$)$_p$OR$^2$, —(CH$_2$)$_p$N(R$^2$)$_2$, —(CH$_2$)$_p$N(R$^2$)C(O)N(R$^2$)$_2$, —(CH$_2$)$_p$N(R$^2$)C(O)R$^2$, —(CH$_2$)$_2$-heteroaryl, —(CH$_2$)$_p$N(R$^2$)SO$_2$C$_{1-4}$alkyl, —(CH$_2$)$_p$C(O)N(R$^2$)$_2$ or —(CH$_2$)$_p$C(O)OR$^2$, wherein heteroaryl is selected from tetrazolyl, oxadiazolyl, imidazolyl and triazolyl, said heteroaryl being optionally substituted with $R^2$, OR$^2$, CF$_3$ or N(R$^2$)$_2$ and where p is 0–3;

is a 6 membered fused aryl group, said aryl group being optionally substituted with 1–3 $C_{1-6}$alkyl or halo groups, —OR$^2$, N(R$^2$)$_2$, methylenedioxy, —S(O)$_m$R$^2$, —CF$_3$, —OCF$_3$, —NO$_2$, —N(R$^2$)C(O)(R$^2$), —C(O)OR$^2$, —C(O)N(R$^2$)$_2$, 1H-tetrazol-5-yl, —SO$_2$N(R$^2$)$_2$, —N(R$^2$)SO$^2$ phenyl, —N(R$^2$)C(O)N(R$^2$)$_2$ or —N(R$^2$)SO$_2$R$^2$;

$Z^2$ is selected from the group consisting of —O—, —CH$_2$—, —CHR$^{2b}$— and —NR$^{2b}$—, wherein $R^{2b}$ is selected from the group consisting of: H, $C_{1-8}$alkyl, —(CH$_2$)$_t$-aryl, —(CH$_2$)$_n$CO$_2$R$^2$, —(CH$_2$)$_n$CON(R$^2$)$_2$ and —(CH$_2$)$_n$OR$^2$, and when $Z^2$ is NR$^{2b}$ it can optionally be linked to $R^{1c}$, Q or W to form a C5–8 ring, which is optionally interrupted by O, S(O)$_m$ or NR$^{2a}$;

$R^{1c}$ is selected from the group consisting of: H, —(CH$_2$)$_q$SR$^2$, —(CH$_2$)$_q$OR$^2$ and $C_{1-8}$alkyl;

W is selected from the group consisting of: H, $C_{1-8}$alkyl, —(CH$_2$)$_t$-aryl, —(CH$_2$)$_q$C(O)OR$^2$, —(CH$_2$)$_q$OR$^2$, —(CH$_2$)$_q$OC(O)R$^2$, —(CH$_2$)$_q$C(O)R$^2$, —(CH$_2$)$_q$C(O)(CH$_2$)$_t$aryl, —(CH$_2$)$_q$C(O)N(R$^2$)$_2$, —(CH$_2$)$_q$N(R$^2$)C(O)R$^2$, —(CH$_2$)$_q$N(R$^2$)SO$_2$R$^2$, —(CH$_2$)$_q$N(R$^2$)C(O)N(R$^2$)$_2$, —(CH$_2$)$_q$OC(O)N(R$^2$)$_2$, —(CH$_2$)$_q$N(R$^2$)C(O)OR$^2$, —(CH$_2$)$_q$N(R$^2$)SO$_2$N(R$^2$)$_2$, —(CH$_2$)$_q$S(O)$_m$R$^2$ and —(CH$_2$)$_t$-heteroaryl, the heteroaryl portion of which is selected from: tetrazolyl, oxadiazolyl, thiadiazolyl, triazolyl and pyrazinyl, optionally substituted with $R^2$, N(R$^2$)$_2$ or OR$^2$, and when $R^2$ is other than H, said $R^2$, (CH$_2$)$_q$ and the (CH$_2$)$_t$ portions of W are optionally substituted with 1 to 2 $C_{1-4}$alkyl, OR$^{2a}$, C(O)OR$^{2a}$ or 1–3 halo groups, and the aryl and heteroaryl portions of W being optionally substituted with 1 to 3 halo groups, —OR$^2$, —CON(R$^2$)$_2$, —C(O)OR$^2$, $C_{1-4}$alkyl, —S(O)$_m$R$^2$, N(R$^2$)$_2$, CF$_3$ or 1H-tetrazol-5-yl;

k is 0 or 1, such that when k is 0, Q is attached directly to $z^2$;

Q represents a member selected from the group consisting of:

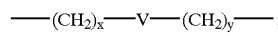

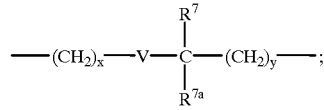

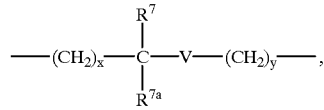

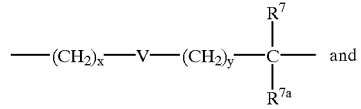

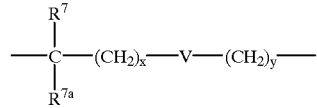

where x and y are independently 0, 1, 2, 3, 4, 5, 6;

V is an aromatic 6–12 membered mono- or bicyclic ring system or a non-aromatic 3–12 membered mono- or bicyclic ring system, optionally substituted with 1 to 2 $R^2$ groups, 1 to 3 halo groups, —OR$^2$, —CON(R$^2$)$_2$, —C(O)OR$^2$, —C$_{1-4}$alkyl, —S(O)$_m$R$^2$, N(R$^2$)$_2$, CF$_3$ or 1H-tetrazol-5-yl;

$R^7$ and $R^{7a}$ are independently CF$_3$ or $R^2$;

$R^8$ is selected from the group consisting of

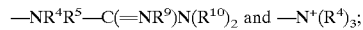

$R^4$ and $R^5$ are independently selected from the group consisting of: $R^2$, —C(=NR$^2$)N(R$^2$)$_2$, —C(=NCN)N(R$^2$)$_2$, —C(=NC(O)R$^2$)N(R$^2$)$_2$, C(=NSO$_2$R$^2$)N(R$^2$)$_2$, —C(=NNO$_2$)NR$^2$, heteroaryl, —C(O)N(R$^2$)$_2$, —C(=S)N(R$^2$)$_2$, —C(O)R$^2$, 2,2,2-trifluoroethyl, 3,3,3-trifluoropropyl and —(CH$_2$)$_t$-cyclopropyl, or $R^4$ and $R^5$ are taken together and represent

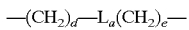

wherein $L_a$ is —C(R$^2$)$_2$—, —O—, —S(O)$_m$— or —N(R$^2$)—, and d and e are independently 0 to 3 such that d plus e equals 2–6, and said heteroaryl and R$^2$ other than H being optionally substituted with 1–3 C$_{1-6}$alkyl groups, 1–7 halo groups, N(R$^2$)$_2$, OR$^2$, N(R$^2$)C(O)R$^2$, C(O)N(R$^2$), OC(O)R$^2$, S(O)$_m$R$^2$, CF$_3$, OCF$_3$, NO$_2$, N(R$^2$)C(O)(R$^2$), N(R$^2$)C(O)N(R$^2$)$_2$, C(O)OR$^2$, C(O)N(R$^2$)$_2$, SO$_2$N(R$^2$)$_2$, N(R$^2$)SO$_2$R$^2$ or methylenedioxy;

and R$^9$ and R$^{10}$ are independently H or C$_{1-8}$alkyl or may be taken together and represent a C$_{5-8}$ ring, optionally substituted by 1–5 halo groups, OR$^2$ or S(O)$_m$R$^2$.

2. A compound in accordance with claim 1 wherein:

Q is

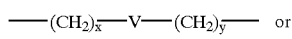

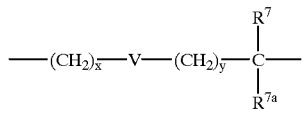

and x and y are independently 0, 1, 2, 3 or 4.

3. A compound in accordance with claim 2 wherein Q is

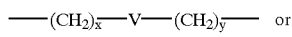

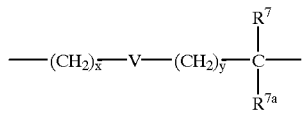

and x and y are independently 0, 1, 2 or 3.

4. A compound in accordance with claim 2 wherein V represents an aromatic or non-aromatic 3–12 membered ring system selected from the group consisting of: cyclopropyl, cyclobutyl, cyclopentyl, cyclohexyl, cycloheptyl, cyclooctyl, phenyl and naphthyl optionally substituted with 1 to 2 R$^2$ groups, 1 to 3 halo groups, —OR$^2$, —CON(R$^2$)$_2$, —C(O)OR$^2$, C$_1$–C$_4$ alkyl, —S(O)$_m$R$^2$, N(R$^2$)$_2$, CF$_3$ or 1H-tetrazol-5-yl.

5. A compound in accordance with claim 1 wherein:

V represents a member selected from the group consisting of: phenyl, cyclohexyl and cyclopentyl, which is optionally substituted with 1 to 3 halo groups, —OR$^2$, —CON(R$^2$)$_2$, —C(O)OR$^2$, C$_1$–C$_4$ alkyl, —S(O)$_m$R$^2$, N(R$^2$)$_2$, CF$_3$ or 1H-tetrazol-5-yl.

6. A compound in accordance with claim 1 wherein R$^8$ represents —NR$^4$R$^5$.

7. A compound in accordance with claim 5 wherein R$^8$ represents —NR$^4$R$^5$, and R$^4$ and R$^5$ are independently selected from the group consisting of R$^2$, 2,2,2-trifluoroethyl, 3,3,3-trifluoropropyl and (CH$_2$)$_t$-cyclopropyl.

8. A compound in accordance with claim 1 wherein:

R$^1$ is selected from the group consisting of:

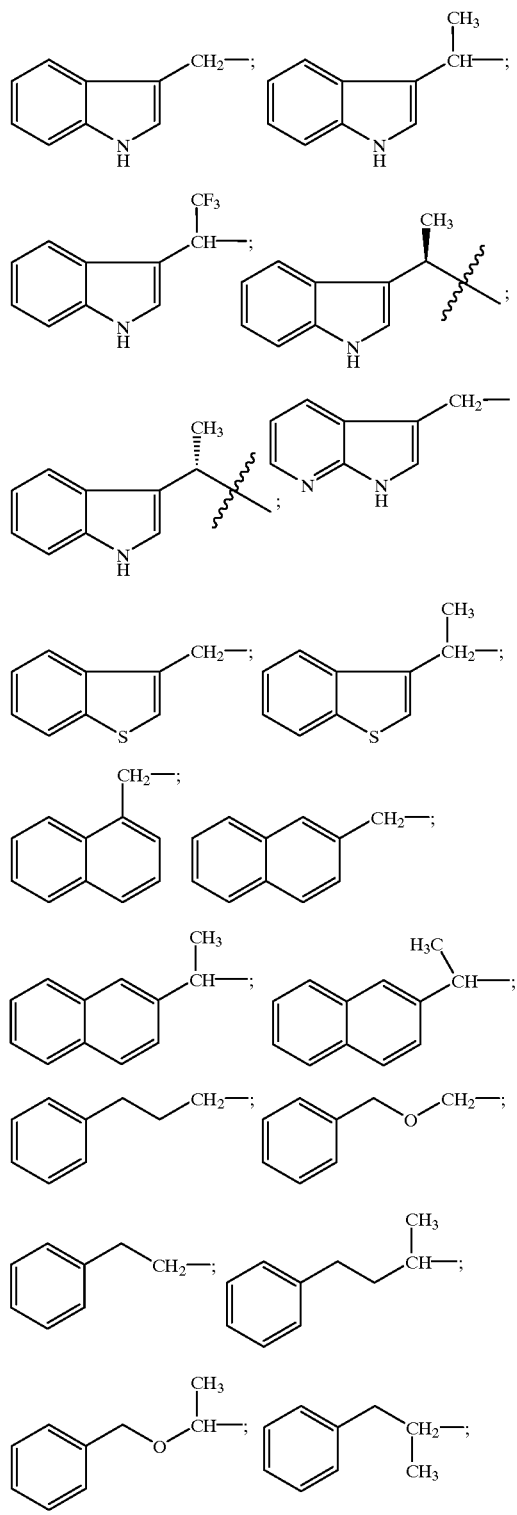

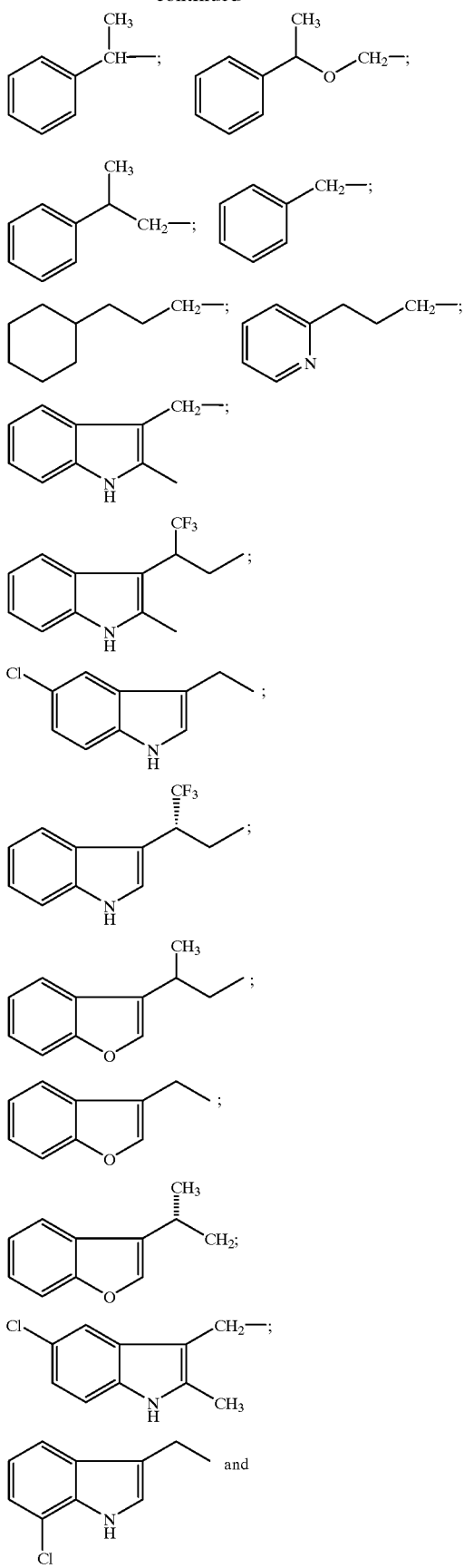

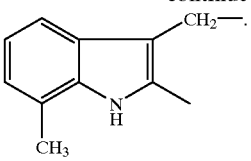

wherein the aryl portion is unsubstituted or substituted with: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, -$SO_2N(R^2)(R^2)$, —$N(R^2)SO_2$ phenyl, or —$N(R^2)SO_2R^2$.

9. A compound in accordance with claim 1 wherein:

$R^2$ is selected from: hydrogen, methyl, ethyl, propyl, isopropyl, butyl, isobutyl and t-butyl.

10. A compound in accordance with claim 1 wherein:

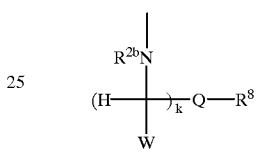

is selected from the group consisting of:

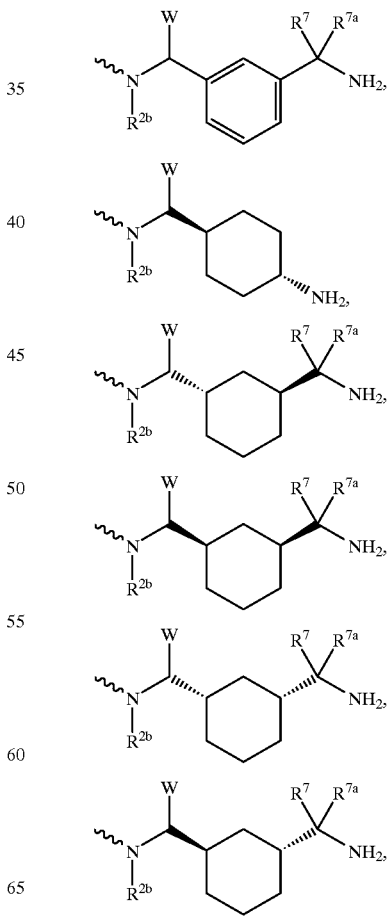

-continued

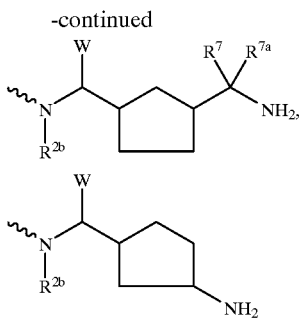

in which the phenyl or cycloalkyl group is optionally substituted with 1 to 2 $R^2$ groups, 1 to 3 halo groups, —$OR^2$, —$CON(R^2)_2$, —$C(O)OR^2$, $C_1$–$C_4$ alkyl, —$S(O)_mR^2$, $N(R^2)_2$, or $CF_3$.

11. A compound in accordance with claim 1 wherein:

W is selected from the group consisting of: hydrogen, $C_1$–$C_4$ alkyl and $(CH_2)_qC(O)OR^2$ and q is 0, 1 or 2.

12. A compound in accordance with claim 1 wherein:

E is selected from the group consisting of —CO—, —C(=N—CN)—, and —$SO_2$—.

13. A compound in accordance with claim 1 wherein:

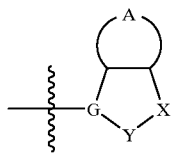

is selected from the group consisting of:

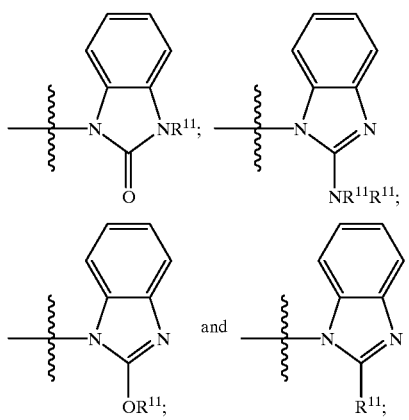

and where the aromatic rings are optionally substituted with 1–3 groups of $C_1$–$C_6$ alkyl, halogen, —$OR^2$, $N(R^2)_2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, —1H-tetrazol-5-yl, —$SO_2N(R^2)_2$, -$N(R^2)SO_2$ phenyl, $N(R^2)C(O)N(R^2)$ or —$N(R^2)SO_2R^2$.

14. A compound of structural formula I':

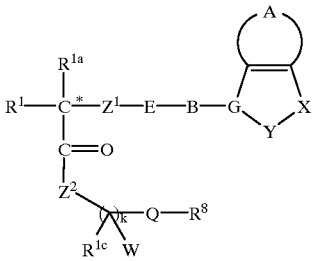

Formula I' or a pharmaceutically acceptable salt or hydrate thereof, wherein $R^1$ is selected from the group consisting of: $C_1$–$C_{10}$ alkyl, aryl, aryl ($C_1$–$C_6$ alkyl), ($C_3$–$C_7$ cycloalkyl)($C_1$–$C_6$ alkyl)—, ($C_1$–$C_5$ alkyl)-K-($C_1$–$C_5$ alkyl)—, aryl ($C_0$–$C_5$ alkyl)-K-($C_1$–$C_5$ alkyl)—, and ($C_3$–$C_7$ cycloalkyl)($C_0$–$C_5$ alkyl)-K-($C_1$–$C_5$ alkyl)—, where K is —O—, —$S(O)_m$—, —$N(R^2)C(O)$—, —$C(O)N(R^2)$—, —$CR^2$=$CR^2$—, or —C≡C—, where $R^2$ and alkyl may be further substituted by 1 to 5 halogen, $S(O)_mR^{2a}$, 1 to 3 of $OR^{2a}$ or $C(O)OR^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetraol-5-yl, —$SO_2N(R^2)(R^2)$, —$N(R^2)SO_2$ phenyl, or —$N(R^2)SO_2R^2$;

$R^2$ is selected from: hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl; Aryl is defined in the body of the case;

$R^{1a}$ is selected from the group consisting of hydrogen, and $C_1$–$C_3$ alkyl;

$R^{2a}$ is selected from the group consisting of hydrogen and $C_1$–$C_3$ alkyl, said alkyl optionally substituted by hydroxyl;

$R^{2b}$ is selected from hydrogen, $C_1$–$C_3$ alkyl, $(CH_2)_t$ aryl, —$(CH_2)_nCO_2R^2$, —$(CH_2)_nCON(R^2)_2$, —$(CH_2)_nOH$, $(CH_2)_nCF_3$, $(CH_2)_t$ heteroaryl or —$(CH_2)_nOR^2$;

$R^{1c}$ is selected from the group consisting of hydrogen, —$(CH_2)_qSR^2$, —$(CH_2)_qOR^2$ and $C_1$–$C_8$ alkyl;

$Z^1$ is selected from the group consisting of —O—, —$CH_2$— and —$NR_{2a}$;

$Z^2$ is selected from the group consisting of —O—, —$CH_2$—,—$CHR^{2b}$— and —$NR^{2b}$, when $Z^2$ is $NR^{2b}$ it can optionally be linked to $R^{1c}$, Q and/or W to form a C5–8 cyclic ring, which can optionally be interrupted by oxygen, $S(O)_m$ or $NR^{2a}$;

W is selected from the group consisting of: hydrogen, $C_1$–$C_8$ alkyl, $(CH2)_t$ aryl, —$(CH_2)_qC(O)OR^2$, —$(CH_2)_qOR^2$, —$(CH_2)_qOC(O)R^2$, —$(CH_2)_qC(O)R^2$, —$(CH_2)_qC(O)(CH_2)_t$aryl, —$(CH_2)_qC(O)N(R^2)_2$, —$(CH_2)_qN(R^2)C(O)R^2$, —$(CH_2)_qN(R^2)SO_2R^2$, —$(CH_2)_qN(R^2)C(O)N(R^2)_2$, —$(CH_2)_qOC(O)N(R^2)_2$, —$(CH_2)_qN(R^2)C$ (O)OR², —(CH₂)$_q$N(R²)SO₂N(R²)₂, —(CH₂)$_q$S(O)$_m$R², and (CH₂)$_t$ heteroaryl where the heteroaryl is preferably tetrazole, oxadiazole, thiadiazole, triazole or pyrazine, which is optionally substituted with R², N(R²)₂ and OR², where R², (CH₂)$_q$ and (CH2)$_t$ are optionally substituted with 1 to 2 C₁–C₄ alkyl, OR², C(O)OR², 1–3 halo and said aryl is optionally substituted with 1 to 3 halogen, —OR², —CON(R²)₂, —C(O)OR², C₁–C₄ alkyl, —S(O)$_m$R², N(R²)₂, CF₃ or 1H-tetrazol-5-yl;

Q is selected from the group consisting of:

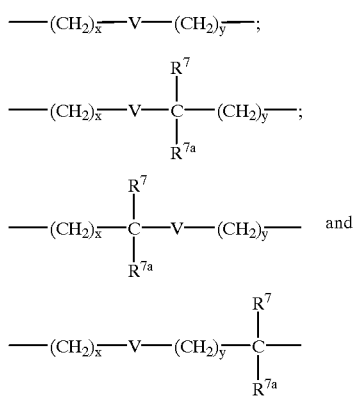

where x and y are independently 0, 1, 2, 3, 4, 5, 6;

V is a C₃₋₈ nonaromatic cyclic or bicyclic ring or an aromatic selected from benzene and napthalene; wherein said aromatic or non aromatic ring is optionally substituted with 1 to 2 R², 1 to 3 halogen, —OR², —CON(R²)₂, —C(O)OR², C₁—C₄ alkyl, —S(O)$_m$R², N(R²)₂, CF₃ or 1H-tetrazol-5-yl; and in the case where diastereo- or regio- isomers are present, all are included;

R⁷ and R⁷$^a$ are independently trifluoromethyl or R²;

R⁸ is selected from the group consisting of

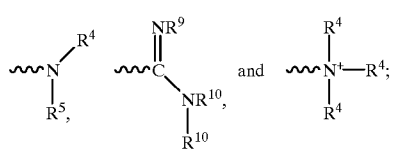

R⁴ and R⁵ are independently selected from the group consisting of R², —C(≡NR²)N(R²)₂, —C(=NCN)N(R²)₂, —C(=NC(O)R²)N(R²)₂, C(=NSO₂R²)N(R²)₂, —C(=NNO₂)NR², heteroaryl, (CH₂)$_n$CO₂R²—C(=O)N(R²)₂, —C(=S)N(R²)₂, —C(=O)R², 2,2,2-trifluoroethyl, 3,3,3-trifluoropropyl, (CH₂)$_t$ cyclopropyl, or R⁴ and R⁵ may be taken together to form —(CH₂)$_d$-L$_a$(CH₂)$_e$— where L$_a$ is —C(R²)₂—, —O—, —S(O)$_m$— or —N(R²)—, d and e are independently 1 to 3, said heteroaryl and R² optionally substituted with 1–3 groups of C₁₋₆ alkyl, 1–7 halo, N(R²)₂, OR², N(R²)C(O)R², C(O)N(R²), OC(O)R², S(O)$_m$R², CF₃, OCF₃, NO₂, N(R²)C(O)(R²), N(R²)C(O)N(R²)₂, C(O)OR², C(O)N(R²)₂, SO₂N(R²)₂, N(R²)SO₂R², or methylenedioxy; and the heteroaryl is pyridyl, imidazolyl, pyrimidinyl, thiazolyl or pyrazinyl;

E is selected from the group consisting of —SO₂—, —CO(C(R²)₂)$_n$—, —C(=N—CN)—, —C(=N—NO₂)— and —C(=N—SO₂N(R²)₂)—;

R⁹ & R¹⁰ are independently H, C₁₋₈ alkyl or may be taken together to form a C5–8 cyclic ring, which can optionally be substituted by 1–5 halogen, OR² or S(O)$_m$R²;

B is

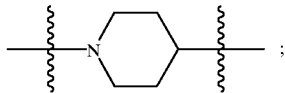

where attachment points are indicated by lines (∫) external to the ring which is optionally substituted by C₁–C₆ alkyl;

G is N; p1 Y is —C(O)—, —C(OR¹¹)=, —C(SR¹¹)=, —C(NR¹¹)=, or —C(R¹¹)₂—;

X is —N(R¹¹)— or =N—;

R¹¹ is H, C₁–C₈ alkyl, CF₃, CH₂CF₃, —(CH₂)$_p$OR², —(CH₂)$_p$N(R²)₂, (CH₂)$_p$N(R²)C(O)N(R²)₂, —(CH₂)$_p$N(R²)C(O)R², (CH₂)₂ heteroaryl, (CH₂)$_p$N(R²)SO₂C₁–C₄ alkyl, —(CH₂)$_p$C(O)N(R²)₂, or —(CH₂)$_p$C(O)OR² where heteroaryl is tetrazole, oxadiazole, imidazole or triazole which are optionally substituted with R², OR², CF₃ or N(R²)₂ and where p is 0–3;

A is a fused aryl group, said aryl group containing 6 atoms and being optionally substituted with 1–3 groups of C₁–C₆ alkyl, halogen, —OR², N(R²)₂, methylenedioxy, —S(O)$_m$R², —CF₃, —OCF₃, nitro, —N(R²)C(O)(R²), —C(O)OR², —C(O)N(R²)₂, —1H-tetrazol-5-yl, —SO₂N(R²)₂, —N(R²)SO₂ phenyl, N(R²)C(O)N(R²) or —N(R²)SO₂R², and in the case where regioisomers are present, all are included;

k is an integer from 0 to 1, such that when k is 0, Q is attached directly to Z²;

m is an integer from 0 to 2;

n is an integer from 0 to 3;

q is an integer from 0 to 3; and t is an integer from 0 to 3.

15. A compound according to claim 1 having a structural formula Ib:

Formula Ib

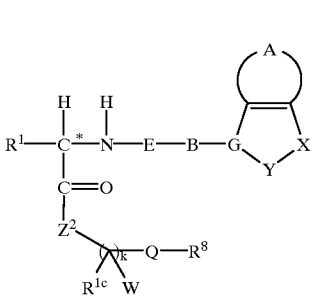

or a pharmaceutically acceptable salt or hydrate thereof, wherein:

R¹ is selected from the group consisting of: C₁–C₁₀ alkyl, aryl, aryl (C₁–C₆ alkyl), (C₃–C₇ cycloalkyl)(C₁–C₆ alkyl)—, (C₁–C₅ alkyl)-K-(C₁–C₅ alkyl)—, aryl (C₀–C₅ alkyl)-K-(C₁–C₅ alkyl)—, and (C₃–C₇ cycloalkyl)(C₀–C₅ alkyl)-K-(C₁–C₅ alkyl)—, where K is —O—, —S(O)$_m$—, —N(R²)C(O)—, —C(O)N(R²)—, —CR²=CR²—, or —C∫C—, where R² and alkyl may be further substituted by 1 to 5 halogen, S(O)$_m$R²$^a$, 1 to 3 of OR²$^a$ or C(O)OR²$^a$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, —$SO_2N(R^2)(R^2)$, —$N(R^2)SO_2$ phenyl, or —$N(R^2)SO_2R^2$;

$R^2$ is selected from: hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl;

$R^{2a}$ is selected from the group consisting of hydrogen and $C_1$–$C_3$ alkyl, said alkyl optionally substituted by hydroxyl;

$Z^2$ is selected from the group consisting of —O—, —CH2—, —CHR$^{2b}$— and —NR$^{2b}$, when $Z^2$ is NR$^{2b}$ it can optionally be linked to $R^{1c}$, Q and/or W to form a $C_{5-8}$ cyclic ring, which can optionally be interrupted by oxygen, $S(O)_m$ or $NR^{2a}$;

$R^{2b}$ is selected from hydrogen, $C_1$–$C_8$ alkyl, $(CH_2)_t$ aryl, —$(CH_2)_nCO_2R^2$, —$(CH_2)_nCON(R^2)_2$, —$(CH_2)_nOH$, $(CH_2)_nCF_3$, $(CH_2)_t$ heteroaryl or —$(CH_2)_nOR^2$;

$R^{1c}$ is selected from the group consisting of hydrogen, and $C_1$–$C_8$ alkyl;

W is selected from the group consisting of: hydrogen, $C_1$–$C_8$ alkyl, (CH2)$_t$ aryl, —$(CH_2)_qC(O)OR^2$, —$(CH_2)_qOR^2$, —$(CH_2)_qOC(O)R^2$, —$(CH_2)_qC(O)R^2$, —$(CH_2)_qC(O)(CH_2)_t$aryl, —$(CH_2)_qC(O)N(R^2)_2$, —$(CH_2)_qN(R^2)C(O)R^2$, —$(CH_2)_qN(R^2)SO_2R^2$, —$(CH_2)_qN(R^2)C(O)N(R^2)_2$, —$(CH_2)_qOC(O)N(R^2)_2$, —$(CH_2)_qN(R^2)C(O)OR^2$, —$(CH_2)_qN(R^2)SO_2N(R^2)_2$, —$(CH_2)_qS(O)_mR^2$, and $(CH_2)_t$ heteroaryl where the heteroaryl is preferably tetrazole, oxadiazole, thiadiazole, triazole or pyrazine, which is optionally substituted with $R^2$, $N(R^2)_2$ and $OR^2$, where $R^2$, $(CH_2)_q$ and $(CH_2)_t$ are optionally substituted with 1 to 2 $C_1$–$C_4$ alkyl, $OR^2$, $C(O)OR^2$, 1–3 halo and said aryl is optionally substituted with 1 to 3 halogen, —$OR^2$, —$CON(R^2)_2$, —$C(O)OR^2$, $C_1$–$C_4$ alkyl, —$S(O)_mR^2$, $N(R^2)_2$, $CF_3$ or 1H-tetrazol-5-yl;

Q is

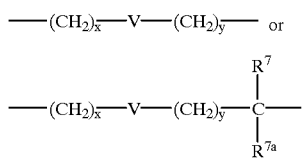

where x and y are independently 0, 1, 2, 3, 4;

V is a $C_{3-8}$ nonaromatic cyclic or bicyclic ring consisting of, cyclopropane, cyclobutane, cyclopentane, cyclohexane, cycloheptane, cyclooctane; or an aromatic such as benzene, napthalene; said aromatic or non aromatic ring can be optionally substituted with 1 to 2 $R^2$, 1 to 3 halogen, —$OR^2$, —$CON(R^2)_2$, —$C(O)OR^2$, $C_1$–$C_4$ alkyl, —$S(O)_mR^2$, $N(R^2)_2$, $CF_3$ or 1H-tetrazol-5-yl, or where Q and $R^8$ can be lined to form a $C_{3-8}$ cyclic ring; and in the case where diastereo- or regio- isomers are present, all are included;

$R^7$ and $R^{7a}$ are independently trifluoromethyl or $R^2$;

$R^8$ is selected from the group consisting of

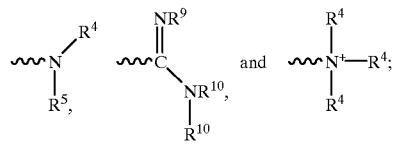

$R^4$ and $R^5$ are independently selected from the group consisting of $R^2$, —$C(=NR^2)N(R^2)_2$, —$C(=NCN)N(R^2)_2$, —$C(=NC(O)R^2)N(R^2)_2$, $C(=NSO_2R^2)N(R^2)_2$, —$C(=NNO2)NR^2$, heteroaryl, $(CH_2)_nCO_2R^2$—$C(=O)N(R^2)_2$, —$C(=S)N(R^2)_2$, —$C(=O)R^2$, 2,2,2-trifluoroethyl, 3,3,3-trifluoropropyl, $(CH_2)_t$ cyclopropyl, or $R^4$ and $R^5$ may be taken together to form —$(CH_2)_d$-$L_a(CH_2)_e$— where $L_a$ is —$C(R^2)_2$—, —O—, —$S(O)_m$— or —$N(R^2)$—, d and e are independently 1 to 3, said heteroaryl and $R^2$ optionally substituted with 1–3 groups of $C_{1-6}$ alkyl, 1–7 halo, $N(R^2)_2$, $OR^2$, $N(R^2)C(O)R^2$, $C(O)N(R^2)$, $OC(O)R^2$, $S(O)_mR^2$, $CF_3$, $OCF_3$, $NO_2$, $N(R^2)C(O)(R^2)$, $N(R^2)C(O)N(R^2)_2$, $C(O)OR^2$, $C(O)N(R^2)_2$, $SO_2N(R^2)_2$, $N(R^2)SO_2R^2$, or methylenedioxy; and the heteroaryl is pyridyl, imidazolyl, pyrimidinyl, thiazolyl or pyrazinyl;

E is selected from the group consisting of —$SO_2$—, —$CO(C(R^2)_2)_n$—, —$C(=N—CN)$—, —$C(=N—NO_2)$— and —$C(=N—SO_2N(R^2)_2)$—;

$R^9$ & $R^{10}$ are independently H, $C_{1-8}$ alkyl or may be taken together to form a C5–8 cyclic ring, which can optionally be substituted by 1–5 halogen, $OR^2$ or $S(O)_mR^2$;

B is

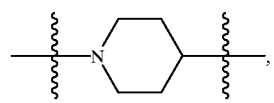

where attachment points are indicated by lines (ʃ) external to the rings which are optionally substituted by $C_1$–$C_6$ alkyl;

G is N;

Y is —$C(O)$—, —$C(OR^{11})$=, —$C(SR^{11})$=, —$C(NR^{11})$=, or —$C(R^{11})_2$—;

X is —$N(R^{11})$— or =N—;

$R^{11}$ is H, $C_1$–$C_8$ alkyl, $CF_3$, $CH_2CF_3$, —$(CH_2)_pOR^2$, —$(CH_2)_pN(R^2)_2$, $(CH2)_pN(R^2)C(O)N(R^2)_2$, —$(CH_2)_pN(R^2)C(O)R^2$, $(CH_2)_2$ heteroaryl, $(CH_2)_pN(R^2)SO_2C_1$–$C_4$ alkyl, —$(CH_2)_pC(O)N(R^2)_2$, or —$(CH_2)_pC(O)OR^2$ where heteroaryl is tetrazole, oxadiazole, imidazole or triazole which are optionally substituted with $R^2$, $OR^2$, $CF_3$ or $N(R^2)_2$ and where p is 0–3;

A is a fused aryl group group containing 6 atoms and being optionally substituted with 1–3 groups of $C_1$–$C_6$ alkyl, halogen, —$OR^2$, $N(R^2)_2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, —1H-tetrazol-5-yl, —$SO_2N(R^2)_2$, —$N(R^2)SO_2$ phenyl, $N(R^2)C(O)N(R^2)$ or —$N(R^2)SO_2R^2$, and in the case where regioisomers are present, all are included;

k is an integer from 0 to 1, such that when k is 0, Q is attached directly to $Z^2$;

m is an integer from 0 to 2;

n is an integer from 0 to 3;

q is an integer from 0 to 3; and t is an integer from 0 to 3.

16. A compound according to claim I represented by structural formula Ic:

Formula Ic

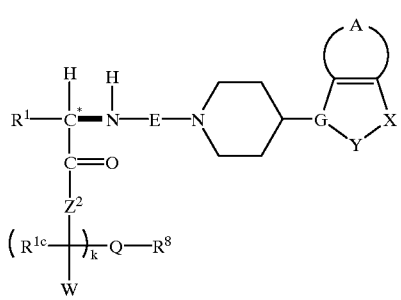

or a pharmaceutically acceptable salt or hydrate thereof, wherein:

$R^1$ is selected from the group consisting of: $C_1-C_{10}$ alkyl, aryl, aryl $(C_1-C_6$ alkyl), $(C_3-C_7$ cycloalkyl)$(C_1-C_6$ alkyl)—, $(C_1-C_5$ alkyl)-O-$(C_1-C_5$ alkyl)—, and aryl $(C_0-C_5$ alkyl)-O-$(C_1-C_5$ alkyl)—, where $R^2$ and alkyl may be further substituted by 1 to 5 halogen, $S(O)_mR^{2a}$, 1 to 3 of $OR^{2a}$ or $C(O)OR^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of $C_1-C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, —$SO_2N(R^2)(R^2)$, —$N(R^2)SO_2$ phenyl, or —$N(R^2)SO_2R^2$;

$R^2$ is selected from: hydrogen, $C_1-C_8$ alkyl, $(CH_2)_t$ aryl, and $C_3-C_7$ cycloalkyl, and where two $C_1-C_6$ alkyl groups are present on one atom, they optionally are joined to form a $C_3-C_8$ cyclic ring, optionally including oxygen, sulfur or $NR^{3a}$, where $R^{3a}$ is hydrogen, or $C_1-C_6$ alkyl, optionally substituted by hydroxyl;

$R^{2a}$ is selected from the group consisting of hydrogen and $C_1-C_3$ alkyl, said alkyl optionally substituted by hydroxyl;

$Z^2$ is selected from the group consisting of —O—, —$CH_2$—, —$CHR^{2b}$— and —$NR^{2b}$, when $Z^2$ is $NR^{2b}$ it can optionally be linked to $R^{1c}$, Q and/or W to form a $C_{5-8}$ cyclic ring;

$R^{2b}$ is selected from hydrogen, $C_1-C_8$ alkyl, $(CH_2)_t$ aryl, —$(CH_2)_nCO_2R^2$, —$(CH_2)_nCON(R^2)_2$, —$(CH_2)_nOH$, $(CH_2)_nCF_3$, $(CH_2)_t$ heteroaryl or —$(CH_2)_nOR^2$;

$R^{1c}$ is selected from the group consisting of hydrogen and $C_1-C_8$ alkyl;

W is selected from the group consisting of: hydrogen, $C_1-C_8$ alkyl, $(CH2)_t$ aryl, —$(CH_2)_qC(O)OR^2$, —$(CH_2)_qOR^2$, —$(CH_2)_qOC(O)R^2$, —$(CH_2)_qC(O)R^2$, —$(CH_2)_qC(O)(CH_2)_t$aryl, —$(CH_2)_qC(O)N(R^2)_2$, —$(CH_2)_qN(R^2)C(O)R^2$, —$(CH_2)_qN(R^2)SO_2R^2$, —$(CH_2)_qN(R^2)C(O)N(R^2)_2$, —$(CH_2)_qOC(O)N(R^2)_2$, —$(CH_2)_qN(R^2)C(O)OR^2$, —$(CH_2)_qN(R^2)SO_2N(R^2)_2$, —$(CH_2)_qS(O)_mR^2$, and $(CH_2)_t$ heteroaryl where the heteroaryl is preferably tetrazole, oxadiazole, thiadiazole, triazole or pyrazine, which is optionally substituted with $R^2$, $N(R^2)_2$ and $OR^2$, where $R^2$, $(CH_2)_q$ and $(CH_2)_t$ are optionally substituted with 1 to 2 $C_1-C_4$ alkyl, $OR^2$, $C(O)OR^2$, 1-3 halo and said aryl is optionally substituted with 1 to 3 halogen, —$OR^2$, —$CON(R^2)_2$, —$C(O)OR^2$, $C_1-C_4$ alkyl, —$S(O)_mR^2$, $N(R^2)_2$, $CF_3$ or 1H-tetrazol-5-yl;

Q is

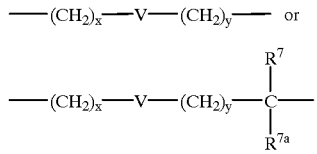

where x and y are independently 0, 1, 2, 3;

V is

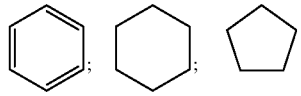

wherein said aromatic or non aromatic ring is optionally substituted with 1 to 2 $R^2$, 1 to 3 halogen, —$OR^2$, —$CON(R^2)_2$, —$C(O)OR^2$, $C_1-C_4$ alkyl, —$S(O)_mR^2$, $N(R^2)_2$, $CF_3$ or 1H-tetrazol-5-yl, and in the case where diastereo- or regio- isomers are present, all are included;

$R^7$ and $R^{7a}$ are independently trifluoromethyl or $R^2$;

$R^8$ is

$R^4$ and $R^5$ are independently selected from the group consisting of $R^2$, 2,2,2-trifluoroethyl, 3,3,3-trifluoropropyl, $(CH_2)_t$ cyclopropyl or $(CH_2)_nCO_2R^2$;

E is selected from the group consisting of —$SO_2$—, —$CO$—, —$C(=N-CN)$—, —$C(=N-NO_2)$— and —$C(=N-SO_2NH_2)$—;

$R^9$ and $R^{10}$ are independently H or $C_{1-8}$ alkyl;

G is N;

Y is —$C(O)$—, —$C(OR^{11})=$, —$C(SR^{11})=$, —$C(NR^{11})=$, or —$C(R^{11})_2$—;

X is —$N(R^{11})$—or =N—;

$R^{11}$ is H, $C_1-C_8$ alkyl, $CF_3$, $CH_2CF_3$, —$(CH_2)_pOR^2$, —$(CH_2)_pN(R^2)_2$, $(CH_2)_pN(R^2)C(O)N(R^2)_2$, —$(CH_2)_pN(R^2)C(O)R^2$, $(CH_2)_2$ heteroaryl, $(CH_2)_pN(R^2)SO_2C_1-C_4$ alkyl, —$(CH_2)_pC(O)N(R^2)_2$, or —$(CH_2)_pC(O)OR^2$ where heteroaryl is tetrazole, oxadiazole, imidazole or triazole which are optionally substituted with $R^2$, $OR^2$, $CF_3$ or $N(R^2)_2$ and where p is 0–3;

A is a fused aryl group, said aryl group containing 6 atoms and being optionally substituted with 1–3 groups of $C_1-C_6$ alkyl, halogen, —$OR^2$, $N(R^2)_2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, —1H-tetrazol-5-yl, —$SO_2N(R^2)_2$, —$N(R^2)SO_2$ phenyl, $N(R^2)C(O)N(R^2)$ or —$N(R^2)SO_2R^2$, and in the case where regioisomers are present, all are included;

k is an integer from 0 to 1, such that when k is 0, Q is attached directly to $Z^2$;

m is an integer from 0 to 2;
n is an integer from 0 to 3;
q is an integer from 0 to 3; and
t is an integer from 0 to 3.
17. A compound according to claim 1 having the Formula Id:
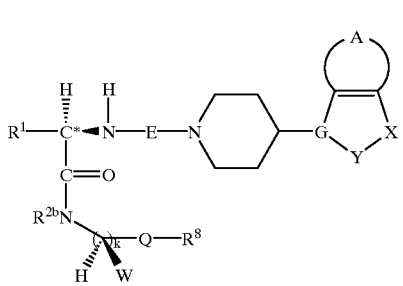
Formula Id
or a pharmaceutically acceptable salt or hydrate thereof, wherein
R¹ is selected from the group consisting of:
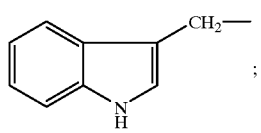
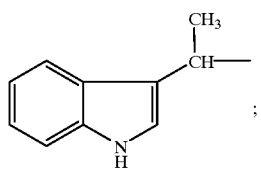
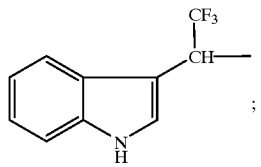
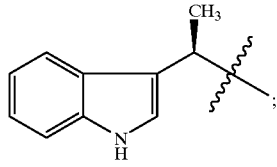
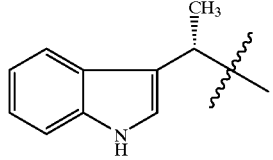
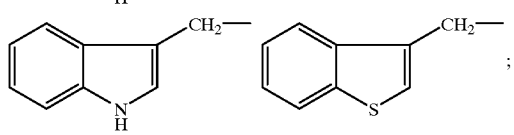
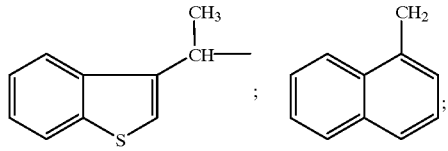
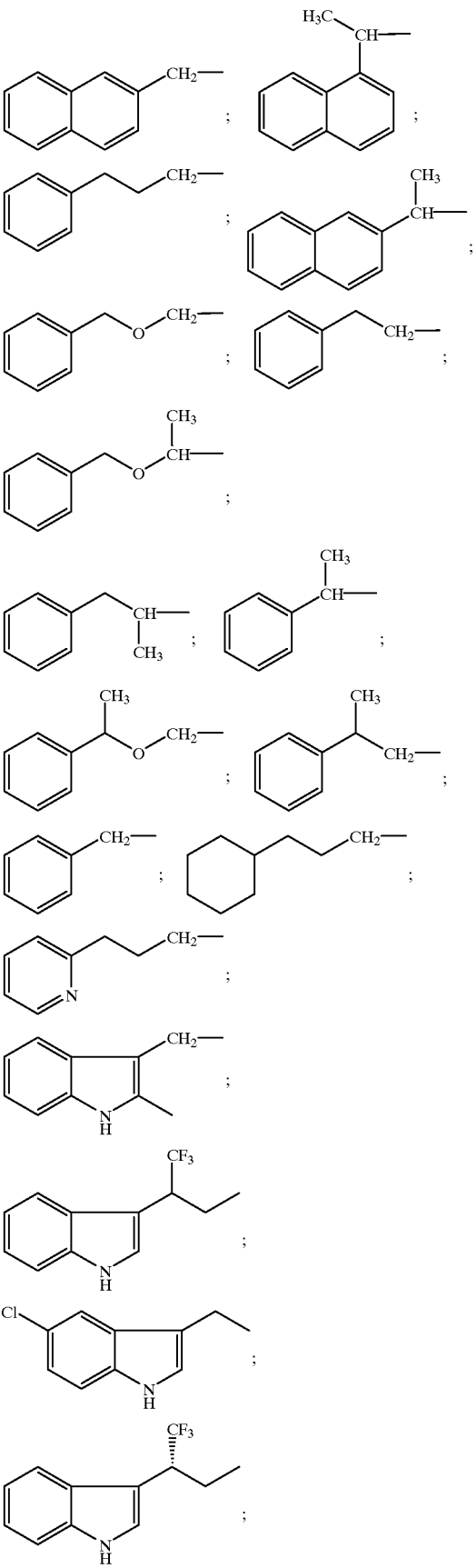

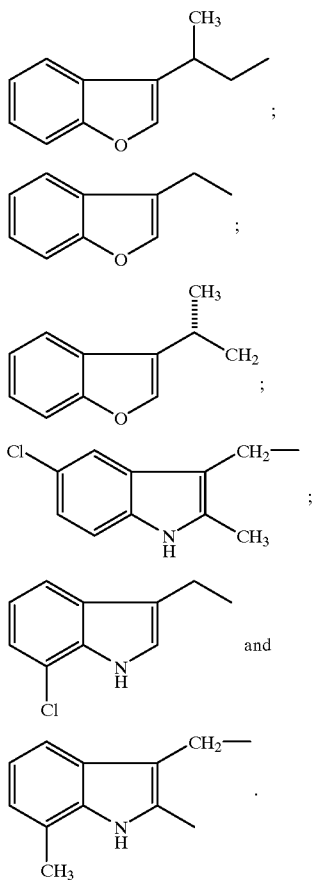

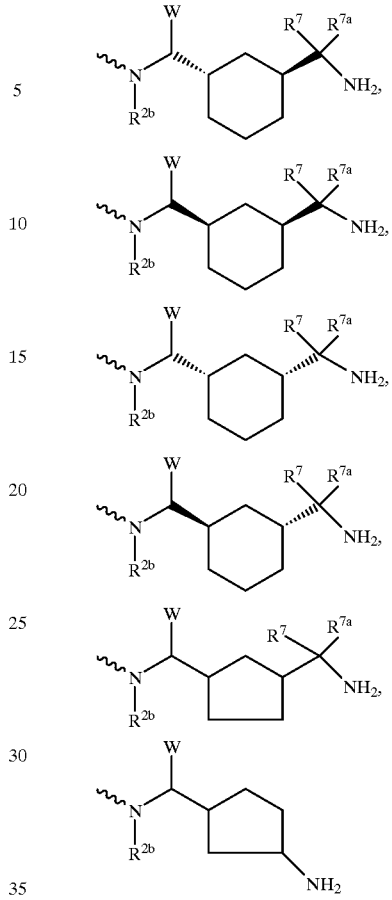

where the aryl is unsubstituted or substituted with a substitutent selected from: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, —$SO_2N(R^2)(R^2)$, —$N(R^2)SO_2$ phenyl, or —$N(R^2)SO_2R^2$;

$R^2$ is selected from: hydrogen, methyl, ethyl, propyl, isopropyl, butyl, isobutyl, t-butyl;

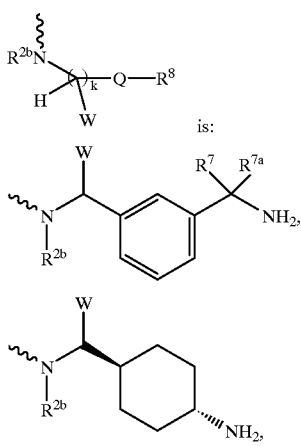

and the phenyl or cycloalkyl groups can be optionally substituted with 1 to 2 $R^{2,1}$ to 3 halogen, —$OR^2$, —$CON(R^2)_2$, —$C(O)OR^2$, $C_1$–$C_4$ alkyl, —$S(O)_mR^2$, $N(R^2)_2$, or $CF_3$; and in the case where diastereo- or regio- isomers are present, all are included;

W is selected from the group consisting of: hydrogen, $C_1$–$C_4$ alkyl or $(CH_2)_qC(O)OR^2$;

$R^7$ and $R^{7a}$ are independently trifluoromethyl or $R^2$;

$R^{2b}$ is selected from hydrogen, $C_1$–$C_4$ alkyl, $(CH_2)_nCF_3$ or $(CH_2)_t$ heteroaryl;

E is selected from the group consisting of —CO—, —C(=N—CN)—, and —$SO_2$—;

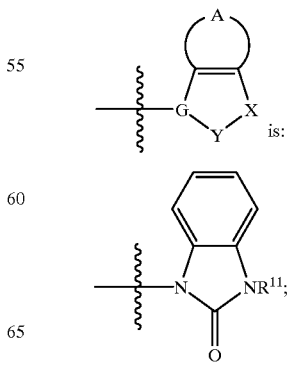

-continued

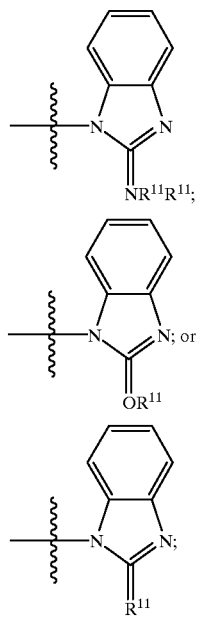

where the aromatic can be optionally substituted with 1–3 groups of $C_1$–$C_6$ alkyl, halogen, —$OR^2$, $N(R^2)_2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, —1H-tetrazol-5-yl, —$SO_2N(R^2)_2$, —$N(R^2)SO_2$ phenyl, $N(R^2)C(O)N(R^2)$ or —$N(R^2)SO_2R^2$;

$R^{11}$ is H, $C_1$–$C_8$ alkyl, $CF_3$, $CH_2CF_3$, —$(CH_2)_pOR^2$, —$(CH_2)_pN(R^2)_2$, $(CH_2)_pN(R^2)C(O)N(R^2)_2$, —$(CH_2)_pN(R^2)C(O)R^2$, $(CH_2)_p$ heteroaryl, $(CH_2)_pN(R^2)SO_2C_1$–$C_4$ alkyl, —$(CH_2)_pC(O)N(R^2)_2$, or —$(CH_2)_pC(O)OR^2$ where heteroaryl is tetrazole, oxadiazole, imidazole or triazole which are optionally substituted with $R^2$, $OR^2$, $CF_3$ or $N(R^2)_2$ and where p is 0–3;

m is an integer from 0 to 2;

n is an integer from 0 to 3; and q is an integer from 0 to 3.

18. A compound according to claim 1 or a pharmaceutically acceptable salt or hydrate thereof, which is selected from:

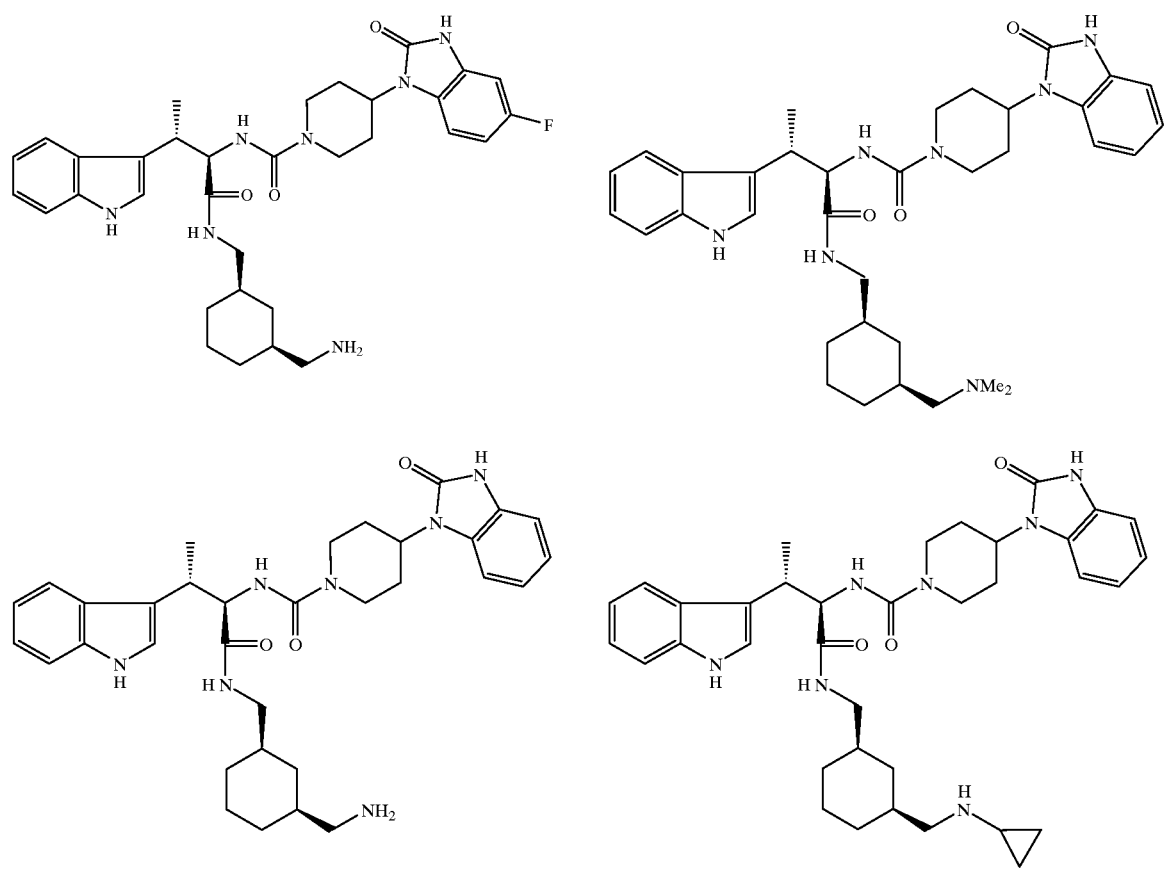

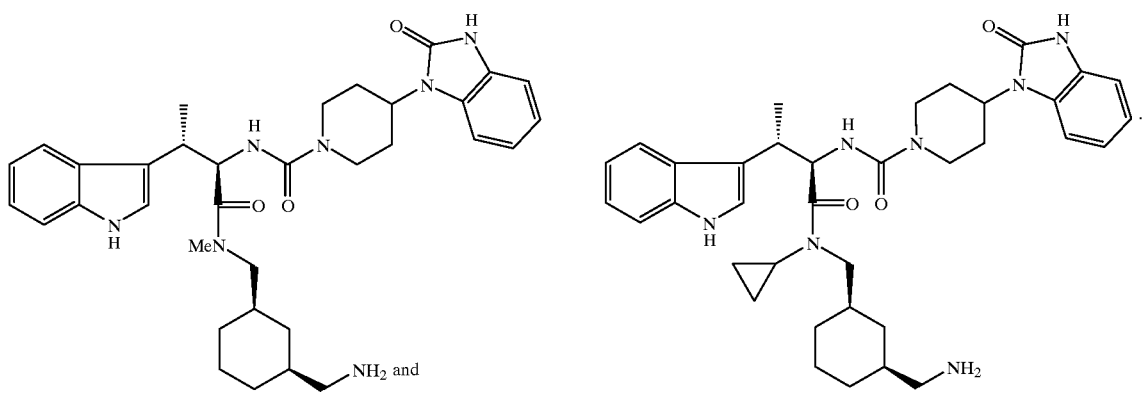
19. A compound according to claim 1, or a pharmaceutically acceptable salt or hydrate thereof, depicted in Table I below:
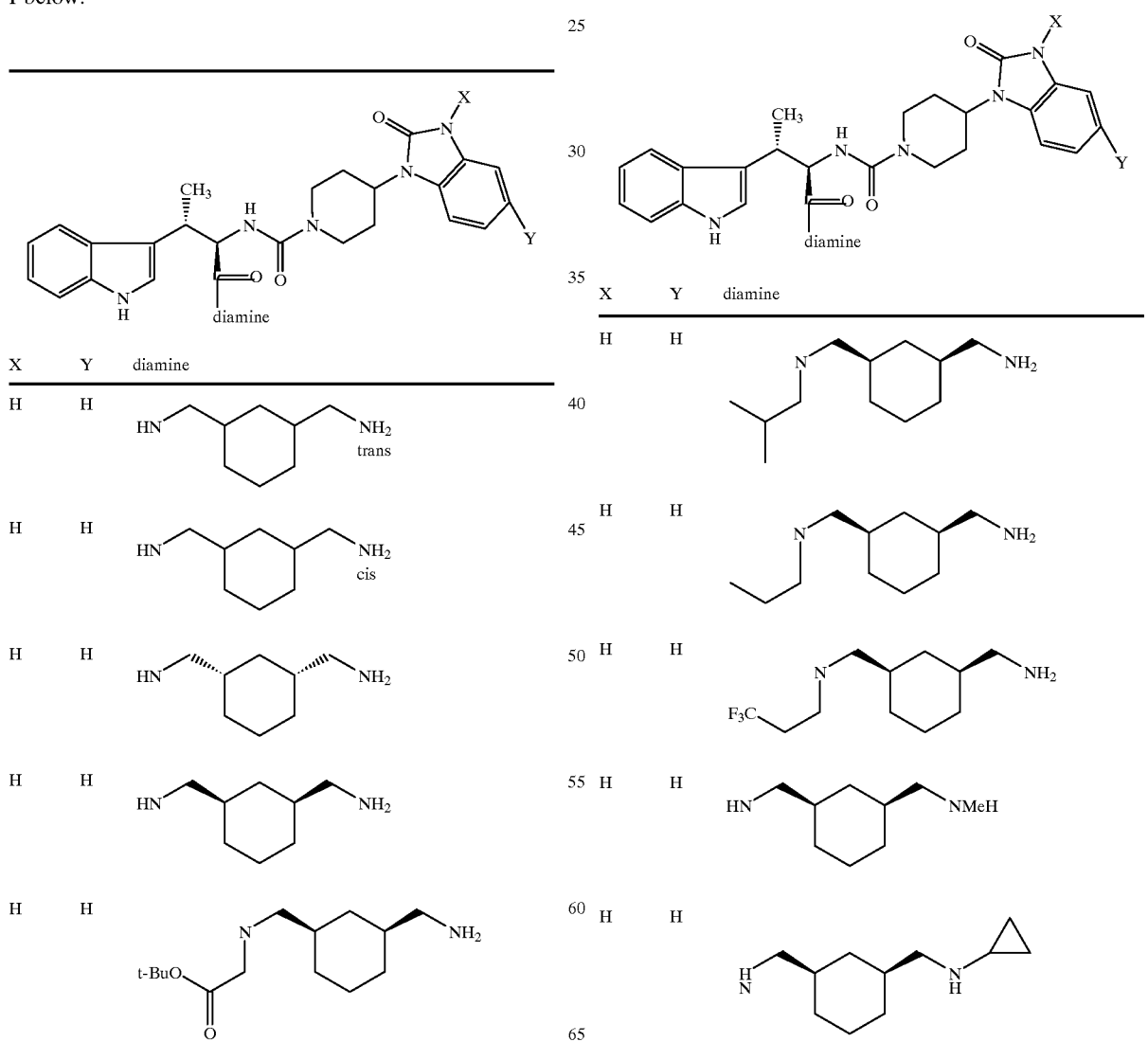

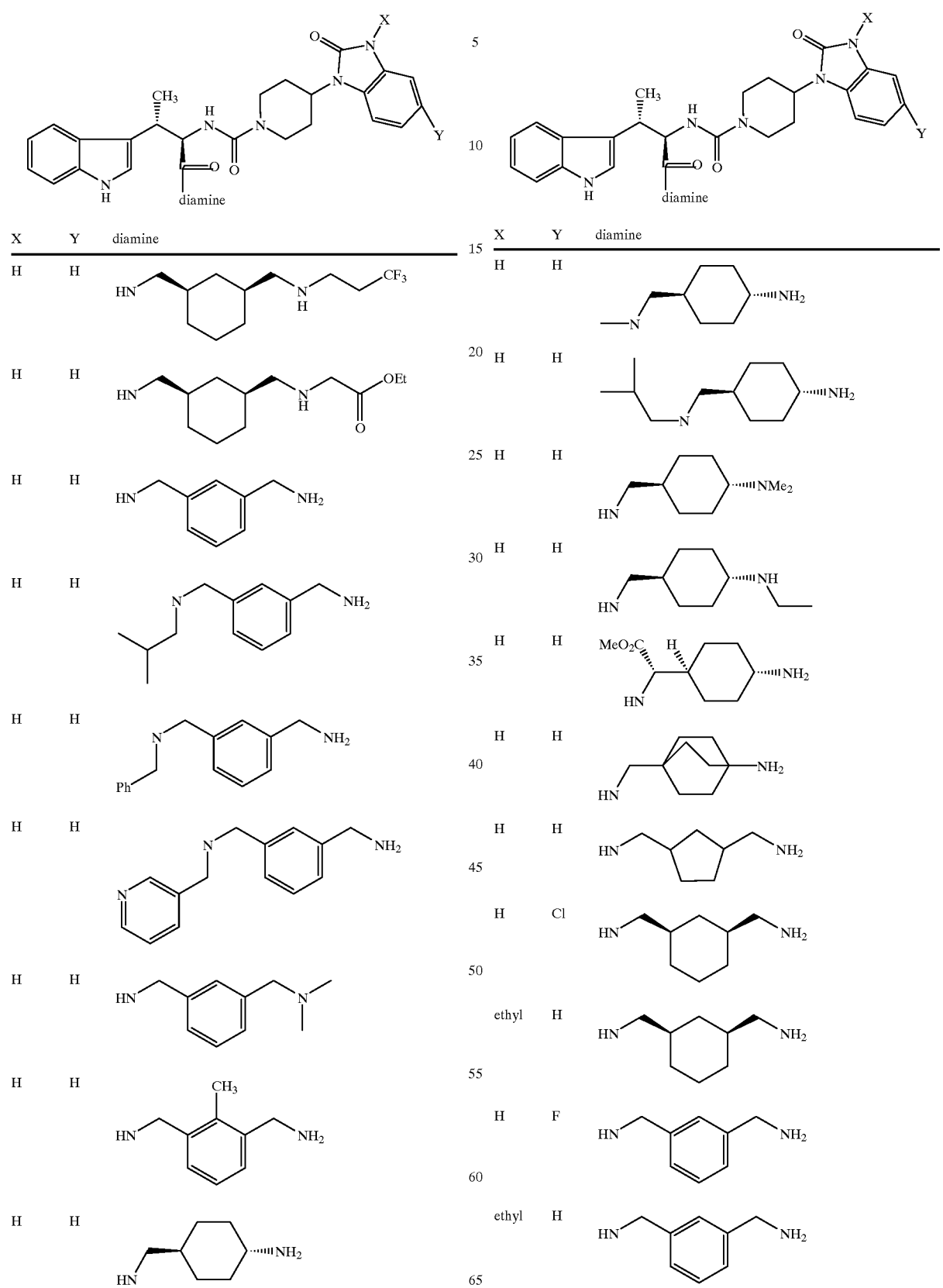

-continued

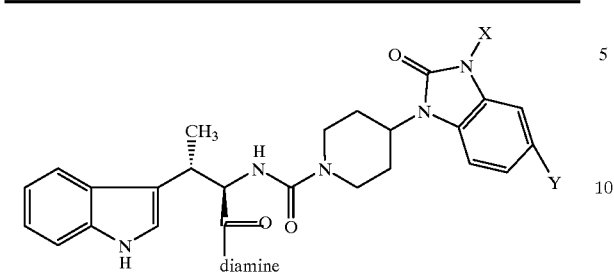

| X | Y | diamine |
|---|---|---------|
| H | H | 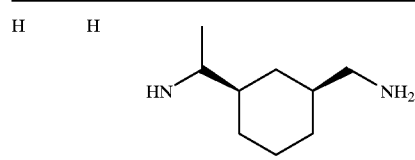 |
| H | H | 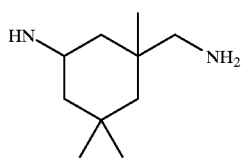 |
| H | H | 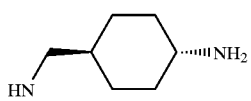 |

20. A compound according to claim 1, or a pharmaceutically acceptable salt or hydrate thereof, depicted in Table II below:

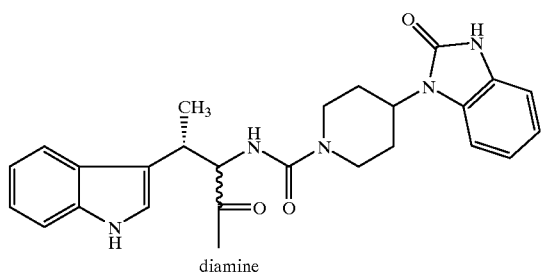

-continued

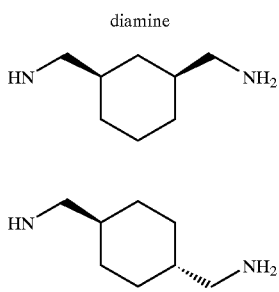

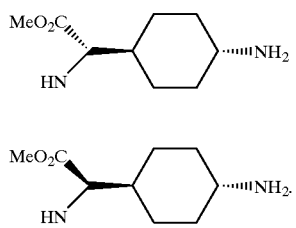

21. A method of treating diabetes disease in a mammal in need of such treatment, which comprises administering to said mammal an effective amount of a somatostatin agonist of claim 1.

22. A method of treating diabetes disease in a mammal in need of such treatment, which comprises administering to said mammal an effective amount of an orally active somatostatin agonist of claim 1.

23. A pharmaceutical composition comprising a compound according to claim 1 and a pharmaceutically acceptable carrier.

* * * * *